United States Patent
Bastos et al.

(10) Patent No.: US 10,344,023 B2
(45) Date of Patent: Jul. 9, 2019

(54) DERIVATIVES OF 3-HETEROARYLISOXAZOL-5-CARBOXYLIC AMIDE USEFUL FOR THE TREATMENT OF INTER ALIA CYSTIC FIBROSIS

(71) Applicant: Proteostasis Therapeutics, Inc., Cambridge, MA (US)

(72) Inventors: Cecilia M. Bastos, South Grafton, MA (US); Benito Munoz, Newtonville, MA (US); Bradley Tait, Malden, MA (US)

(73) Assignee: Proteostasis Therapeutics, Inc., Boston, MA (US)

( * ) Notice: Subject to any disclaimer, the term of this patent is extended or adjusted under 35 U.S.C. 154(b) by 0 days.

(21) Appl. No.: 15/539,405

(22) PCT Filed: Dec. 23, 2015

(86) PCT No.: PCT/US2015/000189
§ 371 (c)(1),
(2) Date: Jun. 23, 2017

(87) PCT Pub. No.: WO2016/105468
PCT Pub. Date: Jun. 30, 2016

(65) Prior Publication Data
US 2017/0362214 A1    Dec. 21, 2017

Related U.S. Application Data

(60) Provisional application No. 62/096,368, filed on Dec. 23, 2014, provisional application No. 62/102,203, filed on Jan. 12, 2015.

(51) Int. Cl.
*C07D 413/14* (2006.01)
*C07D 413/12* (2006.01)
*C07D 417/12* (2006.01)

(52) U.S. Cl.
CPC ......... *C07D 413/14* (2013.01); *C07D 413/12* (2013.01); *C07D 417/12* (2013.01)

(58) Field of Classification Search
CPC .................................................. C07D 413/14
USPC ....................................................... 514/378
See application file for complete search history.

(56) References Cited

U.S. PATENT DOCUMENTS

| | | | |
|---|---|---|---|
| 5,780,393 A | 7/1998 | Newton | |
| 5,888,941 A | 3/1999 | Bartroli et al. | |
| 7,846,951 B2 | 12/2010 | Miller et al. | |
| 7,915,297 B2 | 3/2011 | Cho et al. | |
| 7,981,935 B2 | 7/2011 | Olson et al. | |
| 8,193,225 B2 | 6/2012 | Schneider et al. | |
| 8,236,838 B2 | 8/2012 | Jones et al. | |
| 8,623,860 B2 | 1/2014 | Fleck et al. | |
| 8,815,924 B2 | 8/2014 | Dorsch et al. | |
| 9,745,292 B2 | 8/2017 | Bastos et al. | |
| 9,790,219 B2 | 10/2017 | Bastos et al. | |
| 2006/0041006 A1 | 2/2006 | Ibrahim et al. | |
| 2006/0100226 A1 | 5/2006 | Sikorski et al. | |
| 2008/0090882 A1 | 4/2008 | Dorsch et al. | |
| 2009/0069288 A1 | 3/2009 | Breinlinger et al. | |
| 2009/0163545 A1 | 6/2009 | Goldfarb | |
| 2009/0264486 A1 | 10/2009 | Jones et al. | |
| 2009/0318429 A1 | 12/2009 | Doyle et al. | |
| 2010/0234367 A1 | 9/2010 | Nomura et al. | |
| 2011/0003784 A1 | 1/2011 | Garvey et al. | |
| 2011/0082181 A1 | 4/2011 | Seiders et al. | |
| 2011/0212975 A1 | 9/2011 | Kao et al. | |
| 2012/0095002 A1 | 4/2012 | Ratcliffe et al. | |
| 2012/0264738 A1 | 10/2012 | Sugimoto et al. | |
| 2013/0072470 A1* | 3/2013 | Wishart | C07D 487/14 514/210.21 |
| 2013/0217883 A1 | 8/2013 | Adaway | |
| 2013/0237502 A1 | 9/2013 | Curtis et al. | |
| 2014/0364467 A1 | 12/2014 | Schneider et al. | |
| 2016/0151335 A1 | 6/2016 | Tait et al. | |
| 2017/0001991 A1 | 1/2017 | Bastos et al. | |
| 2017/0001993 A1 | 1/2017 | Bastos et al. | |
| 2017/0233379 A1 | 8/2017 | Bastos et al. | |
| 2017/0362214 A1 | 12/2017 | Bastos et al. | |
| 2017/0369480 A1 | 12/2017 | Bastos et al. | |
| 2017/0369482 A1 | 12/2017 | Bastos et al. | |

FOREIGN PATENT DOCUMENTS

| | | |
|---|---|---|
| CA | 2736441 A1 | 10/2012 |
| EP | 0337263 A2 | 10/1989 |
| EP | 0957099 A2 | 11/1999 |
| JP | 2006176443 A | 7/2006 |
| WO | WO-2002000651 A2 | 1/2002 |
| WO | WO-2003093297 A2 | 11/2003 |
| WO | WO-2005035514 A2 | 4/2005 |
| WO | WO-2005077345 A1 | 8/2005 |
| WO | WO-2005077373 A2 | 8/2005 |
| WO | WO-2006014134 A1 | 2/2006 |
| WO | WO-2006136924 A1 | 12/2006 |

(Continued)

OTHER PUBLICATIONS

Stoops et al., ACS Chem. Biol. (2011), vol. 6(5), pp. 452-465.*
King, Med. Chem: Principle and Practice (1994), pp. 206-208.*
"AID 775-Screen for Chemicals that Extend Yeast Lifespan," PubChem, 1-11 (Jul. 12, 2007), XP055331102.
Bai et al., "Synthesis and Structure-Activity Relationship Studies of Conformationally Flexible Tetrahydroisoquinolinyl Triazole Carboxamide and Triazole Substituted Benzamide Analogues as sigma 2 Receptor Ligands," Journal of Medicinal Chemistry, 57:10 4239-4251(2014), XP002754990.
CAS Registry No. 797781-85-2 (available Dec. 15, 2004).

(Continued)

*Primary Examiner* — Taofiq A Solola
(74) *Attorney, Agent, or Firm* — Goodwin Procter LLP

(57) ABSTRACT

The present disclosure is based, in part, on the discovery that disclosed compounds can increase cystic fibrosis transmembrane conductance regulator (CFTR) activity as measured in human bronchial epithelial (hBE) cells.

20 Claims, No Drawings

(56) References Cited

FOREIGN PATENT DOCUMENTS

| | | |
|---|---|---|
| WO | WO-2007075896 A2 | 7/2007 |
| WO | WO-2007078113 A1 | 7/2007 |
| WO | WO-2007086584 A1 | 8/2007 |
| WO | WO-2007126362 A1 | 11/2007 |
| WO | WO-2008046072 A2 | 4/2008 |
| WO | WO-2008051757 A1 | 5/2008 |
| WO | WO-2008070739 A1 | 6/2008 |
| WO | WO/2009/005269 * | 1/2009 |
| WO | WO-2009005269 A2 | 1/2009 |
| WO | WO-2009011850 A2 | 1/2009 |
| WO | WO-2009016241 A1 | 2/2009 |
| WO | WO-2010089297 A1 | 8/2010 |
| WO | WO-2010142801 A1 | 12/2010 |
| WO | WO-2011008931 A2 | 1/2011 |
| WO | WO/2011/020806 A1 * | 2/2011 |
| WO | WO/2011/073378 A1 * | 6/2011 |
| WO | WO/2011/094693 A1 * | 8/2011 |
| WO | WO-2012007500 A2 | 1/2012 |
| WO | WO-2013019561 A1 | 2/2013 |
| WO | WO-2013146970 A1 | 10/2013 |
| WO | WO-2014144860 A1 | 9/2014 |
| WO | WO-2014181287 A1 | 11/2014 |
| WO | WO-2014210159 A1 | 12/2014 |
| WO | WO-2015051230 A1 | 4/2015 |
| WO | WO-2015138909 A1 | 9/2015 |
| WO | WO-2015138934 A1 | 9/2015 |
| WO | WO-2015196071 A1 | 12/2015 |
| WO | WO-2016054560 A1 | 4/2016 |
| WO | WO-2016105468 A1 | 6/2016 |
| WO | WO-2016105477 A1 | 6/2016 |
| WO | WO-2016105484 A1 | 6/2016 |
| WO | WO-2016105485 A2 | 6/2016 |
| WO | WO-2016115090 A1 | 7/2016 |
| WO | WO-2017019589 A1 | 2/2017 |
| WO | WO-2017040606 A1 | 3/2017 |
| WO | WO-2017112853 A1 | 6/2017 |

OTHER PUBLICATIONS

Chang, X., "3-(2-chlorophenyl)-N-methylisoxazole-5-Carboxamide," Acta Crystallographica, Section E: Structure Reports Online, vol. E63(7), pp. 03074-sup-7 (2007).
Compound Summary for CID 70741394, Pubchem: Create Date: Mar. 4, 2013 [retrieved on May 12, 2015].
Compound Summary for CID 70756362, Pubchem: Create Date: Mar. 4, 2013 [retrieved on May 12, 2015].
Compound Summary for: CID 36257620, Pubchem: Create Date: May 29, 2009 [retrieved on May 12, 2015].
Compound Summary for: CID 55795703, Pubchem: Create Date: Jan. 25, 2012 [retrieved on May 12, 2015].
Demina et al., "5-substituted Pyridylisoxazoles as Effective Inhibitors of Platelet Aggregation," Russian Chemical Bulletin, International Edition, vol. 63(2) 2095-2113 (2014).
International Search Report and Written Opinion for International Application No. PCT/US2014/044100, dated Oct. 10, 2014, 8 pages.
International Search Report and Written Opinion for International Application No. PCT/US2015/000189, dated Mar. 18, 2016, 10 pages.
International Search Report and Written Opinion for International Application No. PCT/US2015/000202, dated Mar. 22, 2016, 8 pages.
International Search Report and Written Opinion for International Application No. PCT/US2015/000211, dated Mar. 29, 2016, 10 pages.
International Search Report and Written Opinion for International Application No. PCT/US2015/000212, dated Jul. 1, 2016, 22 pages.
International Search Report and Written Opinion for International Application No. PCT/US2015/020460, dated Jun. 9, 2015, 7 pages.
International Search Report and Written Opinion for International Application No. PCT/US2015/020499, dated Jun. 9, 2015, 8 pages.
International Search Report and Written Opinion for International Application No. PCT/US2015/036691, dated Aug. 20, 2015, 12 pages.
International Search Report and Written Opinion for International Application No. PCT/US2016/012982, dated Mar. 7, 2016, 12 pages.
International Search Report and Written Opinion for International Application No. PCT/US2016/043835, dated Oct. 10, 2016, 8 pages.
International Search Report and Written Opinion for International Application No. PCT/US2016/068266, dated Feb. 27, 2017, 11 pages.
International Search Report and Written Opinion for International Application No. PCT/US2017040606, dated Nov. 30, 2016, 10 pages.
Kalid et al., "Small Molecule Correctors of F508del-CFTR Discovered by Structure-based Virtual Screening," Journal of Computer-Aided Molecular Design, vol. 24:971-991 (2010).
Lack et al., "Targeting the Binding Function 3 (BF3) Site of the Human Androgen Receptor through Virtual Screening," Journal of Medicinal Chemistry, vol. 54(24) 8563-8573 (2011).
Liedtke, W., "Role of TRPV ion Channels in Sensory Transduction of Osmotic Stimuli in Mammals," Experimental Physiology, 92:3 507-512 (2007) XP055252392.
Lukevics et al.,"Synthesis and Cytotoxicity of Silyl- and Carbonyl-substituted Isoxazoles,"Chemistry of Heterocyclic Compounds, Springer New York LLC, vol. 36(10); 1226-1231 (1995).
Munchhof et al., "Discovery of PF-04449913, a Potent and Orally Bioavailable Inhibitor of Smoothened," ACS Medicinal Chemistry Letters, vol. 3(2) 106-111 (2012).
Phuan Puay-Wah et al., "Potentiators of Defective Delta F508-CFTR Gating that Do Not Interfere with Corrector Action," XP002754658, Database Accession No. PREV201500722877, Database Biosis [Online] Biosciences Information Service, Philadelphia, PA, US; Oct. 1, 2015 (Oct. 1, 2015). 1 page.
Pubchem: "ST062658 | C15H12N2O3—PubChem", Jul. 9, 2005 (Jul. 9, 2005), XP055331105, Retrieved from the Internet: URL:https://pubchem.ncbi.nlm.nih.gov/compound/973870#section=Biological-Test-Results [retrieved on Dec. 22, 2016].
Qian et al., "Potent MCH-1 Receptor Antagonists from Cis-1,4-Diaminocyclohexane-derived Indane Analogs," Bioorganic & Medicinal Chemistry Letters, 23:14 4216-4220 (2013).
Stoops et al., "Identification and Optimization of Small Molecules that Restore E-cadherin Expression and Reduce Invasion in Colorectal Carcinoma Cells," ACS Chemical Biology, American Chemical Society, Washington, DC, US, vol. 6., No. 5, pp. 452-465 (2011).
Supplemental European Search Report dated Jan. 9, 2017 in European Patent No. 14816975.8 (19 pages).
U.S. Appl. No. 15/653,934, "Compounds, Compositions, and Methods for Increasing CFTR Activity," filed Jul. 19, 2017 (76 pages).
U.S. Appl. No. 15/697,901, "Compounds, Compositions, and Methods for Increasing CFTR Activity," filed Sep. 7, 2017 (112 pages).
U.S. Appl. No. 15/542,997, "Compounds, Compositions, and Methods for Increasing CFTR Activity," filed Jul. 12, 2017 (175 pages).

* cited by examiner

DERIVATIVES OF 3-HETEROARYLISOXAZOL-5-CARBOXYLIC AMIDE USEFUL FOR THE TREATMENT OF INTER ALIA CYSTIC FIBROSIS

CROSS REFERENCE TO RELATED APPLICATIONS

This application is a national stage filing under 35 U.S.C. § 371 of PCT/US2015/000189, filed Dec. 23, 2015, which claims the benefit of, and priority to, U.S. provisional application Ser. Nos. 62/102,203, filed Jan. 12, 2015, and 62/096,368, filed Dec. 23, 2014, the contents of each of which are hereby incorporated by reference herein in their entirety.

BACKGROUND

Cells normally maintain a balance between protein synthesis, folding, trafficking, aggregation, and degradation, referred to as protein homeostasis, utilizing sensors and networks of pathways (Sitia et al., Nature 426: 891-894, 2003; Ron et al., Nat Rev Mol Cell Biol 8: 519-529, 2007). The cellular maintenance of protein homeostasis, or proteostasis, refers to controlling the conformation, binding interactions, location and concentration of individual proteins making up the proteome. Protein folding in vivo is accomplished through interactions between the folding polypeptide chain and macromolecular cellular components, including multiple classes of chaperones and folding enzymes, which minimize aggregation (Wiseman et al., Cell 131: 809-821, 2007). Whether a given protein folds in a certain cell type depends on the distribution, concentration, and subcellular localization of chaperones, folding enzymes, metabolites and the like (Wiseman et al.). Cystic fibrosis and other maladies of protein misfolding arise as a result of an imbalance in the capacity of the protein homeostasis (proteostasis) environment to handle the reduced energetic stability of misfolded, mutated proteins that are critical for normal physiology (Balch et al., Science 319, 916-9 (2008); Powers, et al., Annu Rev Biochem 78, 959-91 (2009); Hutt et al., FEBS Lett 583, 2639-46 (2009)).

Cystic Fibrosis (CF) is caused by mutations in the cystic fibrosis transmembrane conductance regulator (CFTR) gene which encodes a multi-membrane spanning epithelial chloride channel (Riordan et al., Annu Rev Biochem 77, 701-26 (2008)). Approximately ninety percent of patients have a deletion of phenylalanine (Phe) 508 (ΔF508) on at least one allele. This mutation results in disruption of the energetics of the protein fold leading to degradation of CFTR in the endoplasmic reticulum (ER). The ΔF508 mutation is thus associated with defective folding and trafficking, as well as enhanced degradation of the mutant CFTR protein (Qu et al., J Biol Chem 272, 15739-44 (1997)). The loss of a functional CFTR channel at the plasma membrane disrupts ionic homeostasis ($Cl^-$, $Na^+$, $HCO_3^-$) and airway surface hydration leading to reduced lung function (Riordan et al.). Reduced periciliary liquid volume and increased mucus viscosity impede mucociliary clearance resulting in chronic infection and inflammation, phenotypic hallmarks of CF disease (Boucher, J Intern Med 261, 5-16 (2007)). In addition to respiratory dysfunction, ΔF508 CFTR also impacts the normal function of additional organs (pancreas, intestine, gall bladder), suggesting that the loss-of-function impacts multiple downstream pathways that will require correction.

In addition to cystic fibrosis, mutations in the CFTR gene and/or the activity of the CFTR channel has also been implicated in other conditions, including for example, congenital bilateral absence of vas deferens (CBAVD), acute, recurrent, or chronic pancreatitis, disseminated bronchiectasis, asthma, allergic pulmonary aspergillosis, smoking-related lung diseases, such as chronic obstructive pulmonary disease (COPD), dry eye disease, Sjogren's syndrome and chronic sinusitis, (Sloane et al. (2012), PLoS ONE 7(6): e39809.doi:10.1371/journal.pone.0039809; Bombieri et al. (2011), J Cyst Fibros. 2011 June; 10 Suppl 2:S86-102; (Albert et al. (2008). Clinical Respiratory Medicine, Third Ed., Mosby Inc.; Levin et al. (2005), Invest Ophthalmol Vis Sci., 46(4):1428-34; Froussard (2007), Pancreas 35(1): 94-5).

There remains a need in the art for compounds, compositions and methods of increasing CFTR activity as well as for methods of treating CF, other CFTR-related diseases, and other maladies of protein misfolding.

SUMMARY

The present disclosure is based, in part, on the discovery that disclosed compounds increase cystic fibrosis transmembrane conductance regulator (CFTR) activity as measured in human bronchial epithelial (hBE) cells.

Disclosed herein, in an embodiment, are compounds such as those having the Formula (IV):

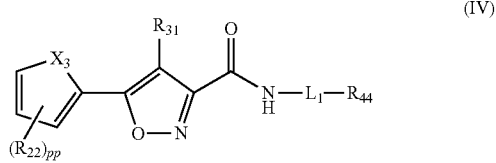

(IV)

or a pharmaceutically acceptable salt, prodrug or solvate thereof, wherein:

$X_3$ is selected from the group consisting of O, S, and $NR_{hh}$;

pp is 1, 2, or 3;

$R_{22}$ is independently selected for each occurrence from the group consisting of hydrogen, halogen, and $C_{1-4}$alkyl (optionally substituted by one, two or three halogens);

$R_{31}$ is selected from the group consisting of hydrogen, halogen, and $C_{1-4}$alkyl;

$L_1$ is selected from the group consisting of $C_1$-6alkylene, $C_{3-6}$cycloalkylene, $C_{3-6}$cycloalkylene-$C_{1-4}$alkylene, $C_{1-3}$alkylene-$NR_{hh}$—$S(O)_w$—, —$C_{1-3}$alkylene-$S(O)_w$—$NR_{hh}$—, $C_{3-6}$cycloalkylene-$C_{0-2}$alkylene-$S(O)_w$—$NR_{hh}$, and $C_{3-6}$cycloalkylene-$C_{0-2}$alkylene $NR_{hh}$—$S(O)_w$—, wherein $L_1$ may be optionally substituted by one, two or three substituents selected from the group consisting of halogen, hydroxyl, and $C_{1-3}$alkyl (optionally substituted by one, two or three substituents each selected independently from $R_{ff}$);

$R_{44}$ is selected from the group consisting of heterocycle and a 5-6 membered monocyclic or 8-10 membered bicyclic heteroaryl having one, two or three heteroatoms each selected from O, N, and S; wherein the heterocycle and the heteroaryl may be optionally substituted by one or two substituents each selected independently from $R_{gg}$;

$R_{ff}$ is selected for each occurrence from group consisting of halogen, hydroxyl, $C_{1-4}$alkyl, $C_{1-4}$alkyoxy, $C_{2-4}$alkenyl, $C_{3-6}$cycloalkyl, —NR'R", —NR'—$S(O)_w$—$C_{1-3}$alkyl, S$(O)_w$—NR'R", and —$S(O)_w$—$C_{1-3}$alkyl, where w is 0, 1, or 2, wherein $C_{1-4}$alkyl, $C_{1-4}$alkyoxy, $C_{2-4}$alkenyl and $C_{3-6}$cycloalkyl may be optionally substituted by one, two or three substituents each independently selected from the group consisting of halogen, hydroxyl, —NR'R", —NR'—S(O)$_w$—C$_{1-3}$alkyl, S(O)$_w$—NR'R", and —S(O)$_w$—C$_{1-3}$alkyl;

R$_{gg}$ is selected for each occurrence from group consisting of halogen, hydroxyl, C$_{1-6}$alkyl, C$_{1-6}$alkyoxy, C$_{2-6}$alkenyl, C$_{3-6}$cycloalkyl, —NR'R", —NR'—S(O)$_w$—C$_{1-3}$alkyl, S(O)$_w$ —NR'R", —O—Si(R''')$_3$, and —S(O)$_w$—C$_{1-3}$alkyl, where w is 0, 1, or 2, wherein C$_{1-6}$alkyl, C$_{1-6}$alkyoxy, C$_{2-6}$alkenyl and C$_{3-6}$cycloalkyl may each be optionally substituted by one, two or three substituents each independently selected from the group consisting of halogen, C$_{1-6}$alkyl, C$_{1-6}$alkoxy, hydroxyl, C(O)OH, —C(O)OC$_{1-6}$alkyl, —O—C$_{3-6}$cycloalkyl, —O-heterocycle, —O-heteroaryl, —O-phenyl, —NR'R", —NR'—S(O)$_w$—C$_{1-3}$alkyl, —O—Si(R''')$_3$, S(O)$_w$ —NR'R", and —S(O)$_w$—C$_{1-3}$alkyl;

w is 0, 1 or 2; and

R$_{hh}$ is selected for each occurrence from the group consisting of H, C$_{1-6}$alkyl and C$_{3-6}$cycloalkyl;

R' and R" are selected for each occurrence from the group consisting of H, C$_{1-6}$alkyl and C$_{3-6}$cycloalkyl; and each R''' is selected for each occurrence from C$_{1-6}$alkyl.

Also contemplated herein are pharmaceutical compositions that include a disclosed compound such as those compounds having Formula (IV) and a pharmaceutically acceptable carrier or excipient. In certain embodiments, the compositions can include at least one additional CFTR modulator as described anywhere herein or at least two additional CFTR modulators, each independently as described anywhere herein.

In additional embodiments, a method of enhancing (e.g., increasing) cystic fibrosis transmembrane conductance regulator (CFTR) activity in a subject in need thereof is provided comprising administering to said subject an effective amount of a compound of Formula (IV).

In certain of these embodiments, the activity of one or more (e.g., one or two) mutant CFTRs (e.g., ΔF508, S549N, G542X, G551D, R117H, N1303K, W1282X, R553X, 621+1G>T, 1717-1G>A, 3849+10kbC>T, 2789+5G>A, 3120+1G>A, I507del, R1162X, 1898+1G>A, 3659delC, G85E, D1152H, R560T, R347P, 2184insA, A455E, R334W, Q493X, and 2184delA CFTR) is enhanced (e.g., increased). In certain embodiments, ΔF508 CFTR activity is enhanced (e.g., increased). In other embodiments, the activities of two mutant CFTRs (e.g., ΔF508 and G551D; ΔF508 and A455E; or G542X; Δ508F) are enhanced (e.g., increased).

In certain of these embodiments, the subject (e.g., a human patient) is suffering from a disease associated with decreased CFTR activity (e.g., cystic fibrosis, congenital bilateral absence of vas deferens (CBAVD), acute, recurrent, or chronic pancreatitis, disseminated bronchiectasis, asthma, allergic pulmonary aspergillosis, chronic obstructive pulmonary disease (COPD), chronic sinusitis, dry eye disease, protein C deficiency, A-β-lipoproteinemia, lysosomal storage disease, type 1 chylomicronemia, mild pulmonary disease, lipid processing deficiencies, type 1 hereditary angioedema, coagulation-fibrinolyis, hereditary hemochromatosis, CFTR-related metabolic syndrome, chronic bronchitis, constipation, pancreatic insufficiency, hereditary emphysema, Sjogren's syndrome, familial hypercholesterolemia, I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, nephrogenic DI, Charcot-Marie Tooth syndrome, Perlizaeus-Merzbacher disease, Alzheimer's disease, Parkinson's disease, amyotrophic lateral sclerosis, progressive supranuclear palsy, Pick's disease, Huntington's disease, spinocerebellar ataxia type I, spinal and bulbar muscular atrophy, dentatorubral pallidoluysian, myotonic dystrophy, hereditary Creutzfeldt-Jakob disease (due to prion protein processing defect), Fabry disease, and Straussler-Scheinker syndrome). In certain embodiments, the disease is cystic fibrosis.

In yet additional aspects, the disclosure is directed to treating a patient suffering from cystic fibrosis comprising administering to said patient an effective amount of a disclosed compound.

In some embodiments, the methods described herein can further include administering an additional therapeutic agent or administering at least two additional CFTR therapeutic agents. In some embodiments, the methods described herein can further include administering an additional CFTR modulator or administering at least two additional CFTR modulators. In certain embodiments, at least one CFTR modulator is a CFTR corrector (e.g., VX-809, VX-661, VX-983, VX-152, VX-440, GLPG2222 and GLPG2665) or potentiator (e.g., ivacaftor, genistein and GLPG1837). In certain of these embodiments, one of the at least two additional therapeutic agents is a CFTR corrector (e.g., VX-809, VX-661, VX-983, VX-152, VX-440, GLPG2222 and GLPG2665) and the other is a CFTR potentiator (e.g., ivacaftor and genistein). In certain of these embodiments, one of the at least two additional therapeutic agents is a CFTR corrector (e.g., GLPG2222 or GLPG2665) and the other is a CFTR potentiator (e.g., GLPG1837).

In a further aspect, a method of identifying a candidate agent that increases CFTR activity is provided, which includes: (i) contacting a cell that expresses a CFTR protein with the candidate agent and a disclosed compound; (ii) measuring the CFTR activity in the cell in the presence of the candidate agent and the disclosed compound; and (iii) comparing the CFTR activity to that in the absence of the test agent, wherein an increase in CFTR activity in the presence of the test agent indicates that the agent increases CFTR activity. In certain embodiments, the cell expresses a mutant CFTR protein. In certain embodiments, CFTR activity is measured by measuring chloride channel activity of the CFTR, and/or other ion transport activity. In certain of these embodiments, the method is high-throughput. In certain of these embodiments, the candidate agent is a CFTR corrector or a CFTR potentiator.

DETAILED DESCRIPTION

As used herein, the words "a" and "an" are meant to include one or more unless otherwise specified. For example, the term "an agent" encompasses both a single agent and a combination of two or more agents.

As discussed above, the present disclosure is directed in part to compounds as described herein having the Formula (IV), or a pharmaceutically acceptable salt, prodrug or solvate thereof, pharmaceutical compositions, methods of increasing CFTR activity and methods of treating cystic fibrosis.

For example, disclosed herein are compounds such as those having the Formula (IV):

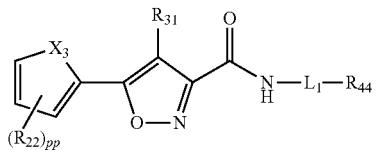

or a pharmaceutically acceptable salt, prodrug or solvate thereof, wherein:

$X_3$ is selected from the group consisting of O, S, and $NR_{hh}$;

pp is 1, 2, or 3;

$R_{22}$ is independently selected for each occurrence from the group consisting of hydrogen, halogen, and $C_{1-4}$alkyl (optionally substituted by one, two or three halogens);

$R_{31}$ is selected from the group consisting of hydrogen, halogen, and $C_{1-4}$alkyl;

$L_1$ is selected from the group consisting of $C_1$-6alkylene, $C_{3-6}$cycloalkylene, $C_{3-6}$cycloalkylene-$C_{1-4}$alkylene, $C_{1-3}$alkylene-$NR_{hh}$—S(O)$_w$—, —$C_{1-3}$alkylene-S(O)$_w$—$NR_{hh}$—, $C_{3-6}$cycloalkylene-$C_{0-2}$alkylene-S(O)$_w$—$NR_{hh}$, and $C_{3-6}$cycloalkylene-$C_{0-2}$alkylene $NR_{hh}$—S(O)$_w$—, wherein $L_1$ may be optionally substituted by one, two or three substituents selected from the group consisting of halogen, hydroxyl, and $C_{1-3}$alkyl (optionally substituted by one, two or three substituents each selected independently from $R_{ff}$);

$R_{44}$ is selected from the group consisting of heterocycle and a 5-6 membered monocyclic or 8-10 membered bicyclic heteroaryl having one, two or three heteroatoms each selected from O, N, and S; wherein the heterocycle and the heteroaryl may be optionally substituted by one or two substituents each selected independently from $R_{gg}$;

$R_{ff}$ is selected for each occurrence from group consisting of halogen, hydroxyl, $C_{1-4}$alkyl, $C_{1-4}$alkyoxy, $C_{2-4}$alkenyl, $C_{3-6}$cycloalkyl, —NR'R", —NR'—S(O)$_w$—$C_{1-3}$alkyl, S(O)$_w$—NR'R", and —S(O)$_w$—$C_{1-3}$alkyl, where w is 0, 1, or 2, wherein $C_{1-4}$alkyl, $C_{1-4}$alkyoxy, $C_{2-4}$alkenyl and $C_{3-6}$cycloalkyl may be optionally substituted by one, two or three substituents each independently selected from the group consisting of halogen, hydroxyl, —NR'R", —NR'—S(O)$_w$—$C_{1-3}$alkyl, S(O)$_w$—NR'R", and —S(O)$_w$—$C_{1-3}$alkyl;

$R_{gg}$ is selected for each occurrence from group consisting of halogen, hydroxyl, $C_{1-6}$alkyl, $C_{1-6}$alkyoxy, $C_{2-6}$alkenyl, $C_{3-6}$cycloalkyl, —NR'R", —NR'—S(O)$_w$—$C_{1-3}$alkyl, S(O)$_w$—NR'R",
—O—Si(R''')$_3$, and —S(O)$_w$—$C_{1-3}$alkyl, where w is 0, 1, or 2, wherein $C_{1-6}$alkyl, $C_{1-6}$alkyoxy, $C_{2-6}$alkenyl and $C_{3-6}$cycloalkyl may each be optionally substituted by one, two or three substituents each independently selected from the group consisting of halogen, $C_{1-6}$alkyl, $C_{1-6}$alkoxy, hydroxyl, C(O)OH, —C(O)OC$_{1-6}$alkyl, —O—$C_{3-6}$cycloalkyl, —O-heterocycle, —O-heteroaryl, —O-phenyl, —NR'R", —NR'—S(O)$_w$—$C_{1-3}$alkyl, —O—Si(R''')$_3$, S(O)$_w$—NR'R", and —S(O)$_w$—$C_{1-3}$alkyl;

w is 0, 1 or 2; and $R_{hh}$ is selected for each occurrence from the group consisting of H, $C_{1-6}$alkyl and $C_{3-6}$cycloalkyl;

R' and R" are selected for each occurrence from the group consisting of H, $C_{1-6}$alkyl and $C_{3-6}$cycloalkyl; and each R''' is selected for each occurrence from $C_{1-6}$alkyl.

In some embodiments, $L_1$ is $C_{1-3}$alkylene, $C_{3-5}$cycloalkylene (e.g., $C_4$ cycloalkylene), or $C_{3-6}$cycloalkylene-$C_{1-4}$alkylene. In other embodiments, $L_1$ is $C_{1-3}$alkylene-$NR_{hh}$—S(O)$_w$—, or —$C_{1-3}$alkylene-S(O)$_w$—$NR_{hh}$—. In some embodiments, $R_{31}$ is H or F.

For example, in certain embodiments, $R_{22}$ is selected independently for each occurrence from H and $CH_3$.

A disclosed compound may be represented by, in certain embodiments:

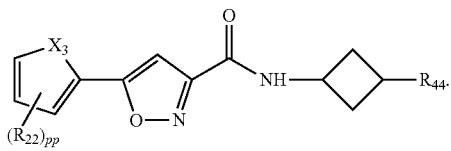

$R_{44}$ may be a 5-membered heteroaryl having two or three nitrogens, for example, in certain of the above formulas. In other embodiments, $R_{44}$ is a 5 membered heteroaryl having two nitrogens and additional heteroatom selected from O or S. In certain of these embodiments, $R_{44}$ is substituted on a free carbon by a substituent selected from the group consisting of: a methyl substituted by one, two or three substituents each selected from halogen, hydroxyl, methoxy and ethoxy, ethyl substituted by one, two or three substituents each selected from halogen, hydroxyl, methoxy and ethoxy, propyl substituted by one, two or three substituents each selected from halogen, hydroxyl, methoxy and ethoxy), isopropyl substituted by one, two or three substituents each selected from halogen, hydroxyl, methoxy and ethoxy, n-butyl substituted by one, two or three substituents each selected from halogen, hydroxyl, methoxy and ethoxy, t-butyl substituted by one, two or three substituents each selected from halogen, hydroxyl, methoxy and ethoxy, s-butyl substituted by one, two or three substituents each selected from halogen, hydroxyl, methoxy and ethoxy and isobutyl substituted by one, two or three substituents each selected from halogen, hydroxyl, methoxy and ethoxy.

For example, $R_{44}$ can be selected from the group consisting of:

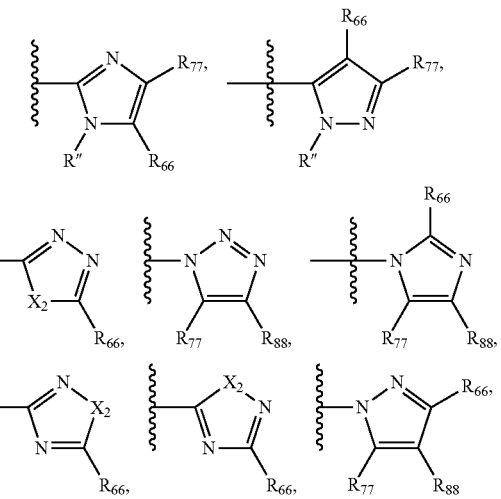

-continued

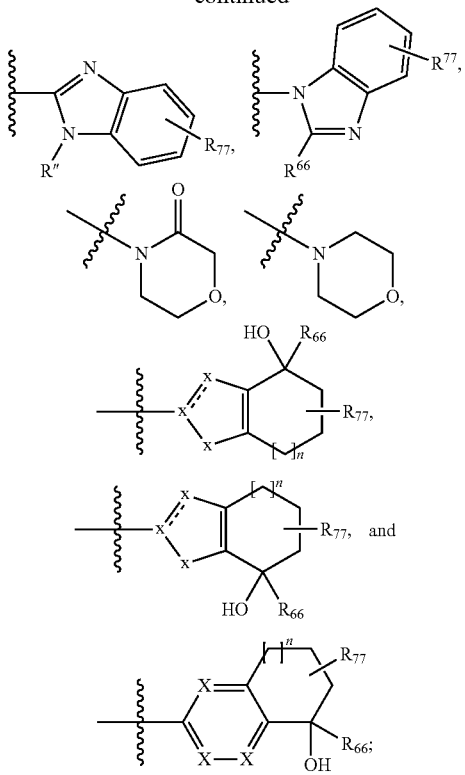

wherein X independently for each occurrence is selected from the group consisting of O, S, $NR_{hh}$, C, $C(R_{88})$, and $C(R_{88})(R_{99})$; $X_2$ independently for each occurrence is selected from the group consisting of O, S and $NR_{hh}$; R" is H or $C_{1-4}$alkyl, each $R_{66}$, $R_{77}$, $R_{88}$ and $R_{99}$ is independently selected for each occurrence from H and $R_{gg}$, and n is 0, 1, 2, or 3.

In certain embodiments, $R_{44}$ is represented by:

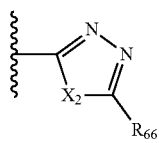

wherein $R_{66}$ is selected from the group consisting of: a methyl substituted by one, two or three substituents each selected from halogen, hydroxyl, methoxy and ethoxy, ethyl substituted by one, two or three substituents each selected from halogen, hydroxyl, methoxy and ethoxy, propyl substituted by one, two or three substituents each selected from halogen, hydroxyl, methoxy and ethoxy), isopropyl substituted by one, two or three substituents each selected from halogen, hydroxyl, methoxy and ethoxy, n-butyl substituted by one, two or three substituents each selected from halogen, hydroxyl, methoxy and ethoxy, t-butyl substituted by one, two or three substituents each selected from halogen, hydroxyl, methoxy and ethoxy, s-butyl substituted by one, two or three substituents each selected from halogen, hydroxyl, methoxy and ethoxy, and isobutyl substituted by one, two or three substituents each selected from halogen, hydroxyl, methoxy and ethoxy.

In certain embodiments, each of $R_{66}$, $R_{77}$ and $R_{88}$ is selected from the group consisting of H, halogen, methyl (optionally substituted by one, two or three substituents each selected from halogen, hydroxyl, methoxy and ethoxy), ethyl (optionally substituted by one, two or three substituents each selected from halogen, hydroxyl, methoxy and ethoxy), propyl (optionally substituted by one, two or three substituents each selected from halogen, hydroxyl, methoxy and ethoxy), isopropyl (optionally substituted by one, two or three substituents each selected from halogen, hydroxyl, methoxy and ethoxy), n-butyl (optionally substituted by one, two or three substituents each selected from halogen, hydroxyl, methoxy and ethoxy), t-butyl (optionally substituted by one, two or three substituents each selected from halogen, hydroxyl, methoxy and ethoxy), s-butyl (optionally substituted by one, two or three substituents each selected from halogen, hydroxyl, methoxy and ethoxy) and isobutyl (optionally substituted by one, two or three substituents each selected from halogen, hydroxyl, methoxy and ethoxy).

In certain embodiments, $R_{44}$ can be selected from the group consisting of tetrahydropyranyl, thiadiazolyl, tetrahydrofuranyl, and morpholinyl. In certain embodiments, $R_{44}$ can be a monocyclic heteroaryl containing one, two or three ring nitrogen atoms. In certain embodiments, $R_{4a}$ can be selected from the group consisting of furanyl, pyridinyl, pyrazinyl, pyrazolyl, imidazolyl, isoxazolyl, triazolyl, thiazolyl, oxadiazolyl, thiadiazolyl, thienyl, piperazinyl, and benzimidazolyl, each optionally substituted.

Also disclosed herein are compounds such as those having the Formula (V):

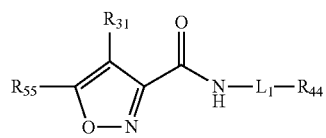

and pharmaceutically acceptable salts, stereoisomers, and prodrugs thereof, wherein;

$R_{55}$ is pyridinyl;

$R_{31}$ is selected from the group consisting of hydrogen, halogen, and $C_{1-4}$alkyl;

$L_1$ is selected from the group consisting of $C_{1-6}$alkylene, $C_{3-6}$cycloalkylene, $C_{3-6}$cycloalkylene-$C_{1-4}$alkylene, $C_{1-3}$alkylene-$NR_{hh}$—S(O)$_w$—, —$C_{1-3}$alkylene-S(O)$_w$—$NR_{hh}$—, $C_{3-6}$cycloalkylene-$C_{0-2}$alkylene-S(O)$_w$—$NR_{hh}$, and $C_{3-6}$cycloalkylene-$C_{0-2}$alkylene $NR_{hh}$—S(O)$_w$—, wherein $L_1$ may be optionally substituted by one, two or three substituents selected from the group consisting of halogen, hydroxyl, and $C_{1-3}$alkyl (optionally substituted by one, two or three substituents each selected independently from $R_{ff}$);

$R_{44}$ is selected from the group consisting of heterocycle and a 5-6 membered monocyclic or 8-10 membered bicyclic heteroaryl having one, two or three heteroatoms each selected from O, N, and S; wherein the heterocycle and the heteroaryl may be optionally substituted by one or two substituents each selected independently from $R_{gg}$;

$R_{ff}$ is selected for each occurrence from group consisting of halogen, hydroxyl, $C_{1-4}$alkyl, $C_{1-4}$alkyoxy, $C_{2-4}$alkenyl, $C_{3-6}$cycloalkyl, —NR'R", —NR'—S(O)$_w$—$C_{1-3}$alkyl, S(O)$_w$ —NR'R", and —S(O)$_w$—$C_{1-3}$alkyl, where w is 0, 1, or 2, wherein $C_{1-4}$alkyl, $C_{1-4}$alkyoxy, $C_{2-4}$alkenyl and $C_{3-6}$cycloalkyl may be optionally substituted by one, two or three substituents each independently selected from the group consisting of halogen, hydroxyl, —NR'R", —NR'—S(O)$_w$—C$_{1-3}$alkyl, S(O)$_w$—NR'R", and —S(O)$_w$—C$_{1-3}$alkyl;

R$_{gg}$ is selected for each occurrence from group consisting of halogen, hydroxyl, C$_{1-6}$alkyl, C$_{1-6}$alkyoxy, C$_{2-6}$alkenyl, C$_{3-6}$cycloalkyl, —NR'R", —NR'—S(O)$_w$—C$_{1-3}$alkyl, S(O)$_w$ —NR'R", —O—Si(R''')$_3$, and —S(O)$_w$—C$_{1-3}$alkyl, where w is 0, 1, or 2, wherein C$_{1-6}$alkyl, C$_{1-6}$alkyoxy, C$_{2-6}$alkenyl and C$_{3-6}$cycloalkyl may each be optionally substituted by one, two or three substituents each independently selected from the group consisting of halogen, C$_{1-6}$alkyl, C$_{1-6}$alkoxy, hydroxyl, C(O)OH, —C(O)OC$_{1-6}$alkyl, —O—C$_{3-6}$cycloalkyl, —O-heterocycle, —O-heteroaryl, —O-phenyl, —NR'R", —NR'—S(O)$_w$—C$_{1-3}$alkyl, —O—Si(R''')$_3$, S(O)$_w$ —NR'R", and —S(O)w—C$_{1-3}$alkyl;

w is 0, 1 or 2;

R$_{hh}$ is selected for each occurrence from the group consisting of H, C$_{1-6}$alkyl, and C$_{3-6}$cycloalkyl;

R' and R" are selected for each occurrence from the group consisting of H, C$_{1-6}$alkyl and C$_{3-6}$cycloalkyl; and R''' is selected for each occurrence from C$_{1-6}$alkyl.

In some embodiments, L$_1$ is C$_{1-3}$alkylene or C$_{3-5}$cycloalkylene (e.g., C$_4$ cycloalkylene), or C$_{3-6}$cycloalkylene-C$_{1-4}$alkylene. In other embodiments, L$_1$ is C$_{1-3}$alkylene-NR$_{hh}$—S(O)$_w$—, or —C$_{1-3}$alkylene-S(O)$_w$—NR$_{hh}$—.

In some embodiments, R$_{31}$ is H or F.

In some embodiments, R$_{22}$ is selected independently for each occurrence from H and CH$_3$.

In certain embodiments, a disclosed compound may be represented by:

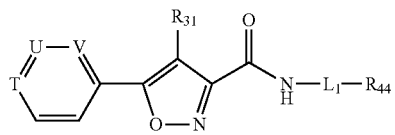

wherein one of T, U, and V is N and the other two of T, U, and V are CH.

In certain other embodiments, a disclosed compound may be represented by:

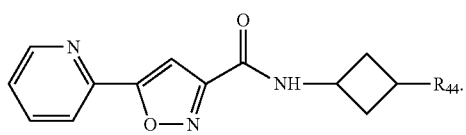

In some embodiments, R$_{44}$ is a 5-membered heteroaryl having two or three nitrogens. In other embodiments, R$_{44}$ is a 5 membered heteroaryl having two nitrogens and additional heteroatom selected from O or S. In certain of these embodiments, R$_{44}$ is substituted on a free carbon by a substituent selected from the group consisting of: a methyl substituted by one, two or three substituents each selected from halogen, hydroxyl, methoxy and ethoxy, ethyl substituted by one, two or three substituents each selected from halogen, hydroxyl, methoxy and ethoxy, propyl substituted by one, two or three substituents each selected from halogen, hydroxyl, methoxy and ethoxy), isopropyl substituted by one, two or three substituents each selected from halogen, hydroxyl, methoxy and ethoxy, n-butyl substituted by one, two or three substituents each selected from halogen, hydroxyl, methoxy and ethoxy, t-butyl substituted by one, two or three substituents each selected from halogen, hydroxyl, methoxy and ethoxy, s-butyl substituted by one, two or three substituents each selected from halogen, hydroxyl, methoxy and ethoxy and isobutyl substituted by one, two or three substituents each selected from halogen, hydroxyl, methoxy and ethoxy.

For example, R$_{44}$ can be selected from the group consisting of:

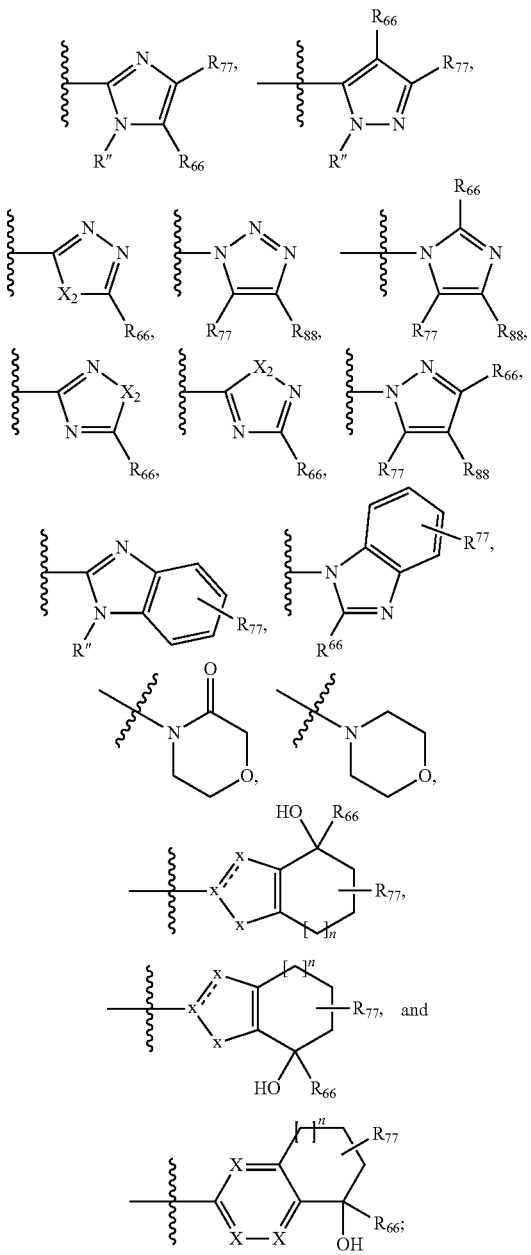

wherein X independently for each occurrence is selected from the group consisting of O, S, NR$_{hh}$, C, C(R$_{88}$), and C(R$_{88}$)(R$_{99}$); X$_2$ independently for each occurrence is selected from the group consisting of O, S and NR$_{hh}$; R" is H or C$_{1-4}$alkyl, each R$_{66}$, R$_{77}$, R$_{88}$ and R$_{99}$ is independently selected for each occurrence from H and R$_{gg}$, and n is 0, 1, 2, or 3.

In certain embodiments, $R_{44}$ is represented by:

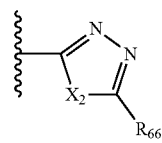

wherein $R_{66}$ is selected from the group consisting of: a methyl substituted by one, two or three substituents each selected from halogen, hydroxyl, methoxy and ethoxy, ethyl substituted by one, two or three substituents each selected from halogen, hydroxyl, methoxy and ethoxy, propyl substituted by one, two or three substituents each selected from halogen, hydroxyl, methoxy and ethoxy), isopropyl substituted by one, two or three substituents each selected from halogen, hydroxyl, methoxy and ethoxy, n-butyl substituted by one, two or three substituents each selected from halogen, hydroxyl, methoxy and ethoxy, t-butyl substituted by one, two or three substituents each selected from halogen, hydroxyl, methoxy and ethoxy, s-butyl substituted by one, two or three substituents each selected from halogen, hydroxyl, methoxy and ethoxy, and isobutyl substituted by one, two or three substituents each selected from halogen, hydroxyl, methoxy and ethoxy.

In certain embodiments, each of $R_{66}$, $R_{77}$ and $R_{88}$ is selected from the group consisting of H, halogen, methyl (optionally substituted by one, two or three substituents each selected from halogen, hydroxyl, methoxy and ethoxy), ethyl (optionally substituted by one, two or three substituents each selected from halogen, hydroxyl, methoxy and ethoxy), propyl (optionally substituted by one, two or three substituents each selected from halogen, hydroxyl, methoxy and ethoxy), isopropyl (optionally substituted by one, two or three substituents each selected from halogen, hydroxyl, methoxy and ethoxy), n-butyl (optionally substituted by one, two or three substituents each selected from halogen, hydroxyl, methoxy and ethoxy), t-butyl (optionally substituted by one, two or three substituents each selected from halogen, hydroxyl, methoxy and ethoxy), s-butyl (optionally substituted by one, two or three substituents each selected from halogen, hydroxyl, methoxy and ethoxy) and isobutyl (optionally substituted by one, two or three substituents each selected from halogen, hydroxyl, methoxy and ethoxy).

In certain embodiments, $R_{44}$ can be selected from the group consisting of tetrahydropyranyl, thiadiazolyl, tetrahydrofuranyl, and morpholinyl. In certain embodiments, $R_{44}$ can be a monocyclic heteroaryl containing one, two or three ring nitrogen atoms. In certain embodiments, $R_{4a}$ can be selected from the group consisting of furanyl, pyridinyl, pyrazinyl, pyrazolyl, imidazolyl, isoxazolyl, triazolyl, thiazolyl, oxadiazolyl, thiadiazolyl, thienyl, piperazinyl, and benzimidazolyl, each optionally substituted.

Also contemplated herein are pharmaceutical compositions that include a disclosed compound such as those compounds having Formula (IV) or (V) and a pharmaceutically acceptable carrier or excipient. In certain embodiments, the compositions can include at least one additional CFTR modulator as described anywhere herein or at least two additional CFTR modulators, each independently as described anywhere herein.

It is to be understood that the specific embodiments described herein can be taken in combination with other specific embodiments delineated herein. For example, as discussed above, in some embodiments, $X_3$ is S, and in some embodiments described above, $R_{44}$ is an optionally substituted imidazolyl or pyrazolyl. The disclosure thus encompasses compound of Formula (IV), wherein $X_3$ is S, and in some embodiments described above, $R_{44}$ is an optionally substituted imidazolyl or pyrazolyl.

The features and other details of the disclosure will now be more particularly described. Before further description of the present disclosure, certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

It will be appreciated that the description of the present invention herein should be construed in congruity with the laws and principals of chemical bonding.

The term "alkyl", as used herein, unless otherwise indicated, refers to both branched and straight-chain saturated aliphatic hydrocarbon groups having the specified number of carbon atoms; for example, "$C_1$-$C_{10}$ alkyl" denotes alkyl having 1 to 10 carbon atoms, and straight or branched hydrocarbons of 1-6, 1-4, or 1-3 carbon atoms, referred to herein as $C_{1-6}$alkyl, $C_{1-4}$alkyl, and $C_{1-3}$alkyl, respectively. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

The term, "alkenyl", as used herein, refers to both straight and branched-chain moieties having the specified number of carbon atoms and having at least one carbon-carbon double bond. Exemplary alkenyl groups include, but are not limited to, a straight or branched group of 2-6 or 3-4 carbon atoms, referred to herein as $C_{2-6}$alkenyl, and $C_{3-4}$alkenyl, respectively. Exemplary alkenyl groups include, but are not limited to, vinyl, allyl, butenyl, pentenyl, etc.

The term, "alkynyl", as used herein, refers to both straight and branched-chain moieties having the specified number or carbon atoms and having at least one carbon-carbon triple bond.

The term "cycloalkyl," as used herein, refers to saturated cyclic alkyl moieties having 3 or more carbon atoms, for example, 3-10, 3-6, or 4-6 carbons, referred to herein as $C_{3-10}$cycloalkyl, $C_{3-6}$cycloalkyl or $C_{4-6}$cycloalkyl, respectively for example. Examples of cycloalkyl include, but are not limited to, cyclopropyl, cyclobutyl, cyclopentyl, cyclohexyl, cycloheptyl and adamantyl.

The term "cycloalkenyl," as used herein, refers to cyclic alkenyl moieties having 3 or more carbon atoms.

The term "cycloalkynyl," as used herein, refers to cyclic alkynyl moieties having 5 or more carbon atoms.

"Alkylene" means a straight or branched, saturated aliphatic divalent radical having the number of carbons indicated. "Cycloalkylene" refers to a divalent radical of carbocyclic saturated hydrocarbon group having the number of carbons indicated.

The term "alkoxy" as used herein refers to a straight or branched alkyl group attached to oxygen (alkyl-O—). Exemplary alkoxy groups include, but are not limited to, alkoxy groups of 1-6 or 2-6 carbon atoms, referred to herein as $C_{1-6}$alkoxy, and $C_{2-6}$alkoxy, respectively. Exemplary alkoxy groups include, but are not limited to methoxy, ethoxy, isopropoxy, etc.

The term "heterocyclic" or "heterocycle" encompasses heterocycloalkyl, heterocycloalkenyl, heterobicycloalkyl, heterobicycloalkenyl, heteropolycycloalkyl, heteropolycycloalkenyl, and the like unless indicated otherwise. Heterocycloalkyl refers to cycloalkyl groups containing one or more heteroatoms (O, S, or N) within the ring. Heterocycloalkenyl as used herein refers to cycloalkenyl groups containing one or more heteroatoms (O, S or N) within the ring. Heterobicycloalkyl refers to bicycloalkyl groups containing one or more heteroatoms (O, S or N) within a ring. Heterobicycloalkenyl as used herein refers to bicycloalkenyl groups containing one or more heteroatoms (O, S or N) within a ring. A heterocycle can refer to, for example, a saturated or partially unsaturated 4- to 12 or 4-10-membered ring structure, including bridged or fused rings, and whose ring structures include one to three heteroatoms, such as nitrogen, oxygen, and sulfur. Where possible, heterocyclyl rings may be linked to the adjacent radical through carbon or nitrogen. Examples of heterocyclyl groups include, but are not limited to, pyrrolidine, piperidine, morpholine, thiomorpholine, piperazine, oxetane, azetidine, tetrahydrofuran or dihydrofuran etc.

Cycloalkyl, cycloalkenyl, and heterocyclic groups also include groups similar to those described above for each of these respective categories, but which are substituted with one or more oxo moieties.

The term "aryl", as used herein, refers to mono- or polycyclic aromatic carbocyclic ring systems. A polycyclic aryl is a polycyclic ring system that comprises at least one aromatic ring. Polycyclic aryls can comprise fused rings, covalently attached rings or a combination thereof. The term "aryl" embraces aromatic radicals, such as, phenyl, naphthyl, indenyl, tetrahydronaphthyl, and indanyl. An aryl group may be substituted or unsubstituted. In some embodiments, the aryl is a $C_4$-$C_{10}$ aryl. Examples of optionally substituted aryl are phenyl, substituted phenyl, naphthyl and substituted naphthyl.

The term "heteroaryl", as used herein, refers to aromatic carbocyclic groups containing one or more heteroatoms (O, S, or N) within a ring. A heteroaryl group, unless indicated otherwise, can be monocyclic or polycyclic. A heteroaryl group may additionally be substituted or unsubstituted. The heteroaryl groups of this disclosure can also include ring systems substituted with one or more oxo moieties. A polycyclic heteroaryl can comprise fused rings, covalently attached rings or a combination thereof. A polycyclic heteroaryl is a polycyclic ring system that comprises at least one aromatic ring containing one or more heteroatoms within a ring. Examples of heteroaryl groups include, but are not limited to, pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, triazinyl, isoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, thiazolopyridinyl, oxazolopyridinyl and azaindolyl. The foregoing heteroaryl groups may be C-attached or heteroatom-attached (where such is possible). For instance, a group derived from pyrrole may be pyrrol-1-yl (N-attached) or pyrrol-3-yl (C-attached). In some embodiments, the heteroaryl is 4- to 12-membered heteroaryl. In yet other embodiments, the heteroaryl is a mono or bicyclic 4- to 10-membered heteroaryl.

The term "substituted" refers to substitution by independent replacement of one, two, or three or more of the hydrogen atoms with substituents including, but not limited to, and unless indicated otherwise, —$C_1$-$C_{12}$ alkyl, —$C_2$-$C_{12}$ alkenyl, —$C_2$-$C_{12}$ alkynyl, —$C_3$-$C_{12}$ cycloalkyl, —$C_3$-$C_{12}$ cycloalkenyl, $C_3$-$C_{12}$ cycloalkynyl, -heterocyclic, —F, —Cl, —Br, —I, —OH, —$NO_2$, —$N_3$, —CN, —$NH_2$, oxo, thioxo, —$NHR_x$, —$NR_xR_x$, dialkylamino, -diarylamino, -diheteroarylamino, —$OR_x$, —$C(O)R_y$, —$C(O)C(O)R_y$, —$OCO_2R_y$, —$OC(O)R_y$, $OC(O)C(O)R_y$, —$NHC(O)R_y$, —$NHCO_2R_y$, —$NHC(O)C(O)R_y$, $NHC(S)NH_2$, —NHC(S) $NHR_x$, —$NHC(NH)NH_2$, —$NHC(NH)NHR_x$, —NHC(NH) $R_x$, —$C(NH)NHR_x$, and (C=$NR_x$)$R_y$; —$NR_xC(O)R_x$, —$NR_xC(O)N(R_x)_2$, —$NR_xCO_2R_y$, —$NR_xC(O)C(O)R_y$, —$NR_xC(S)NH_2$, —$NR_xC(S)NHR_x$, —$NR_xC(NH)NH_2$, —$NR_xC(NH)NHR_x$, —$NR_xC(NH)R_x$, —C(NRx)$NHR_x$—S (O)$R_y$, —$NHSO_2R_x$, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, -polyalkoxyalkyl, -polyalkoxy, -methoxymethoxy, -methoxyethoxy, —SH, —S—$R_x$, or -methylthiomethyl, wherein $R_x$ is selected from the group consisting of hydrogen, —$C_1$-$C_{12}$ alkyl, —$C_2$-$C_{12}$ alkenyl, —$C_2$-$C_{12}$ alkynyl, —$C_3$-$C_{12}$ cycloalkyl, -aryl, -heteroaryl and -heterocyclic and —$R_y$ is selected from the group consisting of hydrogen, —$C_1$-$C_{12}$ alkyl, —$C_2$-$C_{12}$ alkenyl, —$C_2$-$C_{12}$ alkynyl, —$C_3$-$C_{12}$ cycloalkyl, -aryl, -heteroaryl, -heterocyclic, —$NH_2$, —NH—$C_1$-$C_{12}$ alkyl, —NH—$C_2$-$C_{12}$ alkenyl, —NH—$C_2$-$C_{12}$-alkynyl, —NH—$C_3$-$C_{12}$ cycloalkyl, —NH-aryl, —NH-heteroaryl and —NH-heterocyclic. It is understood that the aryls, heteroaryls, alkyls, and the like can be further substituted.

The terms "halo" or "halogen" as used herein refer to F, Cl, Br, or I.

The term "haloalkyl" as used herein refers to an alkyl group having 1 to (2n+1) substituent(s) independently selected from F, Cl, Br or I, where n is the maximum number of carbon atoms in the alkyl group. It will be understood that haloalkyl is a specific example of an optionally substituted alkyl.

The terms "hydroxy" and "hydroxyl" as used herein refers to the radical —OH.

As will be understood by the skilled artisan, "H" is the symbol for hydrogen, "N" is the symbol for nitrogen, "S" is the symbol for sulfur, and "O" is the symbol for oxygen. "Me" is an abbreviation for methyl.

The compounds of the disclosure may contain one or more chiral centers and, therefore, exist as stereoisomers. The term "stereoisomers" when used herein consist of all enantiomers or diastereomers. These compounds may be designated by the symbols "(+)," "(−)," "R" or "S," depending on the configuration of substituents around the stereogenic carbon atom, but the skilled artisan will recognize that a structure may denote a chiral center implicitly. The present disclosure encompasses various stereoisomers of these compounds and mixtures thereof. Mixtures of enantiomers or diastereomers may be designated "(±)" in nomenclature, but the skilled artisan will recognize that a structure may denote a chiral center implicitly.

The compounds of the disclosure may contain one or more double bonds and, therefore, exist as geometric isomers resulting from the arrangement of substituents around a carbon-carbon double bond. The symbol ══ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond.

Compounds of the disclosure may contain a carbocyclic or heterocyclic ring and therefore, exist as geometric isomers resulting from the arrangement of substituents around the ring. The arrangement of substituents around a carbocyclic or heterocyclic ring are designated as being in the "Z" or "E" configuration wherein the terms "Z" and "E" are used in accordance with IUPAC standards. Unless otherwise specified, structures depicting carbocyclic or heterocyclic rings encompass both "Z" and "E" isomers. Substituents around a carbocyclic or heterocyclic rings may also be referred to as "cis" or "trans", where the term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

Individual enantiomers and diasteriomers of compounds of the present disclosure can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations, and may involve the use of chiral auxiliaries. For examples, see Carreira and Kvaerno, *Classics in Stereoselective Synthesis*, Wiley-VCH: Weinheim, 2009. Where a particular compound is described or depicted, it is intended to encompass that chemical structure as well as tautomers of that structure.

The term "enantiomerically pure" means a stereomerically pure composition of a compound. For example, a stereochemically pure composition is a composition that is free or substantially free of other stereoisomers of that compound. In another example, for a compound having one chiral center, an enantiomerically pure composition of the compound is free or substantially free of the other enantiomer. In yet another example, for a compound having two chiral centers, an enantiomerically pure composition is free or substantially free of the other diastereomers.

Where a particular stereochemistry is described or depicted it is intended to mean that a particular enantiomer is present in excess relative to the other enantiomer. A compound has an R-configuration at a specific position when it is present in excess compared to the compound having an S-configuration at that position. A compound has an S-configuration at a specific position when it is present in excess compared to the compound having an R-configuration at that position.

The compounds disclosed herein can exist in solvated as well as unsolvated forms with pharmaceutically acceptable solvents such as water, ethanol, and the like, and it is intended that the disclosure embrace both solvated and unsolvated forms. In one embodiment, the compound is amorphous. In one embodiment, the compound is a single polymorph. In another embodiment, the compound is a mixture of polymorphs. In another embodiment, the compound is in a crystalline form.

The disclosure also embraces isotopically labeled compounds of the disclosure which are identical to those recited herein, except that one or more atoms are replaced by an atom having an atomic mass or mass number different from the atomic mass or mass number usually found in nature. Examples of isotopes that can be incorporated into compounds of the disclosure include isotopes of hydrogen, carbon, nitrogen, oxygen, phosphorus, sulfur, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. For example, a compound of the disclosure may have one or more H atom replaced with deuterium.

Certain isotopically-labeled disclosed compounds (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labeled compounds of the disclosure can generally be prepared by following procedures analogous to those disclosed in the examples herein by substituting an isotopically labeled reagent for a non-isotopically labeled reagent.

The disclosure additionally encompasses embodiments wherein one or more of the nitrogen atoms in a disclosed compound are oxidized to N-oxide.

Representative synthetic routes that can be used to prepare the compounds disclosed herein are provide throughout the Examples section. As will be understood by the skilled artisan, diastereomers can be separated from the reaction mixture using column chromatography.

Compounds of the disclosure can also be prepared using methods described in the literature, including, but not limited to, *J. Med. Chem.* 2011, 54(13), 4350-64; *Russian Journal of Organic Chemistry*, 2011, 47(8), 1199-1203; U.S. Patent Application Publication No. 2009/0036451 A1; WO2008/046072 A2, and U.S. Pat. No. 4,336,264, the contents of each of which are expressly incorporated by reference herein.

As discussed above, the invention encompasses to a method of enhancing (e.g., increasing) CFTR activity in a subject (e.g., a subject suffering from any one or more of the conditions described herein) comprising administering a compound of the invention in an effective amount. The invention also encompasses a method of treating a patient suffering from a condition associated with CFTR activity comprising administering to said patient an effective amount of a compound described herein. In certain embodiments, the disease is cystic fibrosis.

"Treating" or "treatment" includes preventing or delaying the onset of the symptoms, complications, or biochemical indicia of a disease, alleviating or ameliorating the symptoms or arresting or inhibiting further development of the disease, condition, or disorder. A "subject" is an animal to be treated or in need of treatment. A "patient" is a human subject in need of treatment.

An "effective amount" refers to that amount of an agent that is sufficient to achieve a desired and/or recited effect. In the context of a method of treatment, an "effective amount" of the therapeutic agent that is sufficient to ameliorate of one or more symptoms of a disorder and/or prevent advancement of a disorder, cause regression of the disorder and/or to achieve a desired effect.

The term "modulating" encompasses increasing, enhancing, inhibiting, decreasing, suppressing, and the like. The terms "increasing" and "enhancing" mean to cause a net gain by either direct or indirect means. As used herein, the terms "inhibiting" and "decreasing" encompass causing a net decrease by either direct or indirect means.

In some examples, CFTR activity is enhanced after administration of a compound described herein when there is an increase in the CFTR activity as compared to that in the absence of the administration of the compound. CFTR activity encompasses, for example, chloride channel activity of the CFTR, and/or other ion transport activity (for example, $HCO_3^-$ transport). In certain of these embodiments, the activity of one or more (e.g., one or two) mutant CFTRs (e.g., ΔF508, S549N, G542X, G551D, R117H, N1303K, W1282X, R553X, 621+1G>T, 1717-1G>A, 3849+10kbC>T, 2789+5G>A, 3120+1G>A, I507del, R1162X, 1898+1G>A, 3659delC, G85E, D1152H, R560T, R347P, 2184insA, A455E, R334W, Q493X, and 2184delA CFTR) is enhanced (e.g., increased). Contemplated patients may have a CFTR mutation(s) from one or more classes, such as without limitation, Class I CFTR mutations, Class II CFTR mutations, Class III CFTR mutations, Class IV CFTR mutations, Class V CFTR mutations, and Class VI mutations. Contemplated subject (e.g., human subject) CFTR genotypes include, without limitation, homozygote mutations (e.g., ΔF508/ΔF508 and R117H/R117H) and compound heterozygote mutations (e.g., ΔF508/G551D; ΔF508/A455E; ΔF508/G542X; Δ508F/W1204X; R553X/W1316X; W1282X/N1303K, 591Δ18/E831X, F508del/R117H/N1303K/3849+10kbC>T; Δ303K/384; and DF508/G178R).

In certain embodiments, the mutation is a Class I mutation, e.g., a G542X; a Class II/I mutation, e.g., a ΔF508/G542X compound heterozygous mutation. In other embodiments, the mutation is a Class III mutation, e.g., a G551D; a Class II/Class III mutation, e.g., a ΔF508/G551D compound heterozygous mutation. In still other embodiments, the mutation is a Class V mutation, e.g., a A455E; Class II/Class V mutation, e.g., a ΔF508/A455E compound heterozygous mutation. Of the more than 1000 known mutations of the CFTR gene, ΔF508 is the most prevalent mutation of CFTR which results in misfolding of the protein and impaired trafficking from the endoplasmic reticulum to the apical membrane (Dormer et al. (2001). *J Cell Sci* 114, 4073-4081; http://www.genet.sickkids.on.ca/app). In certain embodiments, ΔF508 CFTR activity is enhanced (e.g., increased). In certain embodiments, ΔF508 CFTR activity and/or G542X CFTR activity and/or G551D CFTR activity and/or A455E CFTR activity is enhanced (e.g., increased). An enhancement of CFTR activity can be measured, for example, using literature described methods, including for example, Ussing chamber assays, patch clamp assays, and hBE Ieq assay (Devor et al. (2000), Am J Physiol Cell Physiol 279(2): C461-79; Dousmanis et al. (2002), J Gen Physiol 119(6): 545-59; Bruscia et al. (2005), PNAS 103(8): 2965-2971).

As discussed above, the disclosure also encompasses a method of treating cystic fibrosis. The present invention can also be used to treat other conditions associated with CFTR activity, including conditions associated with deficient CFTR activity.

In some embodiments, the disclosure is directed to a method of treating a condition associated with deficient or decreased CFTR activity comprising administering an effective amount of a compound of Formula (IV) or (V) that enhances CFTR activity. Non-limiting examples of conditions associated with deficient CFTR activity are cystic fibrosis, congenital bilateral absence of vas deferens (CBAVD), acute, recurrent, or chronic pancreatitis, disseminated bronchiectasis, asthma, allergic pulmonary aspergillosis, smoking-related lung diseases, such as chronic obstructive pulmonary disease (COPD), chronic sinusitis, dry eye disease, protein C deficiency, Aβ-lipoproteinemia, lysosomal storage disease, type 1 chylomicronemia, mild pulmonary disease, lipid processing deficiencies, type 1 hereditary angioedema, coagulation-fibrinolyis, hereditary hemochromatosis, CFTR-related metabolic syndrome, chronic bronchitis, constipation, pancreatic insufficiency, hereditary emphysema, and Sjogren's syndrome.

In some embodiments, disclosed methods of treatment further comprise administering an additional therapeutic agent. For example, in an embodiment, provided herein is a method of administering a disclosed compound and at least one additional therapeutic agent. In certain aspects, the disclosure is directed to a method comprising administering a disclosed compound, and at least two additional therapeutic agents. Additional therapeutic agents include, for example, mucolytic agents, bronchodilators, antibiotics, anti-infective agents, anti-inflammatory agents, ion channel modulating agents, therapeutic agents used in gene therapy, CFTR correctors, and CFTR potentiators, or other agents that modulates CFTR activity. In some embodiments, at least one additional therapeutic agent is selected from the group consisting of a CFTR corrector and a CFTR potentiator. Non-limiting examples of CFTR correctors and potentiators include VX-770 (Ivacaftor), VX-809 (3-(6-(1-(2,2-difluorobenzo[d][1,3]dioxol-5-yl)cyclopropanecarboxamido)-3-methylpyridin-2-yl)benzoic acid, VX-661 (1-(2,2-difluoro-1,3-benzodioxol-5-yl)-N-[1-[(2R)-2,3-dihydroxypropyl]-6-fluoro-2-(2-hydroxy-1,1-dimethylethyl)-1H-indol-5-yl]-cyclopropanecarboxamide), VX-983, VX-152, VX-440, and Ataluren (PTC124) (3-[5-(2-fluorophenyl)-1,2,4-oxadiazol-3-yl]benzoic acid), FDL169, GLPG1837/ABBV-974 (for example, a CFTR potentiator), GLPG 2665, GLPG2222 (for example, a corrector); and compounds described in, e.g., WO2014/144860 and 2014/176553, hereby incorporated by reference. Non-limiting examples of modulators include QBW-251, QR-010, NB-124, and compounds described in, e.g., WO2014/045283; WO2014/081821, WO2014/081820, WO2014/152213; WO2014/160440, WO2014/160478, US2014027933; WO2014/0228376, WO2013/038390, WO2011/113894, WO2013/038386; and WO2014/180562, of which the disclosed modulators in those publications are contemplated as an additional therapeutic agents and incorporated by reference. Non-limiting examples of anti-inflammatory agents include N6022 (3-(5-(4-(1H-imidazol-1-yl)phenyl)-1-(4-carbamoyl-2-methylphenyl)-$^1$H-pyrrol-2-yl) propanoic acid), CTX-4430, N1861, N1785, and N91115.

In some embodiments, the methods described herein can further include administering an additional therapeutic agent or administering at least two additional CFTR therapeutic agents. In some embodiments, the methods described herein can further include administering an additional CFTR modulator or administering at least two additional CFTR modulators. In certain embodiments, at least one CFTR modulator is a CFTR corrector (e.g., VX-809, VX-661, VX-983, VX-152, VX-440, GLPG2222 and GLPG2665) or potentiator (e.g., ivacaftor, genistein and GLPG1837). In certain of these embodiments, one of the at least two additional therapeutic agents is a CFTR corrector (e.g., VX-809, VX-661, VX-983, VX-152, and VX-440) and the other is a CFTR potentiator (e.g., ivacaftor and genistein). In certain of these embodiments, one of the at least two additional therapeutic agents is a CFTR corrector (e.g., GLPG2222 or GLPG2665) and the other is a CFTR potentiator (e.g., GLPG1837). In certain of these embodiments, one of the at least two additional therapeutic agents is a CFTR corrector (e.g., VX-809 or VX-661) and the other is a CFTR potentiator (e.g., ivacaftor). In certain of these embodiments, at least one CFTR modulator is an agent that enhances readthrough of stop codons (e.g., NB124 or ataluren).

Accordingly, in another aspect, this disclosure provides a method of treating a condition associated with deficient or decreased CFTR activity (e.g., cystic fibrosis), which includes administering to a subject in need thereof (e.g., a human patient in need thereof) an effective amount of a disclosed compound and at least one or two additional CFTR therapeutic agent(s) (e.g., at least one or two additional CFTR therapeutic agents, e.g., in which one of the at least one or two additional therapeutic agents is optionally a CFTR corrector or modulator (e.g., VX-809, VX-661, VX-983, VX-152, VX-440, GLPG2222, GLPG2665, NB124, ataluren) and/or the other is a CFTR potentiator (e.g., ivacaftor, genistein, and GLPG1837); e.g., one of the at least two additional therapeutic agents is GLPG2222 or GLPG2665, and the other is GLPG1837; or one of the at least two additional therapeutic agents is VX-809 or VX-661, and the other is a ivacaftor). In certain embodiments, the subject's CFTR genotype includes, without limitation, one or more Class I CFTR mutations, one or more Class II CFTR mutations, one or more Class III CFTR mutations, one or more Class IV CFTR mutations, or one or more Class V CFTR mutations, or one or more Class VI CFTR mutations. In certain embodiments, the subject's CFTR genotype includes, without limitation, one or more homozygote mutations (e.g., ΔF508/ΔF508 or R117H/R117H) and/or one or more compound heterozygote mutations (e.g., ΔF508/G551D; ΔF508/A455E; ΔF508/G542X; Δ508F/W1204X; R553X/W1316X; W1282X/N1303K; F508del/R117H; N1303K/3849+10kbC>T; ΔF508/R334W; DF508/G178R. and 591Δ18/E831X). In certain embodiments, the subject's CFTR genotype includes a Class I mutation, e.g., a G542X Class I mutation, e.g., a ΔF508/G542X compound heterozygous mutation. In other embodiments, the subject's CFTR genotype includes a Class III mutation, e.g., a G551D Class III mutation, e.g., a ΔF508/G551D compound heterozygous mutation. In still other embodiments, the subject's CFTR genotype includes a Class V mutation, e.g., a A455E Class V mutation, e.g., a ΔF508/A455E compound heterozygous mutation. In certain embodiments, ΔF508 CFTR activity and/or G542X CFTR activity and/or G551D CFTR activity and/or A455E activity is enhanced (e.g., increased). In certain embodiments, the enhancement in activity (e.g., increase in activity) provided by the combination of the disclosed compound and one or two additional therapeutic agents is greater than additive when compared to the enhancement in activity provided by each therapeutic component individually.

| Class | Effect on CFTR protein | Example of mutation |
|---|---|---|
| I | Shortened protein | W1282X Instead of inserting the amino acid tryptophan (W), the protein sequence is prematurely stopped (indicated by an X). |
| II | Protein fails to reach cell membrane | ΔF508 A phenylalanine amino acid (F) is deleted |
| III | Channel cannot be regulated properly | G551D A "missense" mutation: instead of a glycine amino acid (G), aspartate (D) is added |
| IV | Reduced chloride conductance | R117H Missense |
| V | Reduced due to incorrect splicing of gene | 3120 + 1G > A Splice-site mutation in gene intron 16 |
| VI | Reduced due to protein instability | N287Y a A –> T at 991 |

| Genotype | Description | Possible Symptoms |
|---|---|---|
| Δ508F/Δ508F | homozygote | Severe lung disease, pancreatic insufficient |
| R117H/R117H | homozygote | Congenital bilateral absence of the vas deferens, No lung or pancreas disease, |
| WT/Δ508F | heterozygote | Unaffected |
| WT/3120 + 1 G > A | heterozygote | Unaffected |
| Δ508F/W1204X | compound heterozygote | No lung disease, pancreatic insufficient |
| R553X and W1316X | compound heterozygote | Mild lung disease, pancreatic insufficient |
| 591Δ18/E831X | compound heterozygote | No lung or pancreas disease, nasal polyps |

For example, provided herein is a method of treating a patient having one or more of the following mutations in the CFTR gene: G1244E, G1349D, G178R, G551S, S1251N, S1255P, S549N, S549R, G970R, or R11.7H, and/or e.g., a patient with one or two copies of the F508del mutation, or one copy of the ΔF508 mutation and a second mutation that results in a gating effect in the CFTR protein (e.g., a patient that is heterozygous for ΔF508 and G551D mutation), a patient with one copy of the ΔF508 mutation and a second mutation that results in residual CFTR activity, or a patient with one copy of the ΔF508 mutation and a second mutation that results in residual CFTR activity, comprising administering an effective amount of a disclosed compound. As described herein, such exemplary methods (e.g., of a patient having one or mutations such as those described above) may include, for example, administering to such patient a combination therapy, e.g., administering (simultaneously or sequentially) an effective amount of ivacaftor to said patient and an effective amount of disclosed compound that may act as an amplifier. Such administration may result, for example, in increased chloride transport in human bronchial epithelial cells with e.g., one or two copies of mutations, e.g, ΔF508 mutation, as compared to administration of ivacaftor alone. Another combination therapy that includes a disclosed compound may also include an effective amount of a readthrough agent (e.g., ataluren, NB124) and an effect amount of disclosed compound that may act as an amplifier.

The phrase "combination therapy," as used herein, refers to an embodiment where a patient is co-administered a disclosed compound, a CFTR potentiator agent (e.g., ivacaftor) and optionally, one or more CFTR corrector agent(s) (e.g, VX-661 and/or lumacaftor) as part of a specific treatment regimen intended to provide the beneficial effect from the co-action of these therapeutic agents. For example, a beneficial effect of a combination may include, but is not limited to, pharmacokinetic or pharmacodynamic co-action resulting from the combination of therapeutic agents. For example, administration of a disclosed compound with ivacaftor alone or with a CFTR corrector agent (e.g., lumacaftor or VX-661) may result in a level of function (e.g., as measured by chloride activity in HBE cells or patients that have a ΔF508 mutation, that achieves clinical improvement (or better) as compared to the chloride activity level in cells or patients with a G551D mutation receiving ivacaftor alone, or ivacaftor and a corrector agent (lumacaftor or VX-661); or for example, administration of a disclosed compound with ivacaftor alone or ivacaftor with a CFTR corrector agent (e.g., lumacaftor or VX-661) may result in a level of function (e.g., as measured by chloride activity in HBE cells or patients that have a A455E mutation) that achieves clinical improvement (or better) as compared to the chloride activity level at e.g., 50% or more of wild type cells; or upon administration of a disclosed compound and ivacaftor to a patient (e.g. having a G551D class III mutation) may show e.g., about two times or more improved activity of ivacaftor as compared to administration of ivacaftor alone. Administration of disclosed therapeutic agents in combination typically is carried out over a defined time period (usually a day, days, weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single tablet or capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, inhalational routes, intravenous routes, intramuscular routes, and direct absorption through mucous membrane tissues. The therapeutic agents can be administered by the same route or by different routes. For example, a first therapeutic agent of the combination selected may be administered by intravenous injection or inhalation or nebulizer while the other therapeutic agents of the combination may be administered orally. Alternatively, for example, all therapeutic agents may be administered orally or all therapeutic agents may be administered by intravenous injection, inhalation or nebulization.

Combination therapy also can embrace the administration of the therapeutic agents as described above in further combination with other biologically active ingredients and non-drug therapies. Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by a day, days or even weeks.

The components of a disclosed combination may be administered to a patient simultaneously or sequentially. It will be appreciated that the components may be present in the same pharmaceutically acceptable carrier and, therefore, are administered simultaneously. Alternatively, the active ingredients may be present in separate pharmaceutical carriers, such as, conventional oral dosage forms, that can be administered either simultaneously or sequentially.

In a further aspect, a method of identifying a candidate agent that increases CFTR activity is provided, which includes: (i) contacting a cell that expresses a CFTR protein with the candidate agent and a disclosed compound; (ii) measuring the CFTR activity in the cell in the presence of the candidate agent and the disclosed compound; and (iii) comparing the CFTR activity to that in the absence of the test agent, wherein an increase in CFTR activity in the presence of the test agent indicates that the agent increases CFTR activity. In certain embodiments, the cell expresses a mutant CFTR protein. In certain embodiments, CFTR activity is measured by measuring chloride channel activity of the CFTR, and/or other ion transport activity. In certain of these embodiments, the method is high-throughput. In certain of these embodiments, the candidate agent is a CFTR corrector or a CFTR potentiator.

The term "pharmaceutically acceptable salt(s)" as used herein refers to salts of acidic or basic groups that may be present in a disclosed compounds used in disclosed compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts, particularly calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

Also included in the present disclosure are methods that include administering prodrugs of the compounds described herein, for example, prodrugs of a compound of Formula (IV) or (V), or a pharmaceutical composition thereof or method of use of the prodrug.

The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and or reductive metabolism) in various locations (such as in the intestinal lumen or upon transit of the intestine, blood or liver). Prodrugs are well known in the art (for example, see Rautio, Kumpulainen, et al, Nature Reviews Drug Discovery 2008, 7, 255). For example, if a compound of the disclosure or a pharmaceutically acceptable salt, hydrate or solvate of the compound contains a carboxylic acid functional group, a prodrug can comprise an ester formed by the replacement of the hydrogen atom of the acid group with a group such as $(C_{1-8})$alkyl, $(C_{2-12})$alkylcarbonyloxymethyl, 1-(alkylcarbonyloxy)ethyl having from 4 to 9 carbon atoms, 1-methyl-1-(alkylcarbonyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_{1-2})$ alkylamino$(C_{2-3})$alkyl (such as β-dimethylaminoethyl), carbamoyl-$(C_{1-2})$alkyl, N,N-di$(C_{1-2})$ alkylcarbamoyl-$(C_{1-2})$alkyl and piperidino-, pyrrolidino- or morpholino$(C_{2-3})$alkyl.

Similarly, if a compound of the disclosure contains an alcohol functional group, a prodrug can be formed by the replacement of the hydrogen atom of the alcohol group with a group such as $(C_{1-6})$alkylcarbonyloxymethyl, 1-($(C_{1-6})$ alkylcarbonyloxy)ethyl, 1-methyl-1-($(C_{1-6})$alkylcarbonyloxy)ethyl $(C_{1-6})$alkoxycarbonyloxymethyl, N—$(C_{1-6})$ alkoxycarbonylaminomethyl, succinoyl, $(C_{1-6})$ alkylcarbonyl, α-amino$(C_{1-4})$alkylcarbonyl, arylalkylcarbonyl and α-aminoalkylcarbonyl, or α-aminoalkylcarbonyl-α-aminoalkylcarbonyl, where each α-aminoalkylcarbonyl group is independently selected from the naturally occurring L-amino acids, $P(O)(OH)_2$, —$P(O)(O(C_{1-6})$alkyl$)_2$ or glycosyl (the radical resulting from the removal of a hydroxyl group of the hemiacetal form of a carbohydrate).

If a compound of the disclosure incorporates an amine functional group, a prodrug can be formed, for example, by creation of an amide or carbamate, an N-alkylcarbonyloxyalkyl derivative, an (oxodioxolenyl)methyl derivative, an N-Mannich base, imine or enamine. In addition, a secondary amine can be metabolically cleaved to generate a bioactive primary amine, or a tertiary amine can metabolically cleaved to generate a bioactive primary or secondary amine. For examples, see Simplicio, et al., *Molecules* 2008, 13, 519 and references therein.

The disclosure additionally includes use of clathrates of the compounds described herein, pharmaceutical compositions comprising the clathrates, and methods of use of the clathrates. In some embodiments, the invention is directed to clathrates of a compound of Formula (IV) or (V), or a pharmaceutical composition thereof.

As discussed above, the disclosure includes administration of pharmaceutical compositions comprising a pharmaceutically acceptable carrier or excipient and a compound described herein. A disclosed compound, or a pharmaceutically acceptable salt, solvate, clathrate or prodrug thereof, can be administered in pharmaceutical compositions comprising a pharmaceutically acceptable carrier or excipient. The excipient can be chosen based on the expected route of administration of the composition in therapeutic applications. The route of administration of the composition depends on the condition to be treated. For example, intravenous injection may be preferred for treatment of a systemic disorder and oral administration may be preferred to treat a gastrointestinal disorder. The route of administration and the dosage of the composition to be administered can be determined by the skilled artisan without undue experimentation in conjunction with standard dose-response studies. Relevant circumstances to be considered in making those determinations include the condition or conditions to be treated, the choice of composition to be administered, the age, weight, and response of the individual patient, and the severity of the patient's symptoms. A pharmaceutical composition comprising a disclosed compound or a pharmaceutically acceptable salt, solvate, clathrate or prodrug, can be administered by a variety of routes including, but not limited to, parenteral, oral, pulmonary, ophthalmic, nasal, rectal, vaginal, aural, topical, buccal, transdermal, intravenous, intramuscular, subcutaneous, intradermal, intraocular, intracerebral, intralymphatic, intraarticular, intrathecal and intraperitoneal. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the pharmacologic agent or composition. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like. Pharmaceutical compositions can also include large, slowly metabolized macromolecules such as proteins, polysaccharides such as chitosan, polylactic acids, polyglycolic acids and copolymers (such as latex functionalized SEPHAROSE™, agarose, cellulose, and the like), polymeric amino acids, amino acid copolymers, and lipid aggregates (such as oil droplets or liposomes).

The compositions can be administered parenterally such as, for example, by intravenous, intramuscular, intrathecal or subcutaneous injection. Parenteral administration can be accomplished by incorporating a composition into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as, for example, benzyl alcohol or methyl parabens, antioxidants such as, for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

Injectable formulations can be prepared either as liquid solutions or suspensions; solid forms suitable for solution in, or suspension in, liquid vehicles prior to injection can also be prepared. The preparation also can also be emulsified or encapsulated in liposomes or micro particles such as polylactide, polyglycolide, or copolymer for enhanced adjuvant effect, as discussed above [Langer, *Science* 249: 1527, 1990 and Hanes, *Advanced Drug Delivery Reviews* 28: 97-119, 1997]. The compositions and pharmacologic agents described herein can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, transdermal applications and ocular delivery. For suppositories, binders and carriers include, for example, polyalkylene glycols or triglycerides; such suppositories can be formed from mixtures containing the active ingredient in the range of about 0.5% to about 10%, preferably about 1% to about 2%. Oral formulations include excipients, such as pharmaceutical grades of mannitol, lactose, starch, magnesium stearate, sodium saccharine, cellulose, and magnesium carbonate. Topical application can result in transdermal or intradermal delivery. Transdermal delivery can be achieved using a skin patch or using transferosomes. [Paul et al., *Eur. J. Immunol.* 25: 3521-24, 1995; Cevc et al., *Biochem. Biophys. Acta* 1368: 201-15, 1998].

For the purpose of oral therapeutic administration, the pharmaceutical compositions can be incorporated with excipients and used in the form of tablets, troches, capsules, elixirs, suspensions, syrups, wafers, chewing gums and the like. Tablets, pills, capsules, troches and the like may also contain binders, excipients, disintegrating agent, lubricants, glidants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and non-toxic in the amounts used. In another embodiment, the composition is administered as a tablet or a capsule.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor, and the like. For vaginal administration, a pharmaceutical composition may be presented as pessaries, tampons, creams, gels, pastes, foams or spray.

The pharmaceutical composition can also be administered by nasal administration. As used herein, nasally administering or nasal administration includes administering the composition to the mucus membranes of the nasal passage or nasal cavity of the patient. As used herein, pharmaceutical compositions for nasal administration of a composition include therapeutically effective amounts of the compounds prepared by well-known methods to be administered, for example, as a nasal spray, nasal drop, suspension, gel, ointment, cream or powder. Administration of the composition may also take place using a nasal tampon or nasal sponge.

For topical administration, suitable formulations may include biocompatible oil, wax, gel, powder, polymer, or other liquid or solid carriers. Such formulations may be administered by applying directly to affected tissues, for example, a liquid formulation to treat infection of conjunctival tissue can be administered dropwise to the subject's eye, or a cream formulation can be administered to the skin.

Rectal administration includes administering the pharmaceutical compositions into the rectum or large intestine. This can be accomplished using suppositories or enemas. Suppository formulations can easily be made by methods known in the art. For example, suppository formulations can be prepared by heating glycerin to about 120° C., dissolving the pharmaceutical composition in the glycerin, mixing the heated glycerin after which purified water may be added, and pouring the hot mixture into a suppository mold.

Transdermal administration includes percutaneous absorption of the composition through the skin. Transdermal formulations include patches, ointments, creams, gels, salves and the like.

In addition to the usual meaning of administering the formulations described herein to any part, tissue or organ whose primary function is gas exchange with the external environment, for purposes of the present disclosure, "pulmonary" will also mean to include a tissue or cavity that is contingent to the respiratory tract, in particular, the sinuses. For pulmonary administration, an aerosol formulation containing the active agent, a manual pump spray, nebulizer or pressurized metered-dose inhaler as well as dry powder formulations are contemplated. Suitable formulations of this type can also include other agents, such as antistatic agents, to maintain the disclosed compounds as effective aerosols.

A drug delivery device for delivering aerosols comprises a suitable aerosol canister with a metering valve containing a pharmaceutical aerosol formulation as described and an actuator housing adapted to hold the canister and allow for drug delivery. The canister in the drug delivery device has a head space representing greater than about 15% of the total volume of the canister. Often, the compound intended for pulmonary administration is dissolved, suspended or emulsified in a mixture of a solvent, surfactant and propellant. The mixture is maintained under pressure in a canister that has been sealed with a metering valve.

The disclosure also encompasses the treatment of a condition associated with a dysfunction in proteostasis in a subject comprising administering to said subject an effective amount of a disclosed compound that enhances, improves or restores proteostasis of a protein. Proteostasis refers to protein homeostasis. Dysfunction in protein homeostasis is a result of protein misfolding, protein aggregation, defective protein trafficking or protein degradation. For example, the invention encompasses administering a compound of Formula (IV) or (V) that corrects protein misfolding, reduces protein aggregation, corrects or restores protein trafficking and/or affects protein degradation for the treatment of a condition associated with a dysfunction in proteostasis. In some aspects of the invention, a compound of Formula (IV) or (V) that corrects protein misfolding and/or corrects or restores protein trafficking is administered. In cystic fibrosis, the mutated or defective enzyme is the cystic fibrosis transmembrane conductance regulator (CFTR). One of the most common mutations of this protein is ΔF508 which is a deletion (Δ) of three nucleotides resulting in a loss of the amino acid phenylalanine (F) at the 508th (508) position on the protein. As described above, mutated cystic fibrosis transmembrane conductance regulator exists in a misfolded state and is characterized by altered trafficking as compared to the wild type CFTR. Additional exemplary proteins of which there can be a dysfunction in proteostasis, for example that can exist in a misfolded state, include, but are not limited to, glucocerebrosidase, hexosamine A, aspartylglucsaminidase, α-galactosidase A, cysteine transporter, acid ceremidase, acid α-L-fucosidase, protective protein, cathepsin A, acid β-glucosidase, acid β-galactosidase, iduronate 2-sulfatase, α-L-iduronidase, galactocerebrosidase, acid α-mannosidase, acid β-mannosidase, arylsulfatase B, arylsulfatase A, N-acetylgalactosamine-6-sulfate sulfatase, acid β-galactosidase, N-acetylglucosamine-1-phosphotransferase, acid sphingmyelinase, NPC-1, acid α-glucosidase, β-hexosamine B, heparin N-sulfatase, α-N-acetylglucosaminidase, α-glucosaminide N-acetyltransferase, N-acetylglucosamine-6-sulfate sulfatase, α-N-acetylgalactosaminidase, α-neuramidase, β-glucuronidase, β-hexosamine A and acid lipase, polyglutamine, α-synuclein, TDP-43, superoxide dismutase (SOD), Aβ peptide, tau protein transthyretin and insulin. The compounds of Formula (IV) or (V) can be used to restore proteostasis (e.g., correct folding and/or alter trafficking) of the proteins described above.

Protein conformational diseases encompass gain of function disorders and loss of function disorders. In one embodiment, the protein conformational disease is a gain of function disorder. The terms "gain of function disorder," "gain of function disease," "gain of toxic function disorder" and "gain of toxic function disease" are used interchangeably herein. A gain of function disorder is a disease characterized by increased aggregation-associated proteotoxicity. In these diseases, aggregation exceeds clearance inside and/or outside of the cell. Gain of function diseases include, but are not limited to, neurodegenerative diseases associated with aggregation of polyglutamine, Lewy body diseases, amyotrophic lateral sclerosis, transthyretin-associated aggregation diseases, Alzheimer's disease, Machado-Joseph disease, cerebral B-amyloid angiopathy, retinal ganglion cell degeneration, tautopathies (progressive supranuclear palsy, corticobasal degeration, frontotemporal lobar degeneration), cerebral hemorrhage with amyloidosis, Alexander disease, Serpinopathies, familial amyloidotic neuropathy, senile systemic amyloidosis, ApoAI amyloidosis, ApoAII amyloidosis, ApoAIV amyloidosis, familial amyloidosis of the Finnish type, lysoyzme amyloidosis, fibrinogen amyloidosis, dialysis amyloidosis, inclusion body myositis/myopathy, cataracts, medullary thyroid carcinoma, cardiac atrial amyloidosis, pituitary prolactinoma, hereditary lattice corneal dystrophy, cutaneous lichen amyloidosis, corneal lactoferrin amyloidosis, corneal lactoferrin amyloidosis, pulmonary alveolar proteinosis, odontogenic tumor amyloid, seminal vesical amyloid, sickle cell disease, critical illness myopathy, von Hippel-Lindau disease, spinocerebellar ataxia 1, Angelman syndrome, giant axon neuropathy, inclusion body myopathy with Paget disease of bone, frontotemporal dementia (IBMPFD) and prion diseases. Neurodegenerative diseases associated with aggregation of polyglutamine include, but are not limited to, Huntington's disease, dentatorubral and pallidoluysian atrophy, several forms of spino-cerebellar ataxia, and spinal and bulbar muscular atrophy. Alzheimer's disease is characterized by the formation of two types of aggregates: extracellular aggregates of Aβ peptide and intracellular aggregates of the microtubule associated protein tau. Transthyretin-associated aggregation diseases include, for example, senile systemic amyloidoses and familial amyloidotic neuropathy. Lewy body diseases are characterized by an aggregation of α-synuclein protein and include, for example, Parkinson's disease, lewy body dementia (LBD) and multiple system atrophy (SMA). Prion diseases (also known as transmissible spongiform encephalopathies or TSEs) are characterized by aggregation of prion proteins. Exemplary human prion diseases are Creutzfeldt-Jakob Disease (CJD), Variant Creutzfeldt-Jakob Disease, Gerstmann-Straussler-Scheinker Syndrome, Fatal Familial Insomnia and Kuru. In another embodiment, the misfolded protein is alpha-1 anti-trypsin.

In a further embodiment, the protein conformation disease is a loss of function disorder. The terms "loss of function disease" and "loss of function disorder" are used interchangeably herein. Loss of function diseases are a group of diseases characterized by inefficient folding of a protein resulting in excessive degradation of the protein. Loss of function diseases include, for example, lysosomal storage diseases. Lysosomal storage diseases are a group of diseases characterized by a specific lysosomal enzyme deficiency which may occur in a variety of tissues, resulting in the build-up of molecules normally degraded by the deficient enzyme. The lysosomal enzyme deficiency can be in a lysosomal hydrolase or a protein involved in the lysosomal trafficking. Lysosomal storage diseases include, but are not limited to, aspartylglucosaminuria, Fabry's disease, Batten disease, Cystinosis, Farber, Fucosidosis, Galactasidosialidosis, Gaucher's disease (including Types 1, 2 and 3), Gm1 gangliosidosis, Hunter's disease, Hurler-Scheie's disease, Krabbe's disease, α-Mannosidosis, β-Mannosidosis, Maroteaux-Lamy's disease, Metachromatic Leukodystrophy, Morquio A syndrome, Morquio B syndrome, Mucolipidosis II, Mucolipidosis III, Neimann-Pick Disease (including Types A, B and C), Pompe's disease, Sandhoff disease, Sanfilippo syndrome (including Types A, B, C and D), Schindler disease, Schindler-Kanzaki disease, Sialidosis, Sly syndrome, Tay-Sach's disease and Wolman disease.

In another embodiment, the disease associated with a dysfunction in proteostasis is a cardiovascular disease. Cardiovascular diseases include, but are not limited to, coronary artery disease, myocardial infarction, stroke, restenosis and arteriosclerosis. Conditions associated with a dysfunction of proteostasis also include ischemic conditions, such as, ischemia/reperfusion injury, myocardial ischemia, stable angina, unstable angina, stroke, ischemic heart disease and cerebral ischemia.

In yet another embodiment, the disease associated with a dysfunction in proteostasis is diabetes and/or complications of diabetes, including, but not limited to, diabetic retinopathy, cardiomyopathy, neuropathy, nephropathy, and impaired wound healing.

In a further embodiment, the disease associated with a dysfunction in proteostasis is an ocular disease including, but not limited to, age-related macular degeneration (AMD), diabetic macular edema (DME), diabetic retinopathy, glaucoma, cataracts, retinitis pigmentosa (RP) and dry macular degeneration.

In yet additional embodiments, the method of the invention is directed to treating a disease associated with a dysfunction in proteostasis, wherein the disease affects the respiratory system or the pancreas. In certain additional embodiments, the methods of the invention encompass treating a condition selected from the group consisting of polyendocrinopathy/hyperinsulinemia, diabetes mellitus, Charcot-Marie Tooth syndrome, Pelizaeus-Merzbacher disease, and Gorham's Syndrome.

Additional conditions associated with a dysfunction of proteostasis include hemoglobinopathies, inflammatory diseases, intermediate filament diseases, drug-induced lung damage and hearing loss. The invention also encompasses methods for the treatment of hemoglobinopathies (such as sickle cell anemia), an inflammatory disease (such as inflammatory bowel disease, colitis, ankylosing spondylitis), intermediate filament diseases (such as non-alcoholic and alcoholic fatty liver disease) and drug induced lung damage (such as methotrexate-induced lung damage). The invention additionally encompasses methods for treating hearing loss, such as noise-induced hearing loss, aminoglycoside-induced hearing loss, and cisplatin-induced hearing loss.

Additional conditions include those associated with a defect in protein trafficking and that can be treated according to methods of the invention include: PGP mutations, hERG trafficking mutations, nephrongenic diabetes insipidus mutations in the arginine-vasopressin receptor 2, persistent hyperinsulinemic hypoglycemia of infancy (PHH1) mutations in the sulfonylurea receptor 1, and α1AT.

The invention is illustrated by the following examples which are not meant to be limiting in any way.

EXEMPLIFICATION

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials. At least some of the compounds identified as "intermediates" herein are contemplated as compounds of the invention.

The compounds in table 1 (values of R shown in Table 2) are prepared using the following procedure: EDC.HCl (1.98 mmol), HOBt.H2O (1.32 mmol) and amine (1.45 mmol) are added to a solution of 3-substituted isoxazole-5-carboxylic acid (1.32 mmol) in THF (10 mL) at room temperature. Reaction mixture is stirred for 15 h at room temperature and the reaction mixture is concentrated to dryness. The crude solid is extracted with EtOAc and washed with water. Combined organic layers are dried over Na₂SO₄ and concentrated till dryness. Crude compound is purified by Combiflash or chiral HPLC to give the amide.

TABLE 1

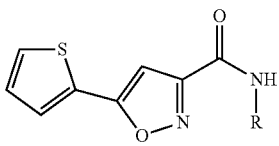

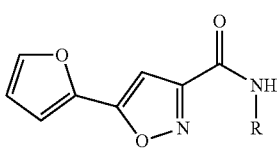

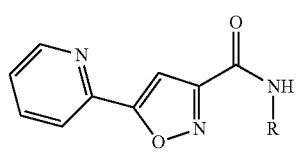

TABLE 2

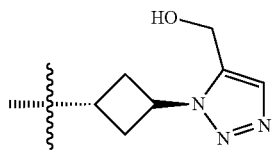

TABLE 2-continued

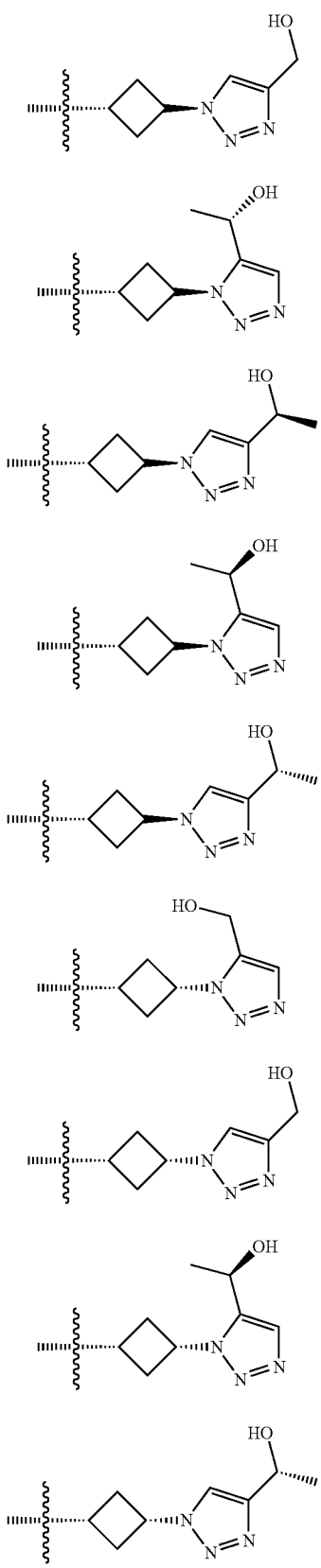

TABLE 2-continued
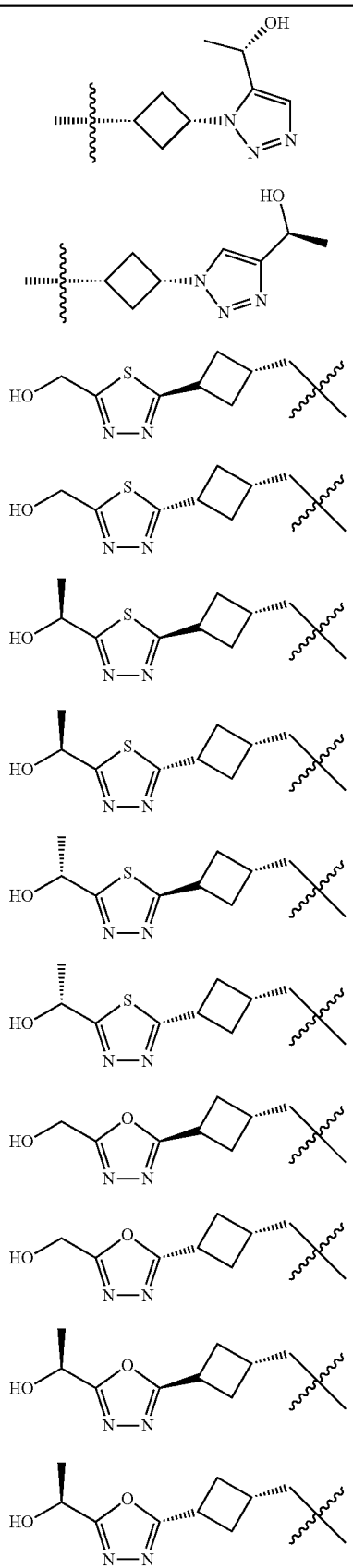
TABLE 2-continued
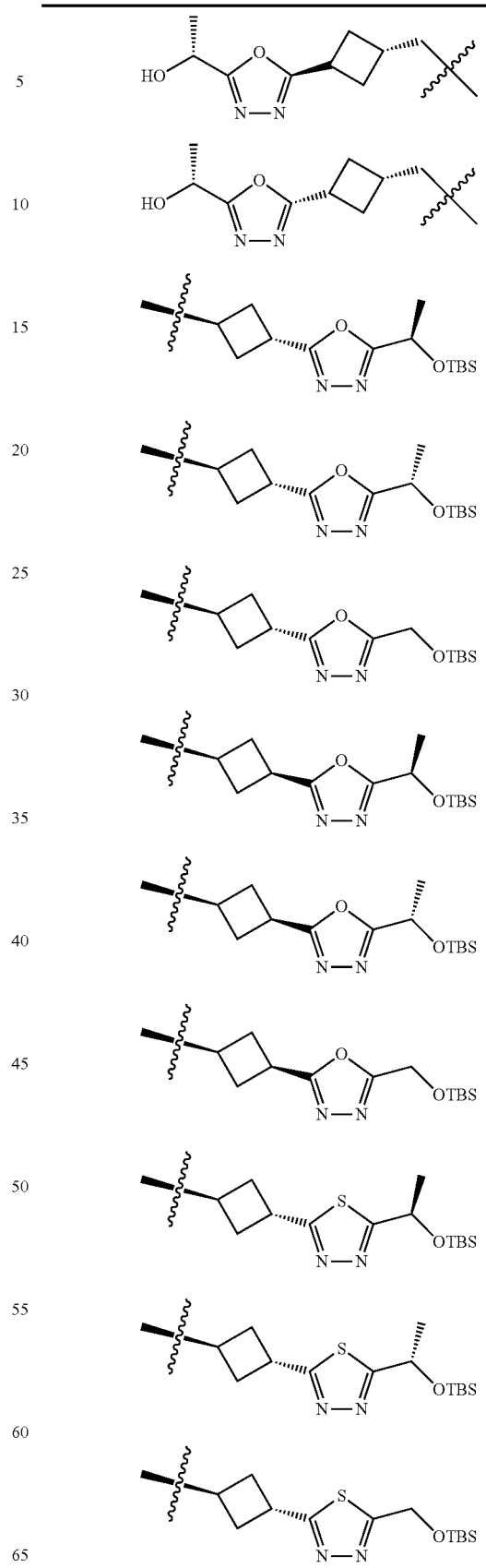

TABLE 2-continued
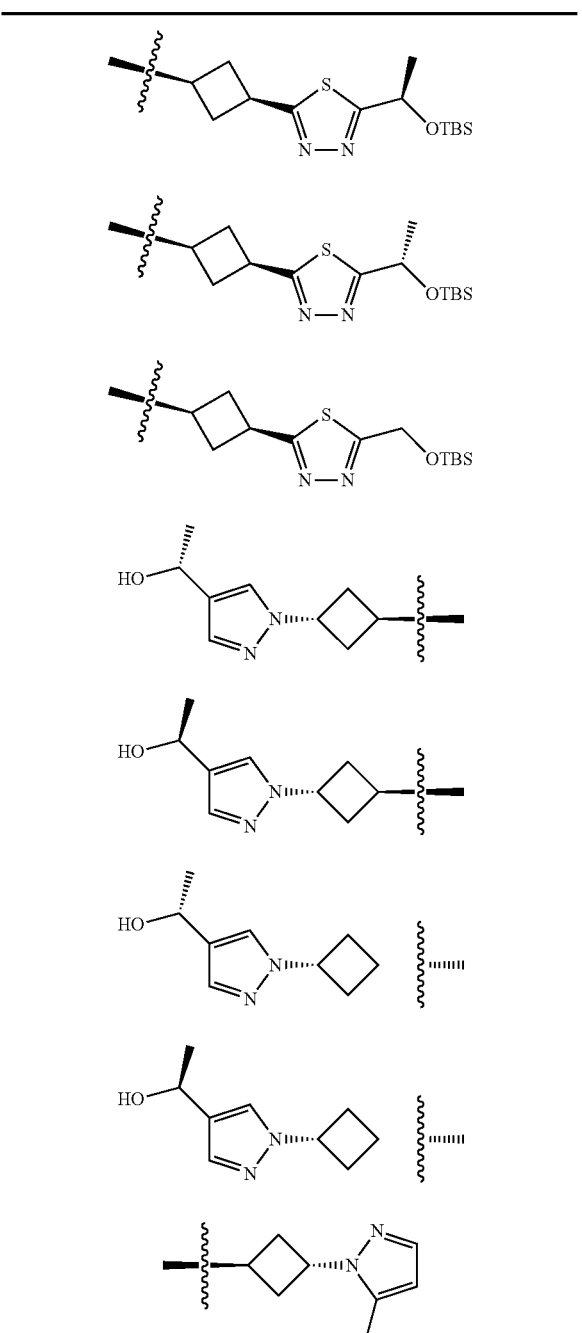
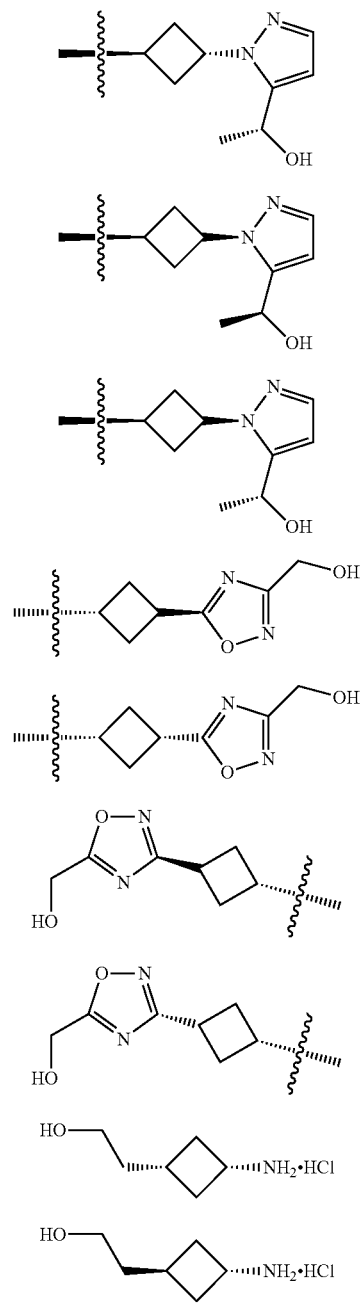
Amines 1 and 2: 1-(trans-3-aminocyclobutyl)-1H-1,2,3-triazol-4-yl)methanol hydrochloride and 1-(trans-3-aminocyclobutyl)-1H-1,2,3-triazol-5-yl)methanol hydrochloride
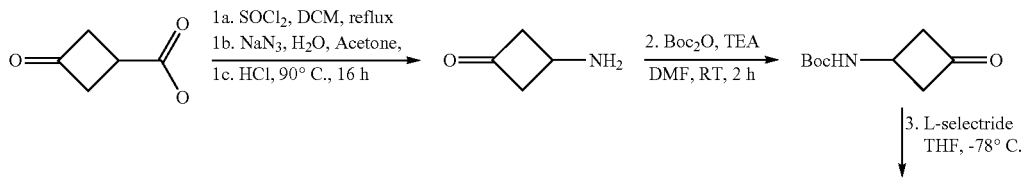

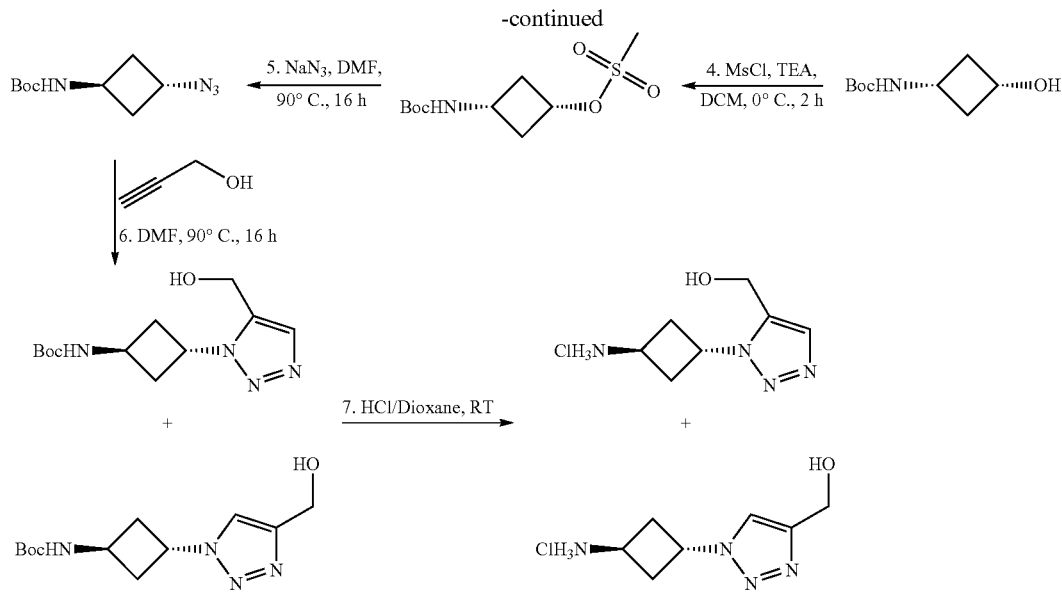

Step 1: 3-Amino-cyclobutan-1-one: SOCl$_2$ (15.6 g, 131.46 mmol) was added dropwise to an ice-cooled solution of 3-oxocyclobutane carboxylic acid (5.0 g, 43.82 mmol) in dry DCM (30 mL) and the reaction mixture was refluxed for 3 h. The reaction mixture was cooled to room temperature and the volatiles were removed under reduced pressure to get the crude compound which was azeotropically distilled with toluene (20 mL×2) to remove acidic traces. The crude compound was dissolved in dry acetone (15 mL) and to the resulting solution was added a solution of NaN$_3$ (5.69 g, 87.64 mmol) in water (20 mL) at 0° C. over 30 min. The reaction mixture was stirred for 1 h at 0° C. and crushed ice was added to the reaction mixture. The aq. phase was extracted with ether (3×50 mL), dried over sodium sulfate and concentrated to ~¼th volume. Then the reaction mixture was added to toluene (70 mL) and heated to 90° C., until evolution of N$_2$ ceased (~30 min). To the resulting reaction mixture was added 20% HCl (50 mL) at 0° C. and the reaction mixture was gently heated to 90° C. for 16 h. Organic layer was separated off and washed with water (50 mL). The aqueous layer was concentrated under vacuum to get the compound (5 g, crude) as a brown solid. $^1$H-NMR (400 MHz, CDCl$_3$) δ 8.75 (br, 3H), 3.92-3.86 (m obscured by solvent signal, 2H), 3.38-3.31 (m, 3H).

Step 2: tert-butyl (3-oxocyclobutyl) carbamate: TEA (29.72 g, 293.73 mmol) was added dropwise to a solution of 3-aminocyclobutan-1-one (5.0 g, 58.74 mmol) and Boc$_2$O (25.64 g, 117.49 mmol) in DMF (80 mL) and the reaction mixture was stirred at room temperature for 2 h. After complete consumption of starting material as indicated by TLC, the reaction mixture was diluted with water (100 mL) and extracted with diethyl ether (70 mL×6). Combined organic layer was washed with brine (100 mL×2) and dried over Na$_2$SO$_4$. The solvent was removed under reduced pressure to get the crude compound which was purified by silica gel (100-200) column chromatography using 30% ethyl acetate in n-hexane to afford the product (5.3 g, 65% after two steps) as an off-white solid. $^1$H-NMR (400 MHz, CDCl$_3$) δ 4.91 (br, 1H), 4.25 (br, 1H), 3.41-3.34 (m, 2H), 3.07-3.00 (m, 2H), 1.44 (s, 9H).

Step 3: tert-butyl cis-3-hydroxycyclobutyl)carbamate: a solution of L-Selectride (1M solution in THF) (8.053 mL, 8.05 mmol) was added dropwise over a period of 20 min to a solution of tert-butyl (3-oxocyclobutyl)carbamate (1.0 g, 5.40 mmol) in THF (25 mL) under N$_2$ atmosphere at −78° C. and the reaction mixture was stirred for 1 h at −78° C. To the resulting reaction mixture was added a solution of NaOH (3.25 g) in water (4 mL) over a period of 10 min followed by 30% aqueous H$_2$O$_2$ (3 mL) over a period of 20 min. The reaction mixture was allowed to warm to room temperature and diluted with ethyl acetate (100 mL). The organic layer was separated off and washed with 10% aq. Na$_2$SO$_3$ (40 mL) followed by brine (40 mL). The organic layer dried over Na$_2$SO$_4$ and concentrated under reduced pressure to get the crude compound which was further purified by neutral alumina column chromatography using 50% ethyl acetate in n-hexane as eluent to afford the desired compound. The compound was washed with n-hexane to get the product (0.750 g, 74%) as white solid. m. p. 119° C. (lit. value 117° C.). $^1$H NMR (400 MHz, CDCl$_3$) δ 4.63 (br, 1H), 4.03-3.96 (m, 1H), 3.66-3.64 (m, 1H), 2.76-2.72 (m, 2H), 1.91 (br, 1H), 1.79-1.76 (m, 2H), 1.42 (s, 9H).

Step 4: cis-3-((tert-butoxycarbonyl)amino)cyclobutyl methanesulfonate: triethylamine (1.0 g, 9.93 mmol) was added to a cold (−10° C.) solution of tert-butyl (cis-3-hydroxycyclobutyl)carbamate (0.62 g, 3.31 mmol) in DCM (30 mL) followed by dropwise addition of methanesulfonyl chloride (0.45 g, 3.97 mmol) and the reaction mixture was stirred at −10° C. for 2 h. The reaction mixture was diluted with DCM (100 mL) and washed with water (5 mL) followed by dilute citric acid (30 mL) and brine (30 mL). The organic layer was dried over Na$_2$SO$_4$, concentrated under reduced pressure to get the product (0.800 g, crude) as white solid which was used as such in next step without further purification. $^1$H NMR (400 MHz, CDCl$_3$) δ 4.73-4.66 (m, 2H), 3.85-3.80 (m, 1H), 2.98 (s, 3H), 2.93-2.86 (m, 2H), 2.20-2.13 (m, 2H), 1.42 (s, 9H).

Step 5: tert-butyl (trans-3-azidocyclobutyl) carbamate: NaN$_3$ (0.49 g, 7.54 mmol) was added to a solution of cis-3-((tert-butoxycarbonyl) amino) cyclobutyl methanesulfonate (0.8 g, 3.01 mmol) in dry DMF (20 mL) and the mixture was heated at 85° C. for 16 h. The reaction mixture was diluted with water (40 mL) and the aqueous phase was extracted with ethyl acetate (50 mL×3). Combined organic layer was washed with brine (50 mL×4) and dried over Na$_2$SO$_4$. The solvent was removed under reduced pressure to get the crude product (0.73 g) as an off-white solid. Although DMF was present in the crude according to $^1$H-NMR, it was used as such in the next step without further purification.

Step 6: tert-butyl trans-3-(5-(hydroxymethyl)-1H-1,2,3-triazol-1-yl)cyclobutyl)carbamate and tert-butyl (trans-3-(4-(hydroxymethyl)-1H-1,2,3-triazol-1-yl)cyclobutyl)carbamate: a solution of tert-butyl trans-3-azidocyclobutyl)carbamate (0.98 g, 4.62 mmol) in DMF (5 mL) and propargyl alcohol (1.29 g, 23.08 mmol) was heated at 100° C. in a sealed tube for 16 h. The mixture was diluted with water (30 mL) and the aqueous phase was extracted with ethyl acetate (25 mL×7). Combined organic layer was dried over Na$_2$SO$_4$ and solvent was removed under reduced pressure to get the crude compound which was further purified by neutral alumina column chromatography using 80% ethyl acetate in n-hexane as eluent to afford a fraction of 5-isomer enriched (4/1 ratio of isomers 5/4, 0.350 g, 28%) as an off-white solid and elution with 5% methanol in DCM afforded a fraction of 4-isomer enriched (1/3 ratio of isomers 5/4, 0.52 g, 42%) as an off-white solid. LC-MS: (M+H)$^+$= 269.1

Amines 3 and 4: (S)-1-(1-(trans-3-aminocyclobutyl)-1H-1,2,3-triazol-4-yl)ethan-1-ol and (S)-1-(1-(trans-3-aminocyclobutyl)-1H-1,2,3-triazol-4-yl)ethan-1-ol were prepared by the procedure described for amines 3 and 4 using (S)-3-butyn-2-ol.

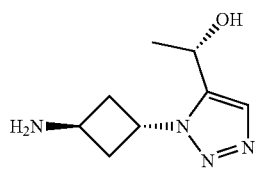

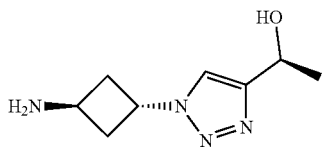

Amines 5 and 6: (R)-1-(1-(trans-3-aminocyclobutyl)-1H-1,2,3-triazol-4-yl)ethan-1-ol and (R)-1-(1-(trans-3-aminocyclobutyl)-1H-1,2,3-triazol-4-yl)ethan-1-ol were prepared by the procedure described for amines 3 and 4 using (S)-3-butyn-2-ol.

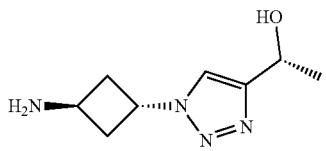

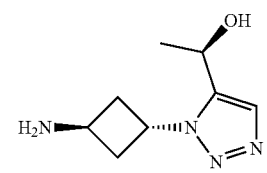

Amines 7 and 8: 1-(cis-3-aminocyclobutyl)-1H-1,2,3-triazol-5-yl)methanol hydrochloride and 1-(cis-3-aminocyclobutyl)-1H-1,2,3-triazol-5-yl)methanol hydrochloride

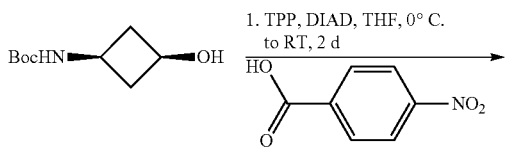

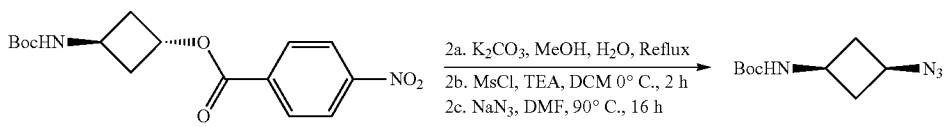

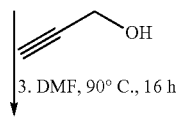

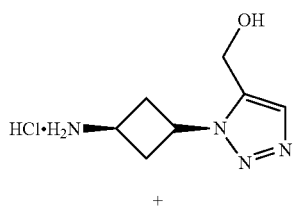

-continued

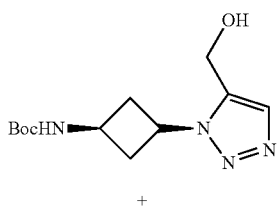

4a. HCl/Dioxane/RT

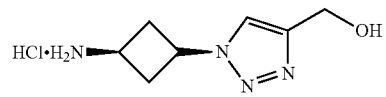

Step 1: trans-3-((tert-butoxycarbonyl)amino)cyclobutyl 4-nitrobenzoate: To an ice-cooled solution of tert-butyl (cis-3-hydroxycyclobutyl)carbamate (1.5 g, 80.11 mmol) and 4-nitrobenzoic acid (1.47 g, 88.12 mmol) in dry THF (60 mL) was added triphenyl phosphine (3.15 g, 12.01 mmol) followed by dropwise addition of DIAD (8.09 g, 40.05 mmol) and the reaction mixture was stirred at room temperature for 2 days. Solvent was removed under reduced pressure to get the crude compound which was purified by silica gel (100-200 mesh) column chromatography. Elution with 50% ethyl acetate in n-hexane followed by washing with diethyl ether (4 mL×2) gave the product (2.3 g, 85%) as a white solid. $^1$H-NMR (400 MHz, CDCl$_3$) δ 8.29-8.27 (q, 2H, J=8.92 Hz), 8.21-8.19 (q, 2H, J=8.92 Hz), 5.37-5.32 (m, 1H), 4.77 (br, 1H), 4.41-4.38 (m, 1H), 2.64-2.58 (m, 2H), 2.47-2.40 (m, 2H), 1.44 (s, 9H); LC-MS: (M+H)$^+$=336.8

Step 2a: Trans-tert-butyl-3-hydroxycyclobutyl carbamate: trans-3-((tert-butoxycarbonyl) amino) cyclobutyl 4-nitrobenzoate was added (2.3 g, 68.38 mmol) to a suspension of K$_2$CO$_3$ (1.41 g, 10.25 mmol) in MeOH (50 mL) and water (10 mL) and the reaction mixture was heated to reflux for 2 h. The reaction mixture was cooled and filtered through celite bed. Filtrate was concentrated under reduced pressure to get the crude product (4.2 g, crude) as an off-white solid which was used as such without further purification.

Step 2b: trans-3-((tert-butoxycarbonyl)amino)cyclobutyl methanesulfonate: triethyl amine (6.8 g, 67.29 mmol) was added to a suspension of trans-tert-butyl-3-hydroxycyclobutyl carbamate (4.2 g, 22.43 mmol) in DCM (100 mL) followed by dropwise addition of methanesulfonyl chloride (3.08 g, 26.91 mmol) at −10° C. and the reaction mixture was stirred at −10 OC for 2 h. The reaction mixture was diluted with DCM (100 mL) and washed with water (50 mL) followed by brine (30 mL). The organic layer was dried over sodium sulfate and concentrated under reduced pressure to obtain the crude product (3.4 g, crude) as a yellow solid which was used as such in next step without purification.

Step 2c: cis-tert-butyl (3-azidocyclobutyl)carbamate: sodium azide (2.08 g, 32.035 mmol) was added to a solution of trans-3-((tert-butoxycarbonyl)amino)cyclobutyl methanesulfonate (3.4 g, 12.81 mmol) in dry DMF (20 mL) at room temperature and the reaction mixture was heated at 85° C. for 16 h. The crude reaction mixture was diluted with water (50 mL) and the aqueous phase was extracted with ethyl acetate (50 mL×3). The combined organic layer was washed with brine (50 mL×4) and dried over Na$_2$SO$_4$. The solvent was removed under reduced pressure to give the crude compound which was purified by neutral alumina column chromatography using 10% MeOH in DCM as eluent to afford the product (1.0 g, 68% after two steps) as a white solid. $^1$H NMR (400 MHz, CDCl$_3$) δ 4.66 (br, 1H), 3.86-3.84 (m, 1H), 3.57-3.53 (m, 1H), 2.76-2.69 (m, 2H), 1.92-1.85 (m, 2H), 1.42 (s, 9H).

Step 3: cis-[3-(4/5-Hydroxymethyl-[1,2,3]triazol-1-yl)-cyclobutyl]-carbamic acid tert-butyl ester: a mixture of cis-tert-butyl (3-azidocyclobutyl)carbamate (0.280 g, 1.32 mmol) and propargyl alcohol (0.221 g, 3.96 mmol) in DMF (5 mL) was heated at 100° C. in a sealed tube for 16 h. Solvent was removed under reduced pressure to get crude compound which was purified by neutral alumina column chromatography using 5% methanol in DCM as eluent to obtain a mixture of 4/5 regioisomers (0.30 g, 84%) as a viscous oil. This mixture was used as such in the next reaction. LC-MS: (M+H)$^+$=269.0.

Step 4a: (1-cis-3-aminocyclobutyl)-1H-1,2,3-triazol-4/5-yl)methanol (A): A suspension of cis-[3-(4/5-hydroxymethyl-[1,2,3]triazol-1-yl)-cyclobutyl]-carbamic acid tert-butyl ester (0.30 g, 1.12 mmol) in 4M HCl in dioxane (30 mL) was stirred at room temperature for 24 h. Volatiles were removed under reduced pressure to get the crude mixture (0.30 g, crude) as off-white solid which was used as such in next step without further purification. As per $^1$H-NMR, it is a 50:50 mixture of two regioisomers.

Amines 9 and 10: (S)-1-(1-(cis-3-aminocyclobutyl)-1H-1,2,3-triazol-4-yl)ethan-1-ol and (S)-1-(1-(cis-3-aminocyclobutyl)-1H-1,2,3-triazol-4-yl)ethan-1-ol were prepared by the procedure described for amines 3 and 4 using (S)-3-butyn-2-ol.

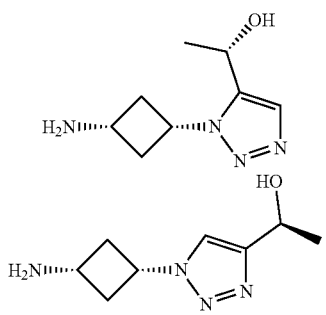

Amines 11 and 12: (R)-1-(1-(cis-3-aminocyclobutyl)-1H-1,2,3-triazol-4-yl)ethan-1-ol and (R)-1-(1-(cis-3-aminocyclobutyl)-1H-1,2,3-triazol-4-yl)ethan-1-ol were prepared by the procedure described for amines 3 and 4 using (R)-3-butyn-2-ol.

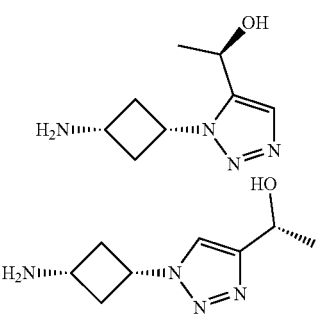

Amines 13 and 14: (5-(3-cis-(aminomethyl)cyclobutyl)-1,3,4-thiadiazol-2-yl)methanol hydrochloride and (5-(3-trans-(aminomethyl)cyclobutyl)-1,3,4-thiadiazol-2-yl)methanol hydrochloride

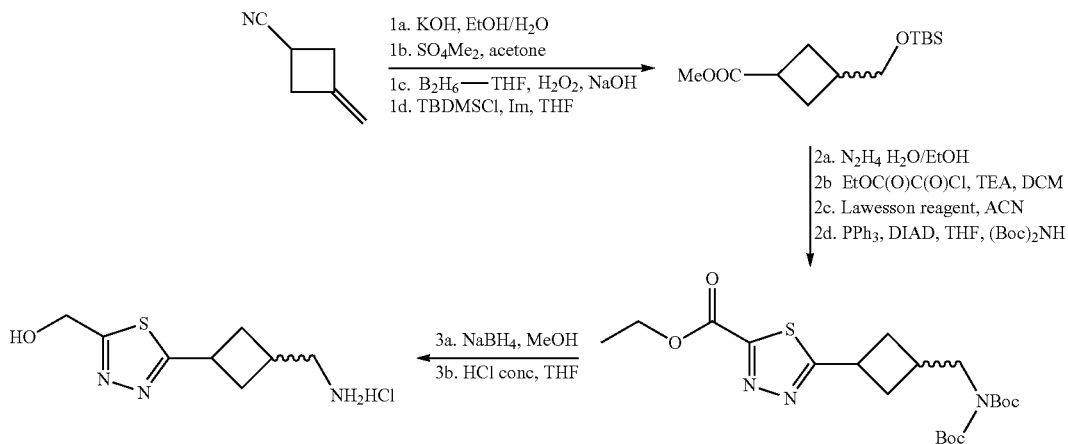

Step 1a: 3-methylenecyclobutane-1-carboxylic acid: To a solution of 3-methylidenecyclobutane-1-carbonitrile (6 g, 64.43 mmol, 1.00 eq.) in H₂O/EtOH (40/40 mL), was added potassium hydroxide (15 g, 267.33 mmol, 4.00 eq.) in several batches at 105° C. in 30 min. The resulting solution was stirred for 2 hours at 105° C. The resulting solution was diluted with water (200 mL) and the pH was adjusted to 2 with conc. hydrogen chloride aqueous (12 M). The resulting solution was extracted with ethyl acetate (2×200 mL) and the organic layers combined. The resulting mixture was washed with brine (2×200 mL), dried over anhydrous sodium sulfate and concentrated under vacuum to give of 3-methylidenecyclobutane-1-carboxylic acid as yellow oil (7 g, 97%).

Step 1b: methyl 3-methylenecyclobutane-1-carboxylate: potassium carbonate (61.5 g, 444.98 mmol, 2.00 eq.) and dimethyl sulfate (33 g, 261.63 mmol, 1.20 eq.) were added to a solution of 3-methylidenecyclobutane-1-carboxylic acid (25 g, 222.96 mmol, 1.00 eq.) in acetone (300 mL). The resulting solution was stirred for 2 hours at 60° C. The resulting solution was diluted with water (700 mL) and then extracted with ethyl acetate (2×500 mL) and the organic layers combined. The resulting mixture was washed with brine (2×500 mL), dried over anhydrous sodium sulfate and concentrated under vacuum. This resulted in 30 g (crude) of methyl 3-methylidenecyclobutane-1-carboxylate as yellow oil.

Step 1C: methyl 3-(hydroxymethyl)cyclobutane-1-carboxylate: a solution of borane-THF (56 mL, 0.80 eq.) was added dropwise over 30 min to a cold (−10° C.) solution of methyl 3-methylidenecyclobutane-1-carboxylate (10 g, 79.27 mmol, 1.00 eq.) in THF (100 mL). The resulting solution was stirred for 3 hours at 25° C. The mixture was cooled to −10° C. and methanol (20 mL) was added slowly and the mixture was stirred for 30 min at 25° C. The reaction mixture was cooled to −10° C. and H₂O₂ (9 g, 79.41 mmol, 1.00 eq., 30%) was added dropwise (5 min) followed by dropwise addition of sodium hydroxide aqueous (12.5 mL) at −10° C. The resulting solution was stirred for 3 hours at 25° C. The reaction was then quenched by the addition of Na₂SO₃ aqueous. The resulting solution was diluted with water (300 mL) and then extracted with ethyl acetate (2×300 mL) and the organic layers combined. The resulting mixture was washed with brine (2×300 mL), dried over anhydrous sodium sulfate and concentrated under vacuum to give methyl 3-(hydroxymethyl)cyclobutane-1-carboxylate as colorless oil (6.6 g, 58%).

Step 1d: methyl 3-(((tert-butyldimethylsilyl)oxy)methyl)cyclobutane-1-carboxylate: imidazole (5.4 g, 79.41 mmol, 2.00 eq.) and TBDMSCl (9.4 g, 62.38 mmol, 1.50 eq.) were added to a solution of methyl 3-(hydroxymethyl)cyclobutane-1-carboxylate (5 g, 34.68 mmol, 1.00 eq.) in tetrahydrofuran (100 mL) and the resulting solution was stirred for 16 hours at 40° C. The mixture was diluted with water (200 mL) and then extracted with ethyl acetate (3×200 mL) and the organic layers were combined. The resulting mixture was washed with brine (2×300 mL), dried over anhydrous sodium sulfate and concentrated under vacuum to give methyl 3-[[(tert-butyldimethylsilyl)oxy]methyl]cyclobutane-1-carboxylate as a yellow oil (8 g, 89%).

Step 2a: 3-(((tert-butyldimethylsilyl)oxy)methyl)cyclobutane-1-carbohydrazide: hydrazine hydrate (20 mL) was added to a solution of methyl 3-[[(tert-butyldimethylsilyl)oxy]methyl]cyclobutane-1-carboxylate (8 g, 30.96 mmol, 1.00 eq.) in ethanol (100 mL). The resulting solution was stirred for 2 hours at 80° C., diluted with water (300 mL) and then extracted with ethyl acetate (2×300 mL) and the organic layers combined. The resulting mixture was washed with brine (2×200 mL), dried over anhydrous sodium sulfate and concentrated under vacuum to give 3-[[(tert-butyldimethylsilyl)oxy]methyl]cyclobutane-1-carbohydrazide (7.5 g, 94%) as a yellow oil. LC-MS: 259.1 [M+H]⁺.

Step 2b: ethyl 2-(2-(3-(((tert-butyldimethylsilyl)oxy)methyl)cyclobutane-1-carbonyl)hydrazinyl)-2-oxoacetate: ethyl 2-chloro-2-oxoacetate (8.87 g, 64.97 mmol, 1.10 eq.)

was added dropwise (in 10 min) to a solution of 3-[[(tert-butyldimethylsilyl)oxy]methyl]cyclobutane-1-carbohydrazide (15.3 g, 59.20 mmol, 1.00 eq.) and TEA (9 g, 88.94 mmol, 1.50 eq.) in dichloromethane (200 mL) at 0° C. The resulting solution was stirred for 1 hour at 25° C., diluted with dichloromethane (300 mL) and it was then washed with brine (2×200 mL), dried over anhydrous sodium sulfate and concentrated under vacuum. The residue was applied onto a silica gel column and eluted with petroleum ether/ethyl acetate (2:1) to give ethyl 2-[(3-[[(tert-butyldimethylsilyl)oxy]methyl]cyclobutyl)formohydrazido]-2-oxoacetate (15 g, 71%) as a yellow oil. LC-MS: 359.0 [M+H]⁺.

Step 2c: ethyl 5-(3-(hydroxymethyl)cyclobutyl)-1,3,4-thiadiazole-2-carboxylate: Lawesson reagent (17 g, 42.03 mmol, 1.00 eq.) was added to a solution of ethyl 2-(2-(3-(((tert-butyldimethylsilyl)oxy)methyl)cyclobutane-1-carbonyl)hydrazinyl)-2-oxoacetate (15 g, 41.84 mmol, 1.00 eq.) in ACN (150 mL) and the solution was stirred for 2 hours at 50° C. The reaction mixture was diluted with water (300 mL), extracted with ethyl acetate (2×300 mL) and the organic layers combined. The resulting mixture was washed with brine (2×200 mL), dried over anhydrous sodium sulfate and concentrated under vacuum. The residue was purified by silica gel column with ethyl acetate/petroleum ether (2:1) followed by purification by Flash-Prep-HPLC using the following conditions (IntelFlash-1): Column, C18 silica gel; mobile phase, X:H₂O Y:ACN=95/5 increasing to X:H₂O Y:ACN=40/60 within 50 min; Detector, UV 254 nm. This resulted in 3.4 g (34%) of ethyl 5-[3-(hydroxymethyl)cyclobutyl]-1,3,4-thiadiazole-2-carboxylate as a yellow oil. LC-MS: 243.2 [M+H]⁺.

Step 2d: ethyl 5-(3-((bis((tert-butoxy)carbonyl)amino)methyl)cyclobutyl)-1,3,4-thiadiazole-2-carboxylate: To a sodium sulfate and concentrated under vacuum. The residue was purified by silica gel column using ethyl acetate/petroleum ether (1:5) to give the product (1.1 g, 33%) as a yellow solid. LC-MS: [M+H]⁺ 442.3

Step 3a: tert-butyl [3-[5-(hydroxymethyl)-1,3,4-thiadiazol-2-yl]cyclobutyl]methyl N-[(tert-butoxy)carbonyl]carbamate: NaBH₄ (310 mg, 8.19 mmol, 1.50 eq.) was added to a solution of ethyl-(3-((bis((tert-butoxy)carbonyl)amino)methyl)cyclobutyl)-1,3,4-thiadiazole-2-carboxylate (2.4 g, 5.42 mmol, 1.00 eq.) in methanol (50 mL), in portions at 0° C. in 10 min and the reaction mixture was then stirred for 1 hour at 25° C. The reaction was then quenched with water (200 mL). The resulting solution was extracted with ethyl acetate (2×200 mL) and the organic layers combined. The resulting mixture was washed with brine (2×200 mL), dried over anhydrous sodium sulfate and concentrated under vacuum to give the product (2 g, 92%) of as yellow oil. LC-MS: 400.0 [M+H]⁺.

Step 3b: (5-(3-(aminomethyl)cyclobutyl)-1,3,4-thiadiazol-2-yl)methanol hydrochloride: conc. hydrogen chloride aqueous (4 mL) was added to a solution of tert-butyl [3-[5-(hydroxymethyl)-1,3,4-thiadiazol-2-yl]cyclobutyl]methyl N-[(tert-butoxy)carbonyl]carbamate (2 g, 4.99 mmol, 1.00 eq.) in tetrahydrofuran (20 mL) and the solution was stirred for 16 hours at 25° C. The resulting mixture was concentrated under vacuum, the solid was washed with 20 mL of ethyl acetate to give the product (750 mg, 75%) as a yellow solid. LC-MS: 200.1 [M+H-HCl]⁺.

Amines 15 and 16: (S)-1-(5-(cis-3-(aminomethyl)cyclobutyl)-1,3,4-thiadiazol-2-yl)ethan-1-ol hydrochloride and (S)-1-(5-(trans-3-(aminomethyl)cyclobutyl)-1,3,4-thiadiazol-2-yl)ethan-1-ol hydrochloride

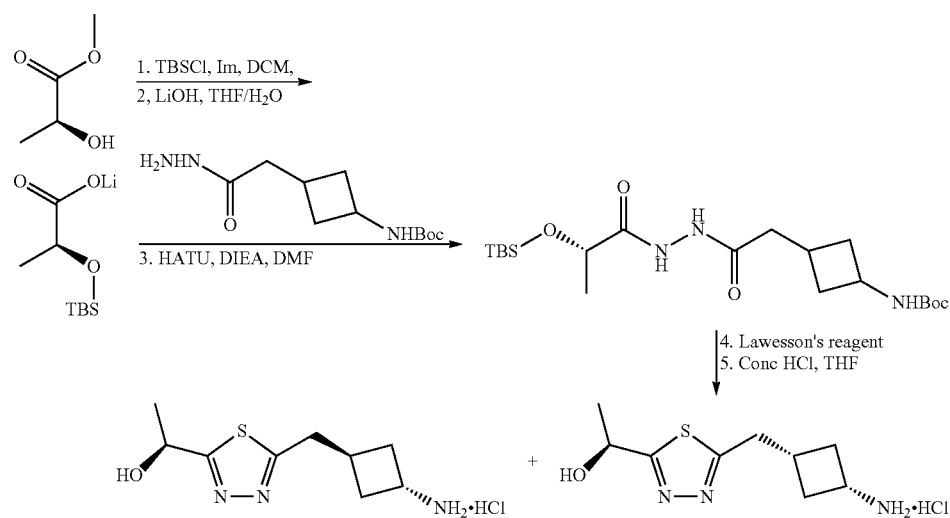

solution of ethyl 5-[3-(hydroxymethyl)cyclobutyl]-1,3,4-thiadiazole-2-carboxylate (1.8 g, 7.43 mmol, 1.00 eq.) in tetrahydrofuran (100 mL) was added triphenyl phosphine (3.9 g, 14.87 mmol, 2.00 eq.) in portions at 0° C. in 10 min. This was followed by the addition of DIAD (3 g, 14.78 mmol, 2.00 eq.) and di-tert-butyl iminodicarboxylate (2.4 g, 11.05 mmol, 1.50 eq.). The resulting solution was stirred for 3 hours at 2 5° C. and then diluted with water (200 mL). The resulting solution was extracted with ethyl acetate (3×200 mL) and the organic layers combined. The mixture was washed with brine (2×200 mL), dried over anhydrous Step 1: methyl (S)-2-((tert-butyldimethylsilyl)oxy)propanoate: a solution of methyl (2S)-2-hydroxypropanoate (5 g, 48.03 mmol, 1.00 eq.) and 1H-imidazole (4.9 g, 71.98 mmol, 1.50 eq.) in dichloromethane (100 mL) was placed into a 250-mL round-bottom flask. This was followed by the addition of a solution of tert-butyl(chloro)dimethylsilane (8.69 g, 57.66 mmol, 1.20 eq.) in dichloromethane (50 mL) dropwise with stirring at 0° C. The resulting solution was stirred for 2 hours at room temperature. The reaction was then quenched by the addition of 80 mL of water/ice and extracted with dichloromethane (3×50 mL). The resulting mixture was washed with brine (2×100 mL), dried over anhydrous sodium sulfate and concentrated under vacuum. This resulted in 8 g (76%) of methyl (2S)-2-[(tert-butyldimethylsilyl)oxy]propanoate as a colorless liquid.

Step 2: lithio (2S)-2-[(tert-butyldimethylsilyl)oxy]propanoate: a solution of methyl (2S)-2-[(tert-butyldimethylsilyl)oxy]propanoate (7.2 g, 32.97 mmol, 1.00 eq.) in THF (50 mL) was placed in a 250 mL round bottom flask. This was followed by the addition of a solution of lithium hydroxide (1.67 g, 39.80 mmol, 1.20 eq.) in H₂O (30 mL) dropwise with stirring. The resulting solution was stirred for 4 hours at room temperature. The resulting mixture was concentrated under vacuum. This resulted in 5.9 g (85%) of lithio (2S)-2-[(tert-butyldimethylsilyl)oxy]propanoate as a white solid.

Step 3: tert-butyl N-[3-([N-[(2S)-2-[(tert-butyldimethylsilyl)oxy]propanoyl]hydrazinecarbonyl]methyl)cyclobutyl]carbamate: a solution of lithio (2S)-2-[(tert-butyldimethylsilyl)oxy]propanoate (5.9 g, 28.06 mmol, 1.00 eq.), tert-butyl N-[3-[(hydrazine carbonyl)methyl]cyclobutyl]carbamate (7.51 g, 30.87 mmol, 1.10 eq.) and HATU (16 g, 42.11 mmol, 1.50 eq.) in DMF (100 mL) were placed in a 250-mL round-bottom flask. This was followed by the addition of DIEA (10.9 g, 84.34 mmol, 3.00 eq.) dropwise with stirring at 0° C. The resulting solution was stirred for 4 hours at room temperature. The reaction was then quenched by the addition of 100 mL of water/ice and extracted with ethyl acetate (3×100 mL) and the organic layers combined. The resulting mixture was washed with brine (3×80 mL), dried over anhydrous sodium sulfate and concentrated under vacuum. The residue was applied onto a silica gel column with ethyl acetate/hexane (1:1). This resulted in 4.4 g (36%) of tert-butyl N-[3-([N-[(2S)-2-[(tert-butyldimethylsilyl)oxy]propanoyl]hydrazinecarbonyl]methyl)cyclobutyl]carbamate as off-white solid. LC-MS: (M+H)⁺=430.

Step 4: tert-butyl N-[3-([5-[(1S)-1-[(tert-butyldimethylsilyl)oxy]ethyl]-1,3,4-thiadiazol-2-yl]methyl)cyclobutyl]carbamate:a solution of tert-butyl N-[3-([N-[(2S)-2-[(tert-butyldimethylsilyl)oxy]propanoyl]hydrazinecarbonyl]methyl)cyclobutyl]carbamate (4.4 g, 10.24 mmol, 1.00 eq.) and Lawesson reagent (6.2 g, 15.33 mmol, 1.50 eq.) in toluene (100 mL) were placed in a 250-mL round-bottom flask. The resulting solution was stirred for 2 hours at 80° C. in an oil bath. The reaction was then quenched by the addition of 50 mL of water/ice and extracted with ethyl acetate (3×80 mL) and the organic layers combined. The resulting mixture was washed with brine (2×50 mL), dried over anhydrous sodium sulfate and concentrated under vacuum. The residue was applied onto a silica gel column with ethyl acetate/petroleum ether (1:5). The crude product was purified by Flash-Prep-HPLC with the following conditions (CombiFlash-1): Column, C18 silica gel; mobile phase, H₂O/CH₃CN=1:1 increasing to H₂O/CH₃CN=1:9 within 30 min; Detector, UV 210 nm. This resulted in 2.1 g (48%) of tert-butyl N-[3-([5-[(1 S)-1-[(tert-butyldimethylsilyl)oxy]ethyl]-1,3,4-thiadiazol-2-yl]methyl)cyclobutyl]carbamate as colorless oil. LC-MS: (M+H)⁺=428.

Step 5: (1S)-1-[5-[(3-aminocyclobutyl)methyl]-1,3,4-thiadiazol-2-yl]ethan-1-ol hydrochloride: a solution of tert-butyl N-[3-([5-[1(1S)-1-[(tert-butyldimethylsilyl)oxy]ethyl]-1,3,4-thiadiazol-2-yl]methyl)cyclobutyl]carbamate (2.1 g, 4.91 mmol, 1.00 eq.) in THF (50 mL) was placed in a 100-mL round-bottom flask. To the mixture was added concentrated hydrogen chloride aqueous (5 mL). The resulting solution was stirred for 3 hours at room temperature. The resulting mixture was concentrated under vacuum. This resulted in 1.2 g (crude) of (1S)-1-[5-[(3-aminocyclobutyl)methyl]-1,3,4-thiadiazol-2-yl]ethan-1-ol hydrochloride as a colorless crude oil. LC-MS: (M+H)⁺=214.

Amines 17 and 18: (R)-1-(5-(cis-3-(aminomethyl)cyclobutyl)-1,3,4-thiadiazol-2-yl)ethan-1-ol hydrochloride and (R)-1-(5-(trans-3-(aminomethyl)cyclobutyl)-1,3,4-thiadiazol-2-yl)ethan-1-ol hydrochloride are prepared by the procedure described for amines 15 and 16 using (R)-lactic acid.

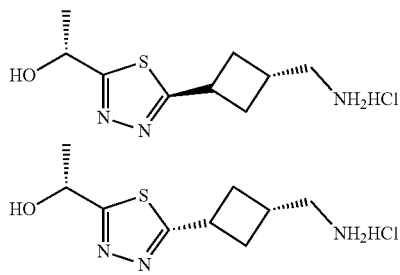

Amines 19 and 20: cis-3-((5-((R)-1-((tert-butyldimethylsilyl)oxy)ethyl)-1,3,4-oxadiazol-2-yl)methyl)cyclobutan-1-amine 2,2,2-trifluoroacetate and trans-3-((5-((R)-1-((tert-butyldimethylsilyl)oxy)ethyl)-1,3,4-oxadiazol-2-yl)methyl)cyclobutan-1-amine 2,2,2-trifluoroacetate

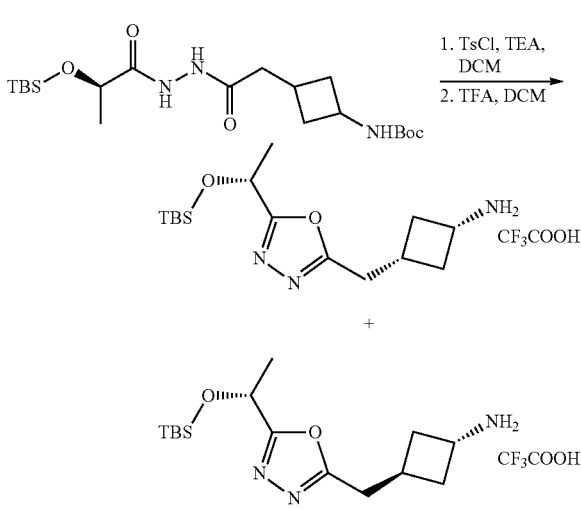

Step 1: tert-butyl N-[3-([5-[(1R)-1-[(tert-butyldimethylsilyl)oxy]ethyl]-1,3,4-oxadiazol-2-yl]methyl)cyclobutyl]carbamate: TEA (7 g, 69.18 mmol, 4.00 eq.) was added dropwise to a solution of tert-butyl N-[3-([N-[(2R)-2-[(tert-butyldimethylsilyl)oxy]propanoyl]hydrazinecarbonyl]methyl)cyclobutyl]carbamate (7.4 g, 17.22 mmol, 1.00 eq.) and 4-methylbenzene-1-sulfonyl chloride (9.85 g, 51.67 mmol, 3.00 eq.) in dichloromethane (100 mL). The resulting solution was stirred for 24 hours at room temperature. The reaction was then quenched by the addition of 100 mL of water/ice. The resulting solution was extracted with dichloromethane (3×100 mL) and the organic layers combined. The resulting mixture was washed with brine (2×50 mL), dried over anhydrous sodium sulfate and concentrated under vacuum. The residue was applied onto a silica gel column with ethyl acetate/petroleum ether (1:5) to give 4.3 g (61%) of tert-butylN-[3-([5-[(1R)-1-[(tert-butyldimethylsilyl)oxy]

ethyl]-1,3,4-oxadiazol-2-yl]methyl)cyclobutyl]carbamate as colorless oil. LC-MS: (M+H)⁺=412.

Step 2: [3-([5-[(1R)-1-[(tert-butyldimethylsilyl)oxy]ethyl]-1,3,4-oxadiazol-2-yl]methyl)cyclobutyl]amino 2,2,2-trifluoroacetate: trifluoroacetic acid (8 mL) was added to a solution of tert-butyl N-[3-([5-[(1R)-1-[(tert-butyldimethylsilyl)oxy]ethyl]-1,3,4-oxadiazol-2-yl]methyl)cyclobutyl]carbamate (3.2 g, 7.77 mmol, 1.00 eq.) in dichloromethane (50 mL). The resulting solution was stirred for 16 hours at room temperature and then concentrated under vacuum to give 3.2 g (97%) of [3-([5-[(1R)-1-[(tert-butyldimethylsilyl)oxy]ethyl]-1,3,4-oxadiazol-2-yl]methyl)cyclobutyl]amino 2,2,2-trifluoroacetate as colorless crude oil. LC-MS: (M+H)⁺=312.

Amines 21 and 22: cis-3-((5-((S)-1-((tert-butyldimethylsilyl)oxy)ethyl)-1,3,4-oxadiazol-2-yl)methyl)cyclobutan-1-amine 2,2,2-trifluoroacetate and trans-3-((5-((S)-1-((tert-butyldimethylsilyl)oxy)ethyl)-1,3,4-oxadiazol-2-yl)methyl)cyclobutan-1-amine 2,2,2-trifluoroacetate were prepared using (S)-lactic acid.

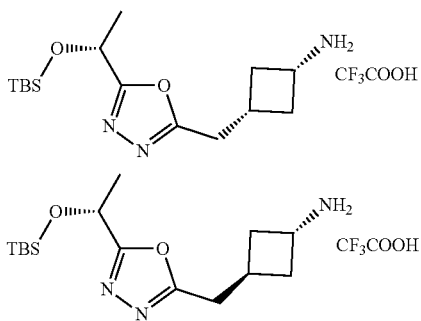

Amines 23 and 24: (5-cis-3-aminocyclobutyl)methyl)-1,3,4-thiadiazol-2-yl)methanol hydrochloride and (5-(trans-3-aminocyclobutyl)methyl)-1,3,4-thiadiazol-2-yl)methanol hydrochloride

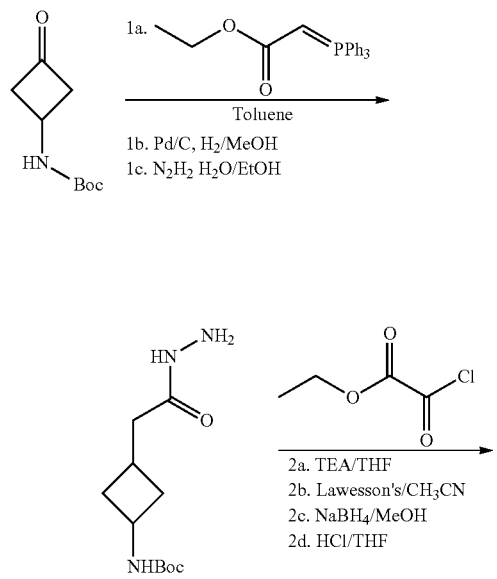

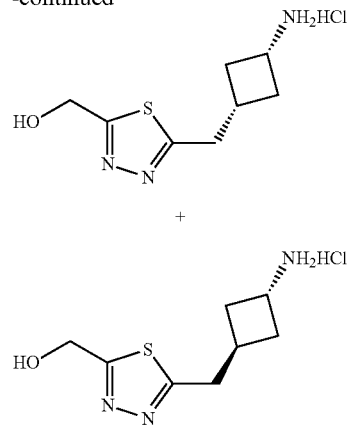

Step 1a: ethyl 2-(3-((tert-butoxycarbonyl)amino)cyclobutylidene)acetate: a solution of tert-butyl N-(3-oxocyclobutyl) carbamate (8 g, 43.19 mmol, 1.00 eq.) and ethyl 2-(triphenyl-λ⁵-phosphanylidene)acetate (16.8 g, 48.22 mmol, 1.10 eq.) in toluene (100 mL) was stirred for 2 hours at 100° C. The resulting mixture was concentrated under vacuum and the mixture was purified by silica gel column and eluted with ethyl acetate/petroleum ether (0-5%) to give crude (10.5 g) of ethyl 2-(3-[[(tert-butoxy)carbonyl]amino]cyclobutylidene)acetate as a white solid. LC-MS: 256 [M+H]⁺.

Step 1b: ethyl 2-(3-[[(tert-butoxy)carbonyl]amino]cyclobutyl)acetate: Palladium carbon (210 mg) was added to a solution of ethyl 2-(3-[[(tert-butoxy)carbonyl]amino]cyclobutylidene)acetate (10.5 g, 41.13 mmol, 1.00 eq.) in methanol (150 mL), and the mixture was hydrogenated for 2 h at rt. The solids were filtered out and the mixture was concentrated under vacuum. This resulted in 10.6 g (crude) of ethyl 2-(3-[[(tert-butoxy)carbonyl]amino]cyclobutyl)acetate as a white solid. LC-MS: 258 [M+H]⁺.

Step 1c: tert-butyl N-[3-[(hydrazine carbonyl)methyl]cyclobutyl]carbamate: a solution of ethyl 2-(3-[[(tert-butoxy)carbonyl]amino]cyclobutyl)acetate (9.74 g, 37.85 mmol, 1.00 eq.) and hydrazine hydrate (11.4 mL) in ethanol (300 mL) was heated for 17 hours at 80° C. The resulting solution was diluted with water (500 mL) and then extracted with ethyl acetate (3×300 mL) and the combined organic layer was dried over anhydrous sodium sulfate and concentrated under vacuum. The crude product was re-crystallized from ethyl acetate/petroleum ether in the ratio of 1:2. This resulted in 6.88 g (crude) of tert-butyl N-[3-[(hydrazine carbonyl)methyl]cyclobutyl]carbamate as a white solid. LC-MS: 244 [M+H]⁺.

Step 2a: ethyl 2-[2-(3-[[(tert-butoxy)carbonyl]amino]cyclobutyl)acetohydrazido]-2-oxoacetate: ethyl 2-chloro-2-oxoacetate (4.74 g, 34.72 mmol, 1.20 eq.) was added dropwise to a cold solution (0° C.) of tert-butyl N-[3-[(hydrazine carbonyl)methyl]cyclobutyl]carbamate (7.04 g, 28.94 mmol, 1.00 eq.) and TEA (5.84 g, 57.71 mmol, 2.00 eq.) in tetrahydrofuran (150 mL). The resulting solution was stirred for 1 hour at room temperature, filtered and the resulting mixture was concentrated under vacuum. The residue was applied onto a silica gel column and eluted with ethyl acetate/petroleum ether (4:1) to give crude (9.5 g) of ethyl 2-[2-(3-[[(tert-butoxy)carbonyl]amino]cyclobutyl)acetohydrazido]-2-oxoacetate as a yellow solid. LC-MS: 344 [M+H]⁺.

Step 2b: ethyl 5-[(3-[[(tert-butoxy)carbonyl]amino]cyclobutyl)methyl]-1,3,4-thiadiazole-2-carboxylate: a solution of ethyl 2-[2-(3-[[(tert-butoxy)carbonyl]amino]cyclobutyl)acetohydrazido]-2-oxoacetate (9.5 g, 27.67 mmol, 1.00 eq.) and Lawesson's reagent (11.19 g, 27.67 mmol, 1.00 eq.) in MeCN (200 mL) was heated 16 hours at 50° C. The reaction was then quenched by the addition of ice-water (300 mL). The resulting solution was extracted with ethyl acetate (4×200 mL). The combined organic layer was dried over anhydrous sodium sulfate and concentrated under vacuum to give crude (1.6 g) ethyl 5-[(3-[[(tert-butoxy)carbonyl]amino]cyclobutyl)methyl]-1,3,4-thiadiazole-2-carboxylate as a yellow solid. LC-MS: 342.2 [M+H]+.

Step 2c: tert-butyl N-(3-[[5-(hydroxymethyl)-1,3,4-thiadiazol-2-yl]methyl]cyclobutyl)carbamate: NaBH₄ (399 mg, 10.55 mmol, 3.00 eq.) was added in several batches to a cold solution (0° C.) of ethyl 5-[(3-[[(tert-butoxy)carbonyl]amino]cyclobutyl)methyl]-1,3,4-thiadiazole-2-carboxylate (1.2 g, 3.51 mmol, 1.00 eq.) in methanol (20 mL). The resulting solution was stirred for 1 hour at 0° C. and then quenched by the addition of water (3 mL). The mixture was filtered and then concentrated under vacuum to give crude (1.146 g) tert-butyl N-(3-[[5-(hydroxymethyl)-1,3,4-thiadiazol-2-yl]methyl]cyclobutyl)carbamate as a yellow solid. LC-MS: 300.1 [M+H]+.

Step 2d: [5-[(3-aminocyclobutyl)methyl]-1,3,4-thiadiazol-2-yl]methanol hydrochloride: a solution of tert-butyl N-(3-[[5-(hydroxymethyl)-1,3,4-thiadiazol-2-yl]methyl]cyclobutyl)carbamate (1.45 g, 4.84 mmol, 1.00 eq.) and concentrated hydrogen chloride aqueous (2 mL) in tetrahydrofuran (20 mL) was stirred for 16 hours at room temperature. The resulting mixture was concentrated under vacuum. This resulted in 980 mg (crude) of [5-[(3-aminocyclobutyl)methyl]-1,3,4-thiadiazol-2-yl]methanol hydrogen chloride salt as a yellow solid. LC-MS: 200.0 [M+H-HCl]+.

Amine 25: trans-3-(5-((R)-1-((tert-butyldimethylsilyl)oxy)ethyl)-1,3,4-oxadiazol-2-yl)cyclobutan-1-amine

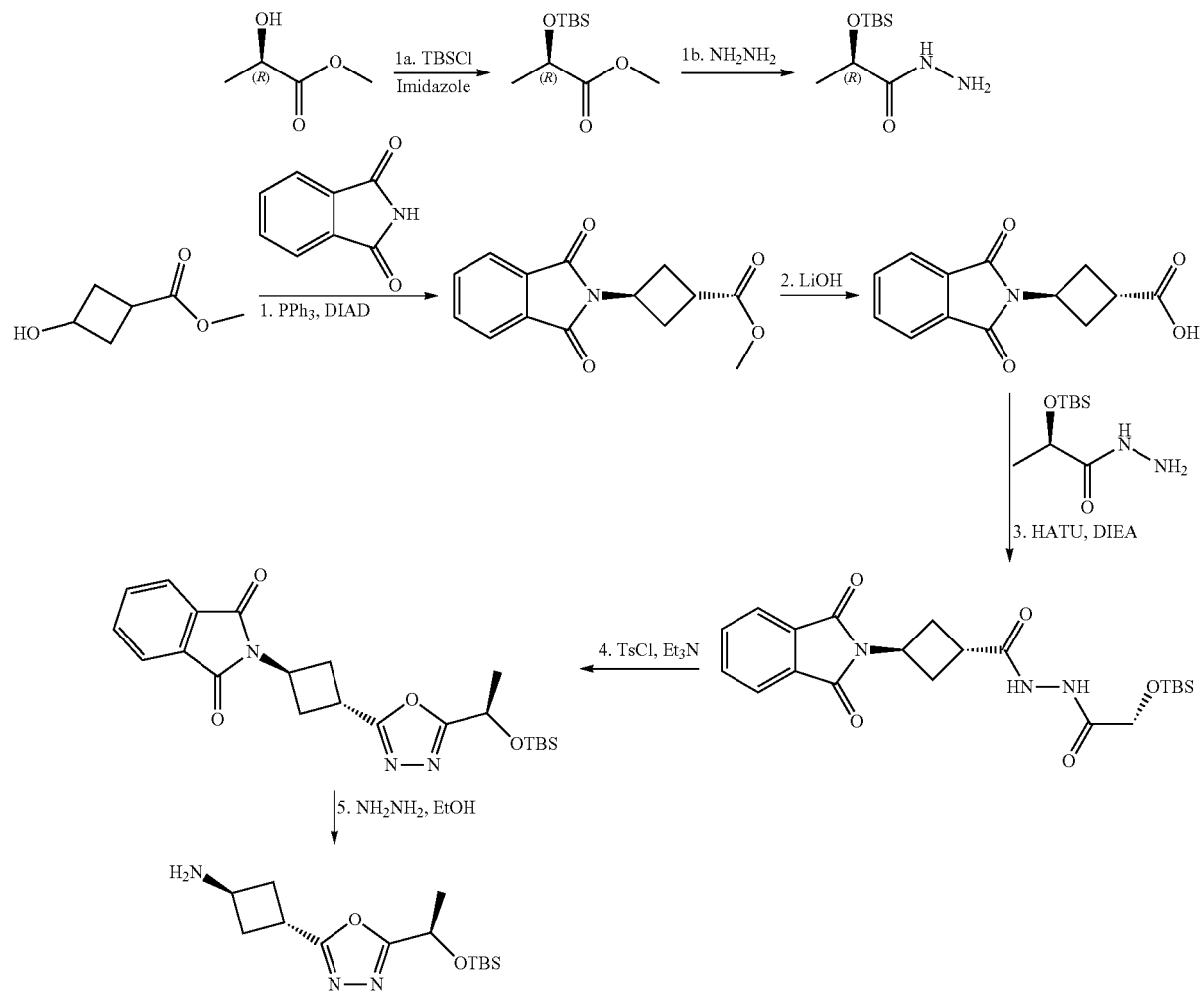

Step 1a: methyl (2R)-2-[(tert-butyldimethylsilyl)oxy]propanoate: into a 250-mL round-bottom flask, was placed a solution of methyl (2R)-2-hydroxypropanoate (5 g, 48.03 mmol, 1.00 equiv) and Imidazole (6.5 g, 95.59 mmol, 2.00 equiv) in dichloromethane (100 mL). This was followed by the addition of tert-butyl(chloro)dimethylsilane (8.7 g, 57.72 mmol, 1.20 equiv) in dichloromethane (50 mL) dropwise with stirring at 0° C. The resulting solution was stirred for 2 hours at room temperature. The reaction was then quenched by the addition of 100 mL of water/ice. The resulting solution was extracted with dichloromethane (3×100 mL) and the organic layers combined. The resulting mixture was washed with brine (3×50 mL), dried over anhydrous sodium sulfate and concentrated under vacuum. This resulted in 7 g (67%) of methyl (2R)-2-[(tert-butyldimethylsilyl)oxy]propanoate as colorless oil.

Step 1b: (2R)-2-[(tert-butyldimethylsilyl)oxy]propanehydrazide: into a 250-mL round-bottom flask, was placed a solution of methyl (2R)-2-[(tert-butyldimethylsilyl)oxy]propanoate (7 g, 32.06 mmol, 1.00 equiv) in ethanol (100 mL). To the solution was added hydrazine (10 g, 159.81 mmol, 5.00 equiv, 80%). The resulting solution was stirred for 15 hours at 90° C. in an oil bath. The resulting solution was quenched by the addition of water/ice. The resulting solution was extracted with ethyl acetate (3×100 mL) and the organic layers combined. The resulting mixture was washed with brine (2×100 mL), dried over anhydrous sodium sulfate and concentrated under vacuum. This resulted in 6.5 g (93%) of (2R)-2-[(tert-butyldimethylsilyl)oxy]propanehydrazide as colorless oil. LC-MS (ES, m/z): [M+1]$^+$=219.

Step 1: methyl (trans-3-(1,3-dioxo-2,3-dihydro-1H-isoindol-2-yl)cyclobutane-1-carboxylate: into a 250-mL round-bottom flask, under nitrogen, was placed a solution of methyl 3-cis-hydroxycyclobutane-1-carboxylate (8 g, 61.47 mmol, 1.00 equiv), 2,3-dihydro-1H-isoindole-1,3-dione (18.1 g, 123.02 mmol, 2.00 equiv) and triphenylphosphine (32.3 g, 123.15 mmol, 2.00 equiv) in THF (100 mL). This was followed by the addition of DIAD (24.9 g, 123.14 mmol, 2.00 equiv) dropwise with stirring at 0° C. The resulting solution was stirred for 2.5 hours at room temperature. The resulting mixture was concentrated under vacuum. The residue was applied onto a silica gel column with ethyl acetate/petroleum ether (1:5). The crude product was re-crystallized from petroleum ether/ethyl acetate in the ratio of 10:1. This resulted in 7.2 g (45%) of methyl trans-3-(1,3-dioxo-2,3-dihydro-1H-isoindol-2-yl)cyclobutane-1-carboxylate as a white solid. LC-MS (ES, m/z): [M+1]$^+$=260. $^1$H-NMR (400 MHz, CDCl$_3$): δ 7.85-7.82 (m, 2H), 7.74-7.71 (m, 2H), 5.08-5.04 (m, 1H), 3.75 (s, 3H), 3.34-3.32 (m, 1H), 3.20-3.12 (m, 2H), 2.66-2.60 (m, 2H).

Step 2: trans-3-(1,3-dioxo-2,3-dihydro-1H-isoindol-2-yl)cyclobutane-1-carboxylic acid: into a 100-mL round-bottom flask, was placed a solution of methyl trans-3-(1,3-dioxo-2,3-dihydro-1H-isoindol-2-yl)cyclobutane-1-carboxylate (7.2 g, 27.77 mmol, 1.00 equiv) in 1,4-dioxane (100 mL). To the solution was added 5M hydrogen chloride aqueous (10 mL). The resulting solution was stirred for 4 hours at 80° C. in an oil bath. The resulting mixture was concentrated under vacuum. This resulted in 6.2 g (91%) of trans-3-(1,3-dioxo-2,3-dihydro-1H-isoindol-2-yl)cyclobutane-1-carboxylic acid as a white solid. LC-MS (ES, m/z): [M-1]$^-$=244.

Step 3: (2R)-2-[(tert-butyldimethylsilyl)oxy]-N-[trans-3-(1,3-dioxo-2,3-dihydro-1H-isoindol-2-yl)cyclobutyl]carbonyl]propanehydrazide: into a 250-mL round-bottom flask, was placed a solution of trans-3-(1,3-dioxo-2,3-dihydro-1H-isoindol-2-yl)cyclobutane-1-carboxylic acid (6.2 g, 25.28 mmol, 1.00 equiv), (2R)-2-[(tert-butyldimethylsilyl)oxy]propanehydrazide (6.61 g, 30.27 mmol, 1.20 equiv) and HATU (14.4 g, 37.89 mmol, 1.50 equiv) in THF (100 mL). This was followed by the addition of DIEA (9.81 g, 75.91 mmol, 3.00 equiv) dropwise with stirring at 0° C. The resulting solution was stirred for 1 hour at room temperature. The reaction was then quenched by the addition of 100 mL of water/ice. The resulting solution was extracted with ethyl acetate (3×50 mL) and the organic layers combined. The resulting mixture was washed with brine (2×50 mL), dried over anhydrous sodium sulfate and concentrated under vacuum. The residue was applied onto a silica gel column with ethyl acetate/petroleum ether (1:4). This resulted in 7 g (62%) of (2R)-2-[(tert-butyldimethylsilyl)oxy]-N-[trans-3-((1,3-dioxo-2,3-dihydro-1H-isoindol-2-yl)cyclobutyl]carbonyl]propanehydrazide as colorless oil. LC-MS (ES, m/z): [M+1]$^+$=446.

Step 4: 2-[trans-3-[5-[(1R)-1-[(tert-butyldimethylsilyl)oxy]ethyl]-1,3,4-oxadiazol-2-yl]cyclobutyl]-2,3-dihydro-1H-isoindole-1,3-dione: into a 250-mL round-bottom flask, was placed a solution of (2R)-2-[(tert-butyldimethylsilyl)oxy]-N-[[trans-3-(1,3-dioxo-2,3-dihydro-1H-isoindol-2-yl)cyclobutyl]carbonyl]propanehydrazide (6.95 g, 15.60 mmol, 1.00 equiv) and TEA (7.89 g, 77.97 mmol, 5.00 equiv) in dichloromethane (100 mL). This was followed by the addition of a solution of 4-methylbenzene-1-sulfonyl chloride (8.92 g, 46.79 mmol, 3.00 equiv) in dichloromethane (50 mL) dropwise with stirring at 0° C. The resulting solution was stirred for 15 hours at room temperature. The reaction was then quenched by the addition of 100 mL of water/ice. The resulting solution was extracted with dichloromethane (2×50 mL) and the organic layers combined. The resulting mixture was washed with brine (2×50 mL), dried over anhydrous sodium sulfate and concentrated under vacuum. The crude product was purified by Flash-Prep-HPLC with the following conditions (IntelFlash-1): Column, C18; mobile phase, H$_2$O/CH$_3$CN=100:1 increasing to H$_2$O/CH$_3$CN=1:100 within 30 min; Detector, UV 254 nm. This resulted in 3.28 g (49%) of 2-[trans-3-[5-[(1R)-1-[(tert-butyldimethylsilyl)oxy]ethyl]-1,3,4-oxadiazol-2-yl]cyclobutyl]-2,3-dihydro-1H-isoindole-1,3-dione as colorless oil. LC-MS (ES, m/z): [M+1]$^+$=428. $^1$H-NMR (400 MHz, CDCl$_3$): δ 7.72-7.70 (m, 2H), 7.60-7.58 (m, 2H), 5.04-4.96 (m, 2H), 3.83-3.78 (m, 1H), 3.26-3.24 (m, 2H), 2.67-2.62 (m, 2H), 1.49-1.48 (d, J=6.8 Hz, 3H), 0.76 (s, 9H), 0.01 (s, 3H), 0.00 (s, 3H).

Step 5: trans-3-[5-[(1R)-1-[(tert-butyldimethylsilyl)oxy]ethyl]-1,3,4-oxadiazol-2-yl]cyclobutan-1-amine: into a 250-mL round-bottom flask, was placed a solution of 2-[trans-3-[5-[(1R)-1-[(tert-butyldimethylsilyl)oxy]ethyl]-1,3,4-oxadiazol-2-yl]cyclobutyl]-2,3-dihydro-1H-isoindole-1,3-dione (1.18 g, 2.76 mmol, 1.00 equiv) in ethanol (100 mL). To the solution was added hydrazine hydrate (3.45 g, 55.13 mmol, 20.00 equiv, 80%). The resulting solution was stirred for 3 hours at room temperature. The solids were filtered out. The resulting mixture was concentrated under vacuum. This resulted in 760 mg (crude) of trans-3-[5-[(1R)-1-[(tert-butyldimethylsilyl)oxy]ethyl]-1,3,4-oxadiazol-2-yl]cyclobutan-1-amine as colorless oil. LC-MS (ES, m/z): [M+1]$^+$=298.

Amine 26 and 27: trans-3-(5-((S)-1-((tert-butyldimethylsilyl)oxy)ethyl)-1,3,4-oxadiazol-2-yl)cyclobutan-1-amine are prepared using the same methodology as described for amine 24.

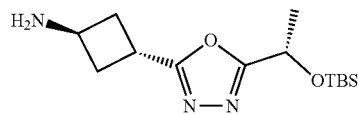

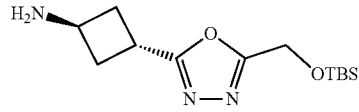

Amine 28 and 29: (5-(cis-3-aminocyclobutyl)-1,3,4-thiadiazol-2-yl)methanol and (5-(trans-3-aminocyclobutyl)-1,3,4-thiadiazol-2-yl)methanol

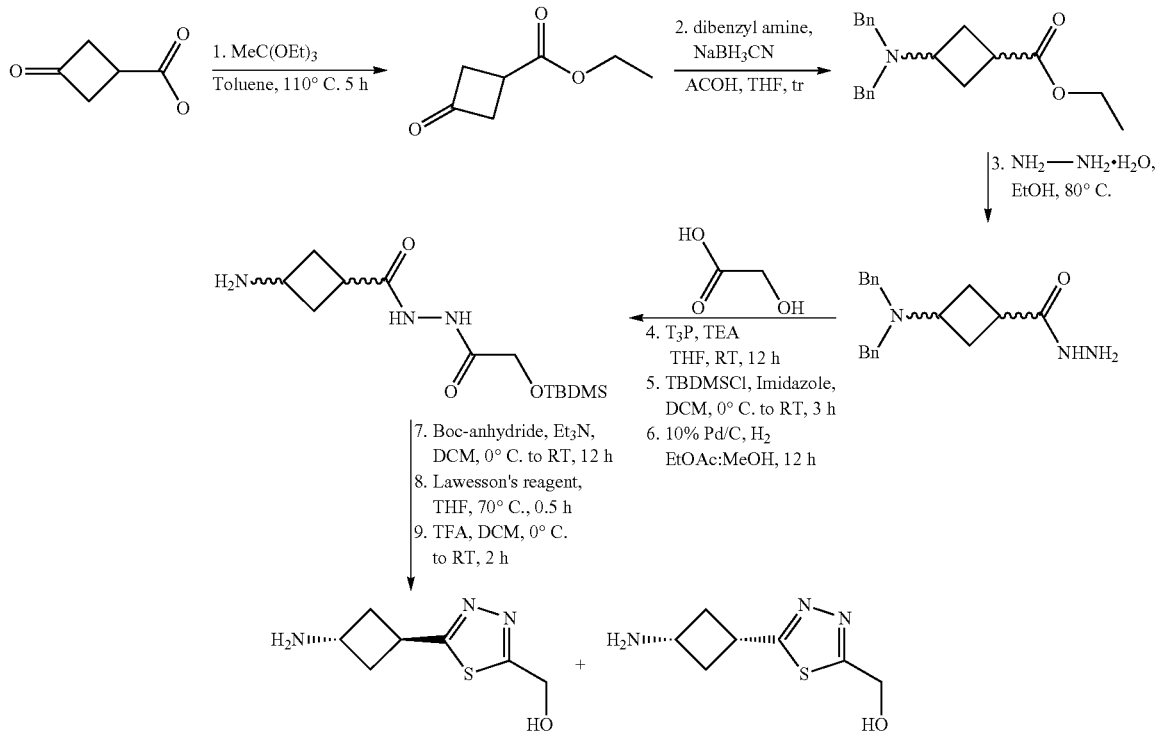

Step 1: ethyl 3-oxocyclobutane-1-carboxylate: triethyl orthoacetate (24.25 g, 104 mmol) was added to a solution of 3-oxo-cyclobutanecarboxylic acid (5.0 g, 34.7 mmol) in toluene (100 mL) and the reaction mixture was heated to reflux for 5 h. The reaction mixture was cooled to 0° C. and quenched with 1N HCl. Organic layer was separated off and the aq. phase was extracted with ethyl acetate (2×20 mL). Combined organic layer was washed with saturated NaHCO$_3$ solution followed by water (50 mL) and dried over Na$_2$SO$_4$. Solvent removal under reduced pressure afforded the product (5.8 g, 93.5%) as a pale yellow oil. $^1$H NMR (400 MHz, CDCl$_3$): δ 4.20 (q, J=7.1 Hz, 2H), 3.44-3.37 (m, 2H), 3.31-3.17 (m, 3H,), 1.28 (t, J=7.1 Hz, 3H)

Step 2: ethyl 3-(dibenzylamino)cyclobutane-1-carboxylate: added dibenzyl amine (3.05 g, 15.4 mmol) was added to a solution of ethyl 3-oxocyclobutane-1-carboxylate (2.0 g, 14.4 mmol) in 10% THF in AcOH (50 mL) and the reaction mixture was stirred at room temperature for 20 min followed by addition of sodium cyanoborohydride (1.77 g, 28 mmol) portion wise. The mixture was stirred at room temperature for 12 h, volatiles were removed under reduced pressure and the crude compound was diluted with DCM (50 mL). DCM layer was washed with water and saturated NaHCO$_3$ solution, dried over Na$_2$SO$_4$ and concentrated under reduced pressure to get the crude compound. The crude compound was purified by combiflash using 10% ethyl acetate in hexane as eluent to afford the product (2.0 g, 44.4%) as colorless oil. $^1$H NMR (400 MHz, CDCl$_3$): δ 7.33-7.26 (m, 8H), 7.23-7.20 (m, 2H), 4.13-4.07 (m, 2H), 3.49 (s, 3H), 3.46 (s, 1H), 3.12-3.07 (m, 1H), 2.66-2.61 (m, 1H), 2.25-2.03 (m, 4H), 1.25-1.22 (t obscured by occluded EtOAc, 3H); LC-MS: [M+H]$^+$ 324.4

Step 3: 3-(dibenzylamino)cyclobutane-1-carbohydrazide: hydrazine hydrate (0.99 mL, 30.9 mmol) was added to a solution of ethyl 3-(dibenzylamino)cyclobutane-1-carboxylate (2.0 g, 6.19 mmol) in EtOH (20 mL) and the reaction mixture was refluxed for 12 h. The volatiles were removed under reduced pressure and the crude compound was washed with hexane (2×20 mL). The residue thus obtained was dried under vacuum to get the product (1.8 g, 94.2%) as a white solid. $^1$H NMR (400 MHz, CDCl$_3$): δ 7.31-7.26 (m, 8H), 7.25-7.20 (m, 2H), 6.80 (s, 1H), 3.83 (br, 2H), 3.50 (s, 4H), 3.13-3.05 (m, 1H), 2.51-2.42 (m, 1H), 2.23-2.10 (m, 4H); LC-MS: [M+H]+=309.9

Step 4: 3-(dibenzylamino)-N'-(2-hydroxyacetyl)cyclobutane-1-carbohydrazide: triethyl amine (2.7 mL, 19 mmol) was added to a solution of glycolic acid (0.5 g, 6.5 mmol) in DCM (20 mL) followed by T$_3$P (3.13 g, 9.8 mmol) and the reaction mixture was stirred for 10 min. 3-(dibenzylamino)cyclobutane-1-carbohydrazide (2.23 g, 7.2 mmol) was added to the resulting reaction mixture and it was stirred at room temperature for 12 h. The reaction mixture was diluted with ice-water (20 mL) and the aq. phase was extracted with DCM (2×20 mL). Combined organic layer was washed with brine (20 mL), dried over Na$_2$SO$_4$ and concentrated under reduced pressure to get the crude compound. The crude compound was purified by combiflash using 3% MeOH in DCM as eluent to give the product (2.3 g, crude) as a white solid which was used as such in next step without further purification.

Step 5: N'-(2-((tert-butyldimethylsilyl)oxy)acetyl)-3-(dibenzylamino)cyclobutane-1-carbohydrazide: imidazole (0.93 g, 13.7 mmol) was added to a solution of 3-(dibenzylamino)-N'-(2-hydroxyacetyl)cyclobutane-1-carbohydrazide (2.3 g, crude) in dry DMF (5 mL) and the reaction mixture was stirred for 10 minutes under N$_2$ atmosphere. The reaction mixture was cooled in an ice bath, and TBDM- SCl (1.88 g, 12.5 mmol) was added and the resulting reaction mixture was stirred at room temperature for 3 h. The reaction mixture was quenched with water (10 mL) and extracted with ethyl acetate (3×50 mL). Combined organic layer was dried over Na₂SO₄ and concentrated under reduced pressure to get the crude compound. The mixture was purified by column chromatography using 30% ethyl acetate in hexane as eluent to get the product (2.0 g, 57% over two steps) as a white solid. ¹H NMR (400 MHz, CDCl₃): δ 8.95 (d, J=5.9 Hz, 1H), 8.19 (d, J=6.6 Hz, 1H), 7.30-7.28 (m, 8H), 7.26-7.27 (m, 2H), 4.20 (s, 2H), 3.50 (s, 4H), 3.15-3.11 (m, 1H), 2.61-2.57 (m, 1H), 2.24-2.20 (m, 4H), 0.92 (s, 9H), 0.11 (s, 6H); LC-MS: [M+H]+ 482.0

Step 6: 3-amino-N'-(2-((tert-butyldimethylsilyl)oxy) acetyl)cyclobutane-1-carbohydrazide: 10% Pd—C (0.2 g) was added to a mixture of N-'(2-(((tert-butyldimethylsilyl)oxy)acetyl)-3-(dibenzylamino)cyclobutane-1-carbohydrazide (2.0 g, 4.15 mmol) in EtOAc-MeOH (30 mL) and the reaction mixture was stirred under H₂ atmosphere for 12 h at room temperature. The reaction mixture was filtered and washed with MeOH (2×10 mL). Filtrate was concentrated under reduced pressure to get the crude compound. The crude compound was purified by column chromatography using 20% MeOH in DCM as eluent to afford the product (0.8 g, 64.0%) as a white solid. ¹H NMR (400 MHz, CDCl₃): δ 4.2 (s, 2H), 3.47-3.35 (m, 1H), 2.67-2.58 (m, 1H), 2.55-2.48 (m, 2H), 2.03-1.96 (m, 2H), 0.93 (s, 9H), 0.11 (s, 6H); LC-MS: [M+H]⁺ 301.9.

Step 7: tert-butyl (3-(2-(2-((tert-butyldimethylsilyl)oxy) acetyl)hydrazine-1-carbonyl)cyclobutyl) carbamate: triethyl amine (0.74 mL, 5.31 mmol) was added to an ice cooled solution of 3-amino-N'-(2-((tert-butyldimethylsilyl)oxy) acetyl)cyclobutane-1-carbohydrazide (0.8 g, 2.65 mmol) in DCM (10 mL). Boc-anhydride (0.91 mL, 3.98 mmol) was added to the mixture and the reaction mixture was stirred at room temperature for 12 h. The reaction was diluted with cold water (20 mL) and extracted with DCM (2×10 mL). Combined organic layer was dried over Na₂SO₄ and evaporated to dryness under vacuum to get the crude compound. The crude compound was purified by combiflash using 3% MeOH in DCM as eluent to afford the product (0.9 g, crude) as an off white solid. As per 1H-NMR, compound is not pure and used as such in next step.

Step 8: tert-butyl (3-(5-(((tert-butyldimethylsilyl)oxy) methyl)-1,3,4-thiadiazol-2-yl)cyclobutyl) carbamate: Lawesson's reagent (3.52 g, 8.7 mmol) was added to a solution of -butyl (3-(2-(2-((tert-butyldimethylsilyl)oxy) acetyl)hydrazine-1-carbonyl)cyclobutyl) carbamate (0.7 g, 1.74 mmol) in THF (10 mL) and the reaction mixture was heated to 70° C. for 30 min. The volatiles were removed under reduced pressure and the crude compound was purified by neutral alumina column chromatography using 15% EtOAc in hexane to afford the product (0.3 g, 32% over two steps) as white solid. ¹H NMR (400 MHz, CDCl₃): δ 5.0 (s, 2H), 4.81-4.80 (br, 1H), 4.21 (m, 1H), 3.58-3.49 (m, 1H), 2.92-2.87 (m, 2H), 2.28-2.20 (m, 2H), 1.43 (s, 9H), 0.92 (s, 9H), 0.11 (s, 6H); LC-MS: [M+H]⁺ 399.6.

Step 9: (5-(cis/trans 3-aminocyclobutyl)-1,3,4-thiadiazol-2-yl)methanol: trifluoroacetic acid (0.171 g, 1.5 mmol) was added to an ice cooled solution of tert-butyl (3-(5-(((tert-butyldimethylsilyl)oxy)methyl)-1,3,4-thiadiazol-2-yl)cyclobutyl) carbamate (0.3 g, 7.5 mmol) in DCM (5 mL) and the reaction mixture was stirred at room temperature for 2 h. The volatiles were removed under reduced pressure to get the product (0.178 g, crude) as a white solid which was used as such in next step without further purification.

Amine 30 and 31: (R)-1-(5-(cis-3-aminocyclobutyl)-1,3, 4-thiadiazol-2-yl)ethan-1-ol and (R)-1-(5-(trans-3-aminocyclobutyl)-1,3,4-thiadiazol-2-yl)ethan-1-ol are prepared using the procedure shown for amines 28 and 29 using (R)-lactic acid.

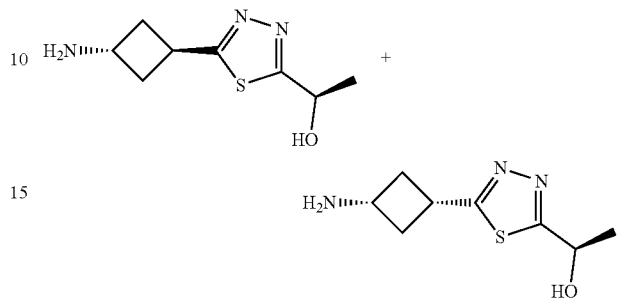

Amine 30 and 31: (S)-1-(5-(cis-3-aminocyclobutyl)-1,3, 4-thiadiazol-2-yl)ethan-1-ol and (S)-1-(5-(trans-3-aminocyclobutyl)-1,3,4-thiadiazol-2-yl)ethan-1-ol are prepared using the procedure shown for amines 28 and 29 using (S)-lactic acid.

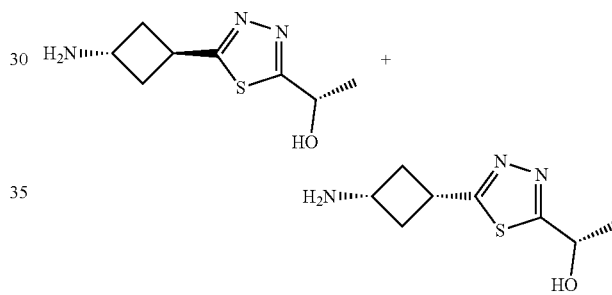

Amine 32 and 33: 1-(1-(R)-cis-3-aminocyclobutyl)-1H-pyrazol-4-yl)ethan-1-ol and 1-(1-(S)-cis-3-aminocyclobutyl)-1H-pyrazol-4-yl)ethan-1-ol

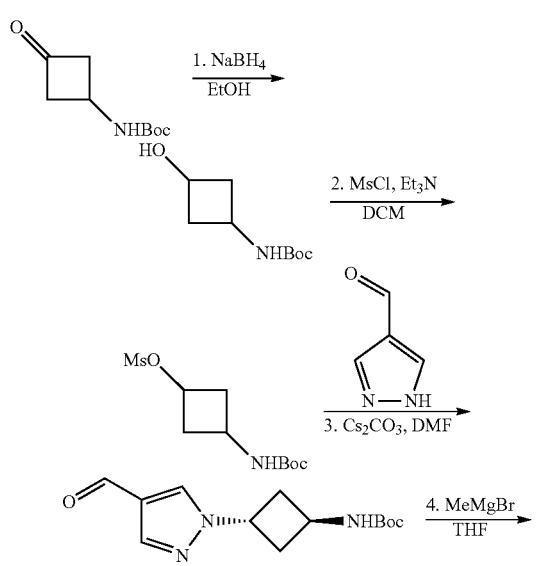

-continued

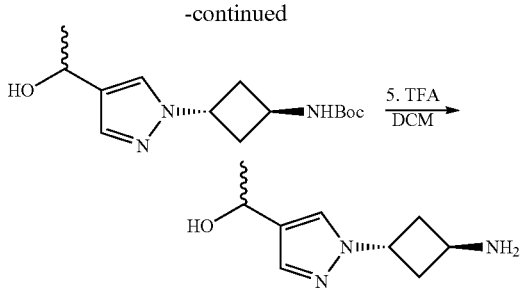

Step 1: tert-butyl (3-hydroxycyclobutyl)carbamate: NaBH₄ (1.02 g, 26.96 mmol, 0.50 eq.) was added slowly to a 0° C. solution of tert-butyl N-(3-oxocyclobutyl)carbamate (10 g, 53.99 mmol, 1.00 eq.) in ethanol (100 mL). The resulting solution was stirred for 1 hour at 25° C. and then concentrated under vacuum. This resulted in 9.9 g (98%) of tert-butyl N-(3-hydroxycyclobutyl)carbamate as a white solid.

Step 2: 3-((tert-butoxycarbonyl)amino)cyclobutyl methanesulfonate: methanesulfonyl chloride (6.7 g, 58.49 mmol, 1.10 eq.) was added dropwise (5 min) to a 0° C. solution of tert-butyl N-(3-hydroxycyclobutyl)carbamate (9.9 g, 52.87 mmol, 1.00 eq.) and TEA (10.8 g, 106.73 mmol, 2.00 eq.) in dichloromethane (200 mL). The resulting solution was stirred for 3 hours at 25° C., the mixture was diluted with 400 mL of water. The resulting solution was extracted with dichloromethane (3×200 mL) and the organic layers combined. The resulting mixture was washed with brine (3×200 mL), dried over anhydrous sodium sulfate and concentrated under vacuum. This resulted in 11.4 g (81%) of tert-butyl N-[3-(methanesulfonyloxy)cyclobutyl]carbamate as a yellow solid.

Step 3: tert-butyl N-trans-3-(4-formyl-1H-pyrazol-1-yl)cyclobutyl]carbamate: 1H-pyrazole-4-carbaldehyde (1.73 g, 18.00 mmol, 1.20 eq.) and Cs₂CO₃ (9.78 g, 30.02 mmol, 2.00 eq.) were added to a solution of tert-butyl N-[3-(methanesulfonyloxy)cyclobutyl]carbamate (4 g, 15.08 mmol, 1.00 eq.) in DMF (100 mL). The resulting solution was stirred for 16 hours at 80° C. and then diluted with 300 mL of water. The resulting solution was extracted with ethyl acetate (3×300 mL) and the organic layers combined. The resulting mixture was washed with brine (3×500 mL), dried over anhydrous sodium sulfate and concentrated under vacuum. The crude product was purified by Flash with the following conditions: Column, C18 silica gel; mobile phase, X:H₂O Y:ACN=70/30 increasing to X:H₂O Y:ACN=20/80 within 30 min; Detector, UV 254 nm. The isomers were separated by Prep-SFC with the following conditions (Prep SFC80-2): Column, Chiralpak IB, 2*25 cm, 5 um; mobile phase, CO₂ (80%), IPA (20%); Detector, UV 220 nm. This resulted in 1.2 g (30%) of tert-butyl N-trans-3-(4-formyl-1H-pyrazol-1-yl)cyclobutyl]carbamate as a white solid.

Step 4: tert-butyl N-trans-3-[4-(1-hydroxyethyl)-1H-pyrazol-1-yl]cyclobutyl]carbamate: into a 100-mL round-bottom flask purged and maintained with an inert atmosphere of nitrogen, was placed a solution of tert-butyl N-trans-3-(4-formyl-1H-pyrazol-1-yl)cyclobutyl]carbamate (750 mg, 2.83 mmol, 1.00 eq.) in tetrahydrofuran (50 mL). This was followed by the addition of methyl magnesium bromide (3 mL, 3.00 eq., 3 mol/L) dropwise with stirring at 0° C. in 10 min. The resulting solution was stirred for 16 hours at 25° C. The reaction was then quenched by the addition of 100 mL of NH₄Cl aqueous. The resulting solution was extracted with ethyl acetate (3×100 mL) and the organic layers combined. The resulting mixture was washed with brine (2×200 mL), dried and concentrated under vacuum. This resulted in 600 mg (75%) of tert-butyl N-trans-3-[4-(1-hydroxyethyl)-1H-pyrazol-1-yl]cyclobutyl] carbamate as yellow oil.

Step 5: 1-[1-trans-3-aminocyclobutyl]-1H-pyrazol-4-yl]ethan-1-ol: into a 50-mL round-bottom flask, was placed a solution of tert-butyl N-[(1r,3r)-3-[4-(1-hydroxyethyl)-1H-pyrazol-1-yl]cyclobutyl]carbamate (600 mg, 2.13 mmol, 1.00 eq.) in dichloromethane (15 mL) and trifluoroacetic acid (3 mL). The resulting solution was stirred for 2 hours at 25° C. The resulting mixture was concentrated under vacuum. This resulted in 226 mg (crude) of 1-[1-[trans-3-aminocyclobutyl]-1H-pyrazol-4-yl]ethan-1-ol as yellow oil.

Amine 34 and 35: 1-(1-((R)-trans-3-aminocyclobutyl)-1H-pyrazol-5-yl)ethan-1-ol hydrochloride and 1-(1-((S)-trans-3-aminocyclobutyl)-1H-pyrazol-5-yl)ethan-1-ol hydrochloride

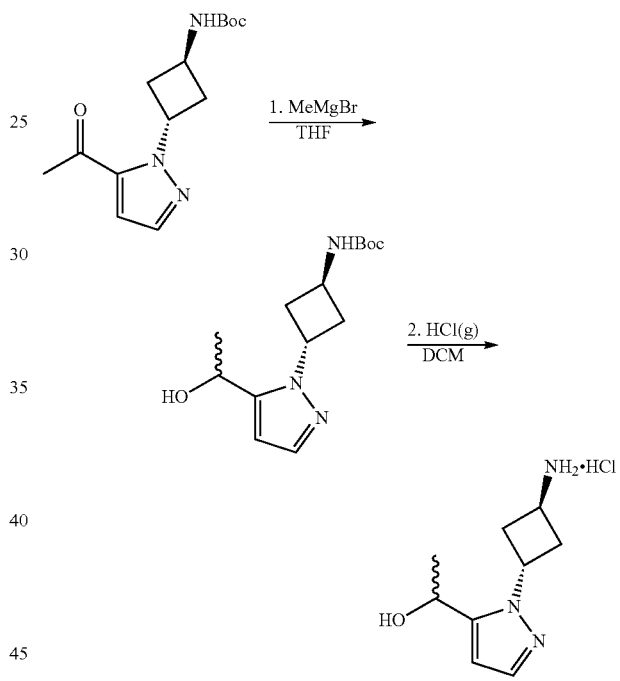

Step 1: tert-butyl N-[trans-3-[3-(1-hydroxyethyl)-1H-pyrazol-1-yl]cyclobutyl]carbamate: Into a 50-mL 3-necked round-bottom flask purged and maintained with an inert atmosphere of nitrogen, was placed a solution of tert-butyl N-[trans-3-(3-formyl-1H-pyrazol-1-yl)cyclobutyl]carbamate (486 mg, 1.83 mmol, 1.00 eq.) in tetrahydrofuran (10 mL). This was followed by the addition of MeMgBr (3M) (1.22 mL, 2.00 eq.) dropwise with stirring at 0° C. The resulting solution was stirred for 7 hours at room temperature. The reaction was then quenched by the addition of 10 mL of NH₄Cl aqueous. The resulting solution was extracted with ethyl acetate (3×10 mL) and the organic layers combined. The solution was dried over anhydrous sodium sulfate and concentrated under vacuum. The crude product was purified by Flash-Prep-HPLC with the following conditions (CombiFlash-1): Column, C18 silica gel; mobile phase, MeCN/H₂O=50:50 increasing to MeCN/H₂O=60:40 within 3 min; Detector, UV 254 nm. This resulted in 233 mg (45%) of tert-butyl N-[trans-3-[3-(1-hydroxyethyl)-1H-pyrazol-1-yl]cyclobutyl]carbamate as colorless oil.

Step 2: 1-[1-[trans-3-aminocyclobutyl]-1H-pyrazol-3-yl]ethan-1-ol hydrochloride: into a 50-mL round-bottom flask, was placed a solution of tert-butyl N-[trans-3-[3-(1-hydroxyethyl)-1H-pyrazol-1-yl]cyclobutyl]carbamate (300 mg, 1.07 mmol, 1.00 eq.) in dichloromethane (10 mL) and hydrogen chloride gas was bubbled into the solution. The resulting solution was stirred for 5 hours at room temperature. The resulting solution was diluted with 20 mL of water. The resulting solution was washed with ethyl acetate (2×20 mL) and the aqueous layer was concentrated under vacuum. This resulted in 271 mg (crude) of 1-[1-[trans-3-aminocyclobutyl]-1H-pyrazol-3-yl]ethan-1-ol hydrochloride as yellow oil.

Amine 36 and 37: (5-(trans-3-aminocyclobutyl)-1,2,4-oxadiazol-3-yl)methanol and (5-(cis-3-aminocyclobutyl)-1,2,4-oxadiazol-3-yl)methanol temperature. The reaction was then quenched by the addition of water. The resulting solution was extracted with 3×100 mL of ethyl acetate and the organic layers combined and dried over anhydrous sodium sulfate and concentrated under vacuum. The residue was applied onto a silica gel column with ethyl acetate/petroleum ether (1:1). This resulted in 6 g (30%) of methyl 3-(1,3-dioxo-2,3-dihydro-1H-isoindol-2-yl)cyclobutane-1-carboxylate as a white solid. $^1$H NMR (300 MHz, CDCl$_3$): δ 7.85-7.81 (m, 2H), 7.75-7.70 (m, 2H), 5.09-5.03 (t, J=8.7 Hz, 1H), 3.32-3.29 (m, 1H), 3.18-3.10 (m, 2H), 2.67-2.59 (m, 2H), 1.31-1.24 (m, 3H). LC-MS: (M+H)$^+$=260.

Step 2: 3-(1,3-dioxo-2,3-dihydro-1H-isoindol-2-yl)cyclobutane-1-carboxylic acid: into a 250-mL round-bottom flask, was placed a solution of methyl 3-(1,3-dioxo-2,3-dihydro-1H-isoindol-2-yl)cyclobutane-1-carboxylate (6 g,

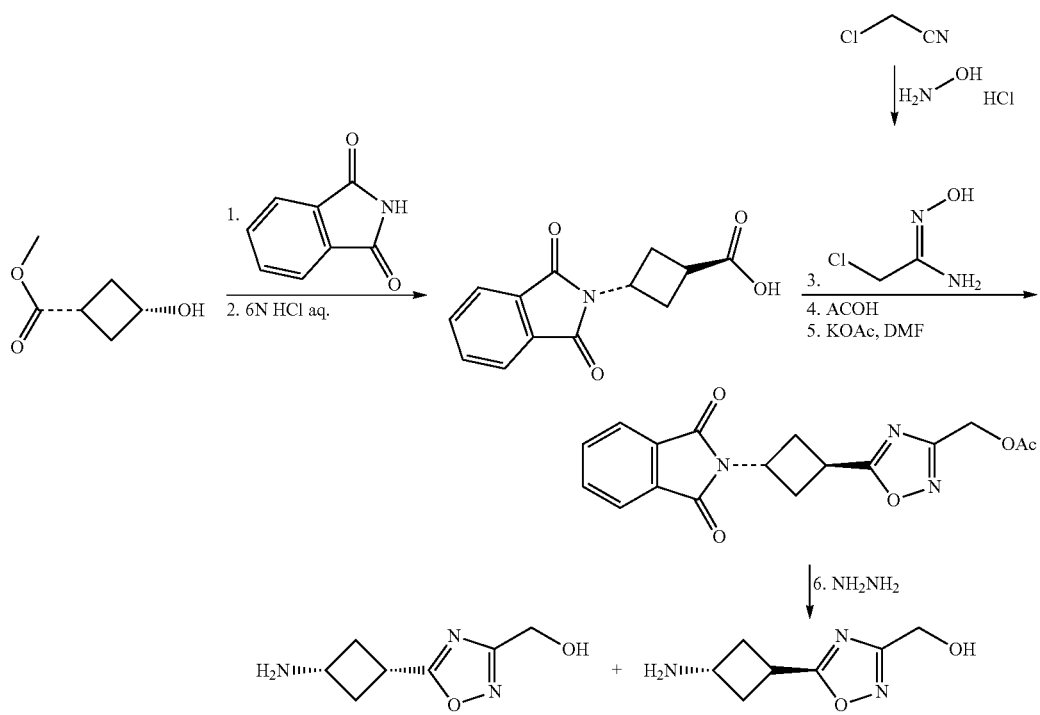

Step 1a: (Z)-2-chloro-N-hydroxyethenimidamide: into a 100-mL round-bottom flask, was placed a solution of 2-chloroacetonitrile (8 g, 105.96 mmol, 1.00 eq.) in water (28 mL). To the solution were added NH$_2$OH.HCl (7.36 g, 1.00 eq.) and Na$_2$CO$_3$ (5.6 g, 52.32 mmol, 0.50 eq.). The resulting solution was stirred for 1 hour at room temperature. The resulting solution was diluted with water. The resulting solution was extracted with ethyl acetate (3×100 mL) and the organic layer was dried and concentrated under vacuum. This resulted in 4 g (35%) of (Z)-2-chloro-N-hydroxyethenimidamide as a yellow solid. LC-MS: (M+H)+=109.

Step 1: methyl 3-(1,3-dioxo-2,3-dihydro-1H-isoindol-2-yl)cyclobutane-1-carboxylate: into a 1000-mL round-bottom flask, was placed a solution of methyl 3-hydroxycyclobutane-1-carboxylate (10 g, 76.88 mmol, 1.00 eq.) in tetrahydrofuran (500 mL), 2,3-dihydro-1H-isoindole-1,3-dione (13.2 g, 89.7 mmol, 1.20 eq.), triphenyl phosphine (23.6 g, 90.0 mmol, 1.20 eq.). This was followed by the addition of DEAD (21 g, 120.6 mmol, 1.50 eq.) dropwise with stirring. The resulting solution was stirred for 3 h at room 23.14 mmol, 1.00 eq.) in dioxane (100 mL). To the solution was added 6N hydrogen chloride aqueous (30 mL). The resulting solution was stirred for 3 hours at 90° C. in an oil bath. The resulting mixture was concentrated under vacuum. This resulted in 5 g (crude) of 3-(1,3-dioxo-2,3-dihydro-1H-isoindol-2-yl)cyclobutane-1-carboxylic acid as a white solid. LC-MS: (M+H)$^+$=246.

Step 3: N-[(1E)-2-chloro-1-(hydroxyimino)ethyl]-3-(1,3-dioxo-2,3-dihydro-1H-isoindol-2-yl)cyclobutane-1-carboxamide: into a 250-mL round-bottom flask, was placed a solution of 3-(1,3-dioxo-2,3-dihydro-1H-isoindol-2-yl)cyclobutane-1-carboxylic acid (5 g, 20.38 mmol, 1.00 eq.) in dichloromethane (100 mL). To the mixture were added (Z)-2-chloro-N-hydroxyethenimidamide (2.6 g, 24.00 mmol, 1.20 eq.), HATU (9.2 g, 38.16 mmol, 1.20 eq.) and DIEA (8 g, 60.36 mmol, 3.00 eq.) with stirring. The resulting solution was stirred for 2 hours at room temperature. The reaction was then quenched by the addition of water. The resulting solution was extracted with dichloromethane (3×100 mL) and the organic layer was dried over anhydrous sodium sulfate and concentrated under vacuum. The residue was applied onto a silica gel column with ethyl acetate/hexane (1:1). This resulted in 4.4 g (64%) of N-[(1E)-2-chloro-1-(hydroxyimino)ethyl]-3-(1,3-dioxo-2,3-dihydro-1H-isoindol-2-yl)cyclobutane-1-carboxamide as a white solid. LC-MS: [M+H]+=336.

Step 4: 2-[3-[3-(chloromethyl)-1,2,4-oxadiazol-5-yl]cyclobutyl]-2,3-dihydro-1H-isoindole-1,3-dione: into a 10-mL vial, was placed a solution of N-[(1E)-2-chloro-1-(hydroxyimino)ethyl]-3-(1,3-dioxo-2,3-dihydro-1H-isoindol-2-yl)cyclobutane-1-carboxamide (4 g, 11.92 mmol, 1.00 eq.) in AcOH (15 mL). The final reaction mixture was irradiated with microwave radiation for 30 min at 150° C. The resulting mixture was concentrated under vacuum. The residue was applied onto a silica gel column with ethyl acetate/hexane (1:1). This resulted in 2 g (53%) of 2-[3-[3-(chloromethyl)-1,2,4-oxadiazol-5-yl]cyclobutyl]-2,3-dihydro-1H-isoindole-1,3-dione as a white solid. LC-MS: [M+H]+=318.

Step 5: [5-[3-(1,3-dioxo-2,3-dihydro-1H-isoindol-2-yl)cyclobutyl]-1,2,4-oxadiazol-3-yl]methyl acetate: into a 100-mL round-bottom flask, was placed a solution of 2-[3-[3-(chloromethyl)-1,2,4-oxadiazol-5-yl]cyclobutyl]-2,3-dihydro-1H-isoindole-1,3-dione (2 g, 6.60 mmol, 1.00 eq.) and potassium acetate (1.3 g, 13.22 mmol, 2.00 eq.) in DMF (50 mL). The resulting solution was stirred for 2 hours at 60° C. in an oil bath. The resulting mixture was concentrated under vacuum. The residue was applied onto a silica gel column with ethyl acetate/petroleum ether (1:1). This resulted in 1.4 g (62%) of [5-[3-(1,3-dioxo-2,3-dihydro-1H-isoindol-2-yl)cyclobutyl]-1,2,4-oxadiazol-3-yl]methyl acetate as yellow oil. LC-MS: [M+H]+=342.

Step 6: [5-(3-aminocyclobutyl)-1,2,4-oxadiazol-3-yl]methanol: into a 100-mL round-bottom flask, was placed a solution of [5-[3-(1,3-dioxo-2,3-dihydro-1H-isoindol-2-yl)cyclobutyl]-1,2,4-oxadiazol-3-yl]methyl acetate (1.4 g, 4.1 mmol, 1.00 eq.) in ethanol (40 mL). To the solution was added hydrazine (1 mL). The resulting solution was stirred for 3 hours at 60° C. in an oil bath. The solids were filtered out. The resulting mixture was concentrated under vacuum. This resulted in 1 g (crude) of [5-(3-aminocyclobutyl)-1,2,4-oxadiazol-3-yl]methanol as a white solid. LC-MS: [M+H]+=170.

Amine 38 and 39: (3-(cis-3-aminocyclobutyl)-1,2,4-oxadiazol-5-yl)methanol and (3-(trans-3-aminocyclobutyl)-1,2,4-oxadiazol-5-yl)methanol

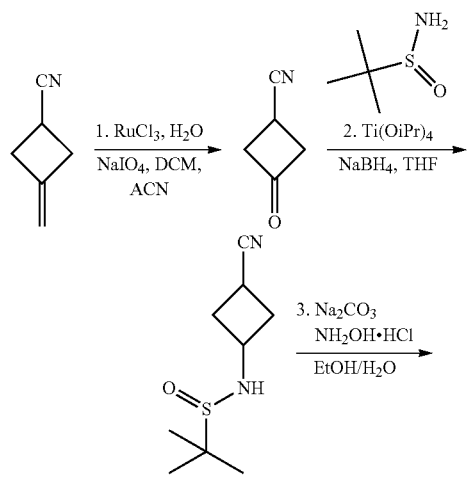

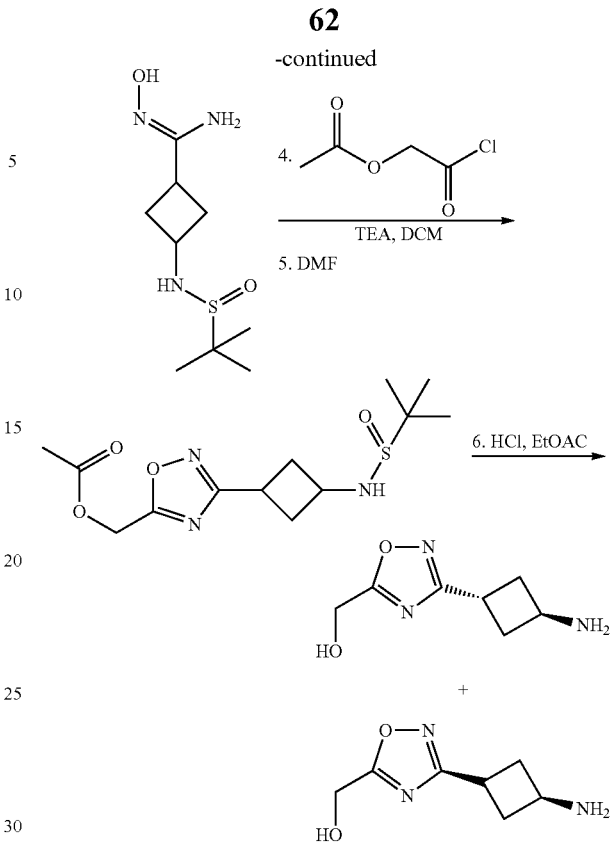

Step 1: oxocyclobutane-1-carbonitrile: into a 500-mL 3-necked round-bottom flask, was placed a solution of 3-methylidenecyclobutane-1-carbonitrile (1.5 g, 16.11 mmol, 1.00 eq.) and RuCl$_3$.H$_2$O (360 mg, 1.60 mmol, 0.10 eq.) in DCM/ACN/H$_2$O (60/60/90 mL). This was followed by the addition of sodium periodate (5.2 g, 24.31 mmol, 1.50 eq.), in portions at 10° C. in 15 min. The resulting solution was stirred for 2 hours at 25° C. The solids were filtered out. The resulting solution was extracted with dichloromethane (3×100 mL) and the organic layers combined. The resulting mixture was washed with brine (2×200 mL), dried over anhydrous sodium sulfate and concentrated under vacuum. The residue was applied onto a silica gel column with ethyl acetate/petroleum ether (1:1). This resulted in 1.1 g (72%) of 3-oxocyclobutane-1-carbonitrile as a yellow solid.

Step 2: N-(3-cyanocyclobutyl)-2-methylpropane-2-sulfinamide: into a 500-mL round-bottom flask, was placed a solution of 3-oxocyclobutane-1-carbonitrile (4 g, 42.06 mmol, 1.00 eq.) tetra(propan-2-yloxy)titanium (14.16 g, 62.90 mmol, 1.50 eq.) and 2-methylpropane-2-sulfinamide (6.12 g, 50.49 mmol, 1.20 eq.) in tetrahydrofuran (200 mL). The resulting solution was stirred for 16 hours at 65° C. The reaction was cooled to 25° C. Then NaBH$_4$ (3.2 g, 84.60 mmol, 2.00 eq.) was added. The mixture was stirred for 2 hours at 25° C. The reaction was then quenched by the addition of 200 mL of water. The solids were filtered out and the resulting solution was extracted with ethyl acetate (2×200 mL) and the organic layers were combined. The resulting mixture was washed with brine (2×300 mL), dried over sodium sulfate and concentrated under vacuum. This resulted in 7.2 g (85%) of N-(3-cyanocyclobutyl)-2-methylpropane-2-sulfinamide as a yellow solid.

Step 3: (Z)—N-hydroxy-3-[(2-methylpropane-2-sulfinyl)amino]cyclobut-1-carboximidamide: into a 500-mL round-bottom flask, was placed a solution of N-(3-cyanocyclobutyl)-2-methylpropane-2-sulfinamide (7.2 g, 35.95 mmol, 1.00 eq.) in ethanol/H$_2$O (200/70 mL). To the solution were added NH$_2$OH—HCl (5 g, 71.94 mmol, 2.00 eq.) and sodium carbonate (11.43 g, 107.84 mmol, 3.00 eq.). The resulting solution was stirred for 2 hours at 80° C. The resulting solution was diluted with 400 mL of water. The resulting solution was extracted with ethyl acetate (2×300 mL) and the organic layers combined. The resulting mixture was washed with brine (2×400 mL), dried over anhydrous sodium sulfate and concentrated under vacuum. This resulted in 5 g (60%) of (Z)—N-hydroxy-3-[(2-methylpropane-2-sulfinyl)amino]cyclobut-1-carboximidamide as yellow oil. LC-MS [M+H]+=234.

Step 4: [[Z-hydroxyimino)([3-[(2-methylpropane-2-sulfinyl)amino]cyclobutyl])methyl]carbamoyl]methyl acetate: into a 250-mL round-bottom flask, was placed a solution of (Z)—N-hydroxy-3-[(2-methylpropane-2-sulfinyl)amino]cyclobut-1-carboximidamide (3.7 g, 15.86 mmol, 1.00 eq.) in dichloromethane (mL). To the solution were added TEA (3.2 g, 31.62 mmol, 2.00 eq.) and 2-chloro-2-oxoethyl acetate (2.6 g, 19.04 mmol, 1.20 eq.). The resulting solution was stirred for 1 hour at 25° C. The resulting solution was diluted with 300 mL of H$_2$O and then it was extracted with ethyl acetate (2×500 mL) and the organic layers combined. The resulting mixture was washed with brine (2×500 mL), dried over anhydrous sodium sulfate and concentrated under vacuum. The residue was applied onto a silica gel column with ethyl acetate/petroleum ether (1:1). This resulted in 3.7 g (70%) of [[Z-hydroxyimino)([3-[(2-methylpropane-2-sulfinyl)amino]cyclobutyl])methyl]carbamoyl]methyl acetate as a yellow solid. LC-MS [M+H]$^+$=334.

Step 5: (3-[3-[(2-methylpropane-2-sulfinyl)amino]cyclobutyl]-1,2,4-oxadiazol-5-yl)methyl acetate: into a 50-mL round-bottom flask, was placed a solution of [[(Z)-(hydroxyimino)([3-[(2-methylpropane-2-sulfinyl)amino]cyclobutyl])methyl]carbamoyl]methyl acetate (3.2 g, 9.60 mmol, 1.00 eq.) in DMF (20 mL). The resulting solution was stirred for 2 hours at 100° C. The mixture was concentrate and the crude product was purified by Flash-Prep-HPLC with the following conditions (IntelFlash-1): Column, C18; mobile phase, X:H$_2$O Y:ACN=80/20 increasing to X:H$_2$O Y:ACN=20/80 within 20 min; Detector, UV 220 nm. This resulted in 1.2 g (40%) of (3-[3-[(2-methylpropane-2-sulfinyl)amino]cyclobutyl]-1,2,4-oxadiazol-5-yl)methyl acetate as a yellow solid. LC-MS [M+H]$^+$=332.

Step 6: [3-(3-aminocyclobutyl)-1,2,4-oxadiazol-5-yl]methyl acetate: into a 100-mL 3-necked round-bottom flask, was placed a solution of (3-[3-[(2-methylpropane-2-sulfinyl)amino]cyclobutyl]-1,2,4-oxadiazol-5-yl)methyl acetate (1.2 g, 3.80 mmol, 1.00 eq.) in ethyl acetate (50 mL). To the above solution, the HCl gas was introduced. The resulting solution was stirred for 2 hours at 25° C. The resulting mixture was concentrated under vacuum. This resulted in 1.1 g (crude) of [3-(3-aminocyclobutyl)-1,2,4-oxadiazol-5-yl]methyl acetate as yellow oil. LC-MS: (M+H)$^+$=212.

Amine 40 and 41: 2-(cis-3-aminocyclobutyl)ethan-1-ol hydrochloride and 2-(trans-3-aminocyclobutyl)ethan-1-ol hydrochloride

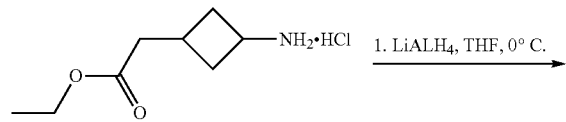

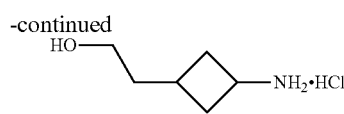

Step 1: 2-(3-aminocyclobutyl)ethan-1-ol hydrochloride: a solution of ethyl 2-(3-aminocyclobutyl)acetate hydrochloride (2.5 g, 12.91 mmol, 1.00 eq.) in tetrahydrofuran (10 mL) was placed in a 100-mL round-bottom flask. This was followed by the addition of LiAlH$_4$ (2.4 g, 63.24 mmol, 4.90 eq.) in several batches at 0° C. The resulting solution was stirred for 1 hours at room temperature. The reaction was then quenched by the addition of 2 g of Na$_2$SO$_4$.H$_2$O. The solids were filtered out. The resulting mixture was concentrated under vacuum. This resulted in 1.8 g (crude) of 2-(3-aminocyclobutyl)ethan-1-ol hydrochloride as a yellow solid. LC-MS: (M+H)$^+$=152.

Example 2

CFTR Activity Assays i. Ussing Measurements

As discussed above, Ussing measurements are used to measure CFTR activity. In this method, primary lung epithelial cells (hBEs) homozygous for the Cystic Fibrosis-causing ΔF508 mutation are differentiated for a minimum of 4 weeks in an air-liquid interface on SnapWell filter plates prior to the Ussing measurements. Cells are apically mucus-washed for 30 minutes prior to treatment with compounds. The basolateral media is removed and replaced with media containing the compound of interest diluted to its final concentration from DMSO stocks. Treated cells are incubated at 37° C. and 5% CO$_2$ for 24 hours. At the end of the treatment period, the cells on filters are transferred to the Ussing chamber and equilibrated for 30 minutes. The short-circuit current is measured in voltage clamp-mode (V$_{hold}$=0 mV), and the entire assay is conducted at a temperature of 36° C.-36.5° C. Once the voltages stabilized, the chambers are clamped, and data is recorded by pulse readings every 5 seconds. Following baseline current stabilization, the following additions can be applied and the changes in current and resistance of the cells can be monitored:
1. Benzamil to the apical chamber to inhibit ENaC sodium channel.
2. Forskolin to both chambers to activate ΔF508-CFTR by phosphorylation.
3. Genistein to both chambers to potentiate ΔF508-CFTR channel opening.
4. CFTRinh-172 to the apical chamber to inhibit ΔF508-CFTR Cl-conductance.

The inhibitable current (that current that is blocked by CFTRinh-172) is measured as the specific activity of the ΔF508-CFTR channel, and increases in response to compound in this activity over that observed in vehicle-treated samples are identified as the correction of ΔF508-CFTR function imparted by the compound tested.

ii. hBE Equivalent Current (Ieq) Assay

Primary lung epithelial cells homozygous for the Cystic Fibrosis-causing ΔF508 mutation are differentiated for a minimum of 4 weeks in an air-liquid interface on Costar 24 well HTS filter plates prior to the equivalent current (Ieq) measurements. Cells are apically mucus-washed for 30 minutes 24 h prior to treatment with compounds. The basolateral media is removed and replaced with media containing the compound of interest diluted to its final concentration from DMSO stocks. Treated cells are incubated at 37° C. and 5% $CO_2$ for 24 hours. At the end of the treatment period, the media is changed to the Ieq experimental solution for 30 minutes before the experiment and plates are maintained in a $CO_2$-free incubator during this period. The plates containing the cells are then placed in pre-warmed heating blocks at 36° C.±0.5 for 15 minutes before measurements are taken. The transepithelial voltage ($V_T$) and conductance ($G_T$) are measured using a custom 24 channel current clamp (TECC-24) with 24 well electrode manifold. The Ieq assay measurements were made following additions with standardized time periods:
  1. The baseline $V_T$ and $G_T$ values are measured for approximately 20 minutes.
  2. Benzamil is added to block ENaC for 15 minutes.
  3. Forskolin plus VX-770 are added to maximally activate ΔF508-CFTR for 27 minutes.
  4. Bumetanide is added to inhibit the $NaK_2Cl$ cotransporter and shut-off secretion of chloride.

The activity data captured is the area under the curve (AUC) for the traces of the equivalent chloride current. The AUC is collected from the time of the forskolin/VX-770 addition until the inhibition by bumetanide addition. Correction in response to compound treatment is scored as the increase in the AUC for compound-treated samples over that of vehicle-treated samples.

Example 3 i. Ussing Measurements

As discussed above, Ussing measurements can be used to measure CFTR activity. In this method, primary lung epithelial cells (hBEs) with a Cystic fibrosis causing class I mutation are differentiated for a minimum of 4 weeks in an air-liquid interface on SnapWell™ filter plates prior to the Ussing measurements. Cells are apically mucus-washed for 30 minutes prior to treatment with compounds. The basolateral media is removed and replaced with media containing the compound of interest diluted to its final concentration from DMSO or aqueous stocks. Treated cells are incubated at 37° C. and 5% $CO_2$ for 24 hours. At the end of the treatment period, the cells on filters are transferred to the Ussing chamber and equilibrated for 30 minutes. The short-circuit current is measured in voltage clamp-mode ($V_{hold}=0$ mV), and the entire assay is conducted at a temperature of 36° C.-36.5° C. Once the voltages stabilize, the chambers are clamped, and data are recorded by pulse readings every 5 seconds. Following baseline current stabilization, the following additions are applied and the changes in current and resistance of the cells are monitored:
  1. Benzamil to the apical chamber to inhibit ENaC sodium channel.
  2. Forskolin to both chambers to activate ΔF508-CFTR by phosphorylation.
  3. Ivacaftor or Genistein to the apical chamber to potentiate ΔF508-CFTR channel opening.
  4. CFTRinh-172 to the apical chamber to inhibit ΔF508-CFTR Cl-conductance.

The forskolin-sensitive current and inhibitable current (that potentiated current that is blocked by CFTRinh-172) are measured as the specific activity of the ΔF508-CFTR channel, and increase in response to compound in this activity over that observed in vehicle-treated samples are identified as the correction of ΔF508-CFTR function imparted by the compound tested.

Example 4 i. Ussing Measurements

As discussed above, Ussing measurements can be used to measure CFTR activity. In this method, primary lung epithelial cells (hBEs) with a Cystic Fibrosis-causing class III mutation are differentiated for a minimum of 4 weeks in an air-liquid interface on SnapWell™ filter plates prior to the Ussing measurements. Cells are apically mucus-washed for 30 minutes prior to treatment with compounds. The basolateral media is removed and replaced with media containing the compound of interest diluted to its final concentration from DMSO stocks. Treated cells are incubated at 37° C. and 5% $CO_2$ for 24 hours. At the end of the treatment period, the cells on filters are transferred to the Ussing chamber and equilibrated for 30 minutes. The short-circuit current is measured in voltage clamp-mode ($V_{hold}=0$ mV), and the entire assay is conducted at a temperature of 36° C.-36.5° C. Once the voltages stabilize, the chambers are clamped, and data is recorded by pulse readings every 5 seconds. Following baseline current stabilization, the following additions are applied and the changes in current and resistance of the cells is monitored:
  1. Benzamil to the apical chamber to inhibit ENaC sodium channel.
  2. Forskolin to both chambers to activate ΔF508-CFTR by phosphorylation.
  3. VX-770 or Genistein to the apical chamber to potentiate ΔF508-CFTR channel opening.
  4. CFTRinh-172 to the apical chamber to inhibit ΔF508-CFTR Cl-conductance.

The forskolin-sensitive current and inhibitable current (that potentiated current that is blocked by CFTRinh-172) are measured as the specific activity of the ΔF508-CFTR channel, and increase in response to compound in this activity over that observed in vehicle-treated samples are identified as the correction of ΔF508-CFTR function imparted by the compound tested.

Example 5 i. Ussing Measurements

As discussed above, Ussing measurements can be used to measure CFTR activity. In this method, primary lung epithelial cells (hBEs) with a Cystic Fibrosis-causing class V mutation are differentiated for a minimum of 4 weeks in an air-liquid interface on SnapWell™ filter plates prior to the Ussing measurements. Cells are apically mucus-washed for 30 minutes prior to treatment with compounds. The basolateral media is removed and replaced with media containing the compound of interest diluted to its final concentration from DMSO stocks. Treated cells are incubated at 37° C. and 5% $CO_2$ for 24 hours. At the end of the treatment period, the cells on filters are transferred to the Ussing chamber and equilibrated for 30 minutes. The short-circuit current is measured in voltage clamp-mode ($V_{hold}=0$ mV), and the entire assay is conducted at a temperature of 36° C.-36.5° C. Once the voltages stabilize, the chambers are clamped, and data is recorded by pulse readings every 5 seconds. Following baseline current stabilization, the following additions are applied and the changes in current and resistance of the cells is monitored:
  1. Benzamil to the apical chamber to inhibit ENaC sodium channel.
  2. Forskolin to both chambers to activate ΔF508-CFTR by phosphorylation.

3. VX-770 or Genistiein to the apical chamber to potentiate ΔF508-CFTR channel opening.
4. CFTRinh-172 to the apical chamber to inhibit ΔF508-CFTR Cl-conductance.

The forskolin-sensitive current and inhibitable current (that potentiated current that is blocked by CFTRinh-172) are measured as the specific activity of the ΔF508-CFTR channel, and increases in response to compound in this activity over that observed in vehicle-treated samples are identified as the correction of ΔF508-CFTR function imparted by the compound tested.

ii. hBE Equivalent Current (Ieq) Assay

Primary lung epithelial cells homozygous for the Cystic Fibrosis-causing ΔF508 mutation are differentiated for a minimum of 4 weeks in an air-liquid interface on Costar 24 well HTS filter plates prior to the equivalent current (Ieq) measurements. Cells are apically mucus-washed for 30 minutes 24 h prior to treatment with compounds. The basolateral media is removed and replaced with media containing the compound of interest diluted to its final concentration from DMSO stocks. Treated cells are incubated at 37° C. and 5% $CO_2$ for 24 hours. At the end of the treatment period, the media is changed to the Ieq experimental solution for 30 minutes before the experiment and plates are maintained in a $CO_2$-free incubator during this period. The plates containing the cells are then placed in pre-warmed heating blocks at 36° C.±0.5 for 15 minutes before measurements are taken. The transepithelial voltage ($V_T$) and conductance ($G_T$) are measured using a custom 24 channel current clamp (TECC-24) with 24 well electrode manifold. The Ieq assay measurements are made following additions with standardized time periods:

1. The baseline $V_T$ and $G_T$ values are measured for approximately 20 minutes.
2. Benzamil is added to block ENaC for 15 minutes.
3. Forskolin plus VX-770 (ivacaftor) are added to maximally activate ΔF508-CFTR for 27 minutes.
4. Bumetanide is added to inhibit the $NaK_2Cl$ cotransporter and shut-off secretion of chloride.

The activity data captured is the area under the curve (AUC) for the traces of the equivalent chloride current. The AUC is collected from the time of the forskolin/VX-770 addition until the inhibition by bumetanide addition. Correction in response to compound treatment is scored as the increase in the AUC for compound-treated samples over that of vehicle-treated samples.

While this invention has been particularly shown and described with references to preferred embodiments thereof, it will be understood by those skilled in the art that various changes in form and details may be made therein without departing from the scope of the invention encompassed by the appended claims.

INCORPORATION BY REFERENCE

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

What is claimed is:
1. A compound represented by:

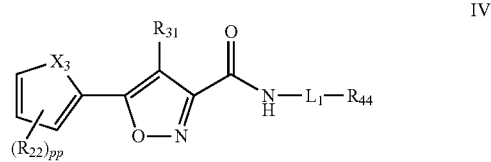

or a pharmaceutically acceptable salts or stereoisomers thereof, wherein;
$X_3$ is selected from the group consisting of O, S, and $NR_{hh}$;
pp is 1, 2, or 3;
$R_{22}$ is independently selected for each occurrence from the group consisting of hydrogen and halogen;
$R_{31}$ is selected from the group consisting of hydrogen and halogen;
$L_1$ is selected from the group consisting of $C_{3-5}$cycloalkylene, $C_{3-6}$cycloalkylene-$C_{1-4}$alkylene, $C_{3-6}$cycloalkylene-$C_{0-2}$alkylene-S(O)$_w$—NR$_{hh}$, and $C_{3-6}$cycloalkylene-$C_{0-2}$alkylene NR$_{hh}$—S(O)$_w$—, wherein $L_1$ may be optionally substituted by one, two or three substituents each independently selected from the group consisting of halogen, hydroxyl, and $C_{1-3}$alkyl (optionally substituted by one, two or three substituents each selected independently from $R_{ff}$);
$R_{44}$ is selected from the group consisting of heterocycle and a 5-6 membered monocyclic heteroaryl or 8-10 membered bicyclic heteroaryl having one, two or three heteroatoms each independently selected from the group consisting of O, N, and S; wherein the heterocycle and the heteroaryl may be optionally substituted by one or two substituents each selected independently from $R_{gg}$;
$R_{ff}$ is independently selected for each occurrence from the group consisting of halogen, hydroxyl, $C_{1-4}$alkyl, $C_{1-4}$alkoxy, $C_{2-4}$alkenyl, $C_{3-6}$cycloalkyl, —NR'R", —NR'—S(O)$_w$—$C_{1-3}$alkyl, S(O)$_w$—NR'R", and —S(O)$_w$—$C_{1-3}$alkyl, where w is 0, 1, or 2, wherein $C_{1-4}$alkyl, $C_{1-4}$alkoxy, $C_{2-4}$alkenyl and $C_{3-6}$cycloalkyl may be optionally substituted by one, two or three substituents each independently selected from the group consisting of halogen, hydroxyl, —NR'R", —NR'—S(O)$_w$—$C_{1-3}$alkyl, S(O)$_w$—NR'R", and —S(O)$_w$—$C_{1-3}$alkyl;
$R_{gg}$ is independently selected for each occurrence from the group consisting of halogen, hydroxyl, $C_{1-6}$alkyl, $C_{1-6}$alkoxy, $C_{2-6}$alkenyl, $C_{3-6}$cycloalkyl, —NR'R", —NR'—S(O)$_w$—$C_{1-3}$alkyl, S(O)$_w$—NR'R", —O—Si(R''')$_3$, and —S(O)$_w$—$C_{1-3}$alkyl, where w is 0, 1, or 2, wherein C$_{1-6}$alkyl, C$_{1-6}$alkoxy, C$_{2-6}$alkenyl and C$_{3-6}$cycloalkyl may each be optionally substituted by one, two or three substituents each independently selected from the group consisting of halogen, C$_{1-6}$alkyl, C$_{1-6}$alkoxy, hydroxyl, C(O)OH, —C(O)OC$_{1-6}$alkyl, —O—C$_{3-6}$cycloalkyl, —O-heterocycle, —O-heteroaryl, —O-phenyl, —NR'R", —NR'—S(O)$_w$—C$_{1-3}$alkyl, —O—Si(R''')$_3$, S(O)$_w$—NR'R", and —S(O)w-C$_{1-3}$alkyl;

w is 0, 1 or 2;

R$_{hh}$ is independently selected for each occurrence from the group consisting of H, C$_{1-6}$alkyl, and C$_{3-6}$cycloalkyl;

R' and R" are independently selected for each occurrence from the group consisting of H, C$_{1-6}$alkyl and C$_{3-6}$cycloalkyl; and R''' is independently selected for each occurrence from C$_{1-6}$alkyl.

2. The compound of claim 1, wherein L$_1$ is selected from the group consisting of C$_{3-5}$cycloalkylene and C$_{3-6}$cycloalkylene-C$_{1-4}$alkylene.

3. The compound of any one of claims 1, wherein R$_{31}$ is selected from the group consisting of H and F.

4. The compound of any one of claims 1, wherein R$_{22}$, for each occurrence, hydrogen.

5. The compound of claim 1, wherein L$_1$ is C$_4$cycloalkylene.

6. The compound of any one of claims 1, where the compound is represented by:

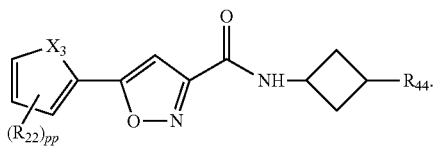

7. The compound of any one of claims 1, wherein R$_{44}$ is a 5-membered heteroaryl having two or three nitrogens.

8. The compound of any one of claims 1, wherein R$_{44}$ is a 5 membered heteroaryl having two nitrogens and an additional heteroatom selected from the group consisting of O and S.

9. The compound of any one of claims 1, wherein R$_{44}$ is substituted on a free carbon by a substituent selected from the group consisting of: a methyl substituted by one, two or three substituents each independently selected from the group consisting of halogen, hydroxyl, methoxy and ethoxy, ethyl substituted by one, two or three substituents each independently selected from the group consisting of halogen, hydroxyl, methoxy and ethoxy, propyl substituted by one, two or three substituents each independently selected from the group consisting of halogen, hydroxyl, methoxy and ethoxy, isopropyl substituted by one, two or three substituents each independently selected from the group consisting of halogen, hydroxyl, methoxy and ethoxy, n-butyl substituted by one, two or three substituents each independently selected from halogen, hydroxyl, methoxy and ethoxy, t-butyl substituted by one, two or three substituents each independently selected from the group consisting of halogen, hydroxyl, methoxy and ethoxy, s-butyl substituted by one, two or three substituents each independently selected from the group consisting of halogen, hydroxyl, methoxy and ethoxy and isobutyl substituted by one, two or three substituents each independently selected from the group consisting of halogen, hydroxyl, methoxy and ethoxy.

10. The compound of any one of claims 1, wherein R$_{44}$ is selected from the group consisting of:

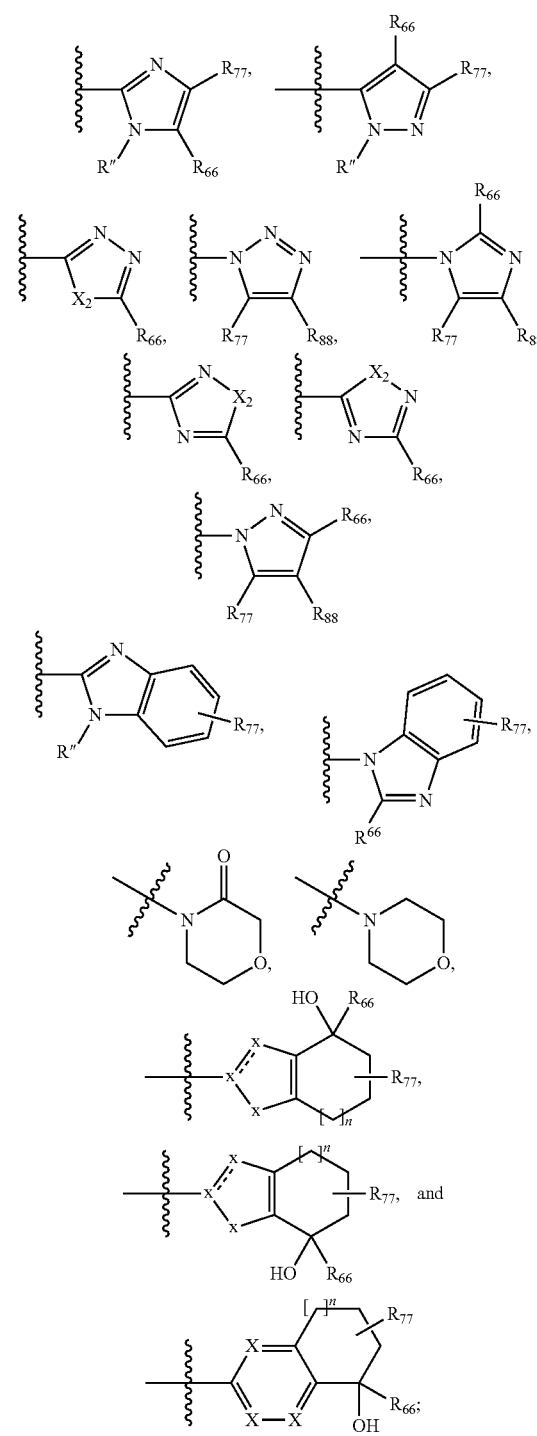

wherein X independently for each occurrence is selected from the group consisting of O, S, NR$_{hh}$, C, C(R$_{88}$), and C(R$_{88}$)(R$_{99}$); X$_2$ is selected from the group consisting of O, S and NR$_{hh}$; R" is selected from the group consisting of H and C$_{1-4}$alkyl, each R$_{66}$, R$_{77}$, R$_{88}$ and R$_{99}$ is independently selected for each occurrence from the group consisting of H and R$_{gg}$, and n is 0, 1, 2, or 3.

11. The compound of claim 10, wherein $R_{44}$ is represented by:

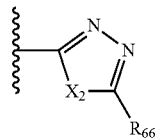

wherein $R_{66}$ is selected from the group consisting of: a methyl substituted by one, two or three substituents each independently selected from the group consisting of halogen, hydroxyl, methoxy and ethoxy, ethyl substituted by one, two or three substituents each independently selected from the group consisting of halogen, hydroxyl, methoxy and ethoxy, propyl substituted by one, two or three substituents each independently selected from the group consisting of halogen, hydroxyl, methoxy and ethoxy, isopropyl substituted by one, two or three substituents each independently selected from the group consisting of halogen, hydroxyl, methoxy and ethoxy, n-butyl substituted by one, two or three substituents each independently selected from the group consisting of halogen, hydroxyl, methoxy and ethoxy, t-butyl substituted by one, two or three substituents each independently selected from the group consisting of halogen, hydroxyl, methoxy and ethoxy, s-butyl substituted by one, two or three substituents each independently selected from the group consisting of halogen, hydroxyl, methoxy and ethoxy, and isobutyl substituted by one, two or three substituents each independently selected from the group consisting of halogen, hydroxyl, methoxy and ethoxy.

12. A compound represented by:

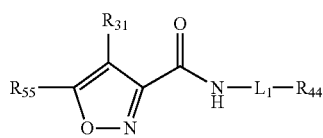

and pharmaceutically acceptable salts, stereoisomers, and prodrugs thereof, wherein;

$R_{55}$ is pyridinyl;

$R_{31}$ is selected from the group consisting of hydrogen and halogen;

$L_1$ is selected from the group consisting of $C_{3-6}$cycloalkylene, $C_{3-6}$cycloalkylene-$C_{1-4}$alkylene, $C_{3-6}$cycloalkylene-$C_{0-2}$alkylene-S(O)$_w$—NR$_{hh}$, and $C_{3-6}$cycloalkylene-$C_{0-2}$alkylene NR$_{hh}$—S(O)$_w$—, wherein $L_1$ may be optionally substituted by one, two or three substituents each independently selected from the group consisting of halogen, hydroxyl, and $C_{1-3}$alkyl (optionally substituted by one, two or three substituents each selected independently from $R_{ff}$);

$R_{44}$ is selected from the group consisting of heterocycle and a 5-6 membered monocyclic heteroaryl or 8-10 membered bicyclic heteroaryl having one, two or three heteroatoms each independently selected from the group consisting of O, N, and S; wherein the heterocycle and the heteroaryl may be optionally substituted by one or two substituents each selected independently from $R_{gg}$;

$R_{ff}$ is independently selected for each occurrence from the group consisting of halogen, hydroxyl, $C_{1-4}$alkyl, $C_{1-4}$alkoxy, $C_{2-4}$alkenyl, $C_{3-6}$cycloalkyl, —NR'R", —NR'—S(O)$_w$—$C_{1-3}$alkyl, S(O)$_w$—NR'R", and —S(O)$_w$—$C_{1-3}$alkyl, where w is 0, 1, or 2, wherein $C_{1-4}$alkyl, $C_{1-4}$alkoxy, $C_{2-4}$alkenyl and $C_{3-6}$cycloalkyl may be optionally substituted by one, two or three substituents each independently selected from the group consisting of halogen, hydroxyl, —NR'R", —NR'—S(O)$_w$—$C_{1-3}$alkyl, S(O)$_w$—NR'R", and —S(O)$_w$—$C_{1-3}$alkyl;

$R_{gg}$ is independently selected for each occurrence from the group consisting of halogen, hydroxyl, $C_{1-6}$alkyl, $C_{1-6}$alkoxy, $C_{2-6}$alkenyl, $C_{3-6}$cycloalkyl, —NR'R", —NR'—S(O)$_w$—$C_{1-3}$alkyl, S(O)$_w$—NR'R", —O—Si(R''')$_3$, and —S(O)$_w$—$C_{1-3}$alkyl, where w is 0, 1, or 2, wherein $C_{1-6}$alkyl, $C_{1-6}$alkoxy, $C_{2-6}$alkenyl and $C_{3-6}$cycloalkyl may each be optionally substituted by one, two or three substituents each independently selected from the group consisting of halogen, $C_{1-6}$alkyl, $C_{1-6}$alkoxy, hydroxyl, C(O)OH, —C(O)OC$_{1-6}$alkyl, —O—$C_{3-6}$cycloalkyl, —O-heterocycle, —O-heteroaryl, —O-phenyl, —NR'R", —NR'—S(O)$_w$—$C_{1-3}$alkyl, —O—Si(R''')$_3$, S(O)$_w$—NR'R", and —S(O)$_w$—$C_{1-3}$alkyl;

w is 0, 1 or 2;

$R_{hh}$ is independently selected for each occurrence from the group consisting of H, $C_{1-6}$alkyl, and $C_{3-6}$cycloalkyl;

R' and R" are independently selected for each occurrence from the group consisting of H, $C_{1-6}$alkyl and $C_{3-6}$cycloalkyl; and R''' is independently selected for each occurrence from $C_{1-6}$alkyl.

13. The compound of claim 12, wherein $L_1$ is selected from the group consisting of $C_{1-3}$alkylene $C_{3-5}$cycloalkylene, and $C_{3-6}$cycloalkylene-$C_{1-4}$alkylene.

14. The compound of any one of claims 12, where the compound is represented by:

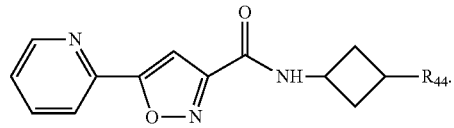

15. The compound of any one of claims 12, wherein $R_{44}$ is a 5-membered heteroaryl having two or three nitrogens.

16. The compound of any one of claims 12, wherein $R_{44}$ is a 5 membered heteroaryl having two nitrogens and an additional heteroatom selected from the group consisting of O and S.

17. The compound of any one of claims 12, wherein $R_{44}$ is substituted on a free carbon by a substituent selected from the group consisting of: a methyl substituted by one, two or three substituents each independently selected from the group consisting of halogen, hydroxyl, methoxy and ethoxy, ethyl substituted by one, two or three substituents each independently selected from the group consisting of halogen, hydroxyl, methoxy and ethoxy, propyl substituted by one, two or three substituents each independently selected from the group consisting of halogen, hydroxyl, methoxy and ethoxy, isopropyl substituted by one, two or three substituents each independently selected from the group consisting of halogen, hydroxyl, methoxy and ethoxy, n-butyl substituted by one, two or three substituents each independently selected from the group consisting of halogen, hydroxyl, methoxy and ethoxy, t-butyl substituted by one, two or three substituents each independently selected from the group consisting of halogen, hydroxyl, methoxy and ethoxy, s-butyl substituted by one, two or three substituents each independently selected from the group consisting of halogen, hydroxyl, methoxy and ethoxy and isobutyl substituted by one, two or three substituents each independently selected from the group consisting of halogen, hydroxyl, methoxy and ethoxy.

18. A compound selected from the group consisting of:

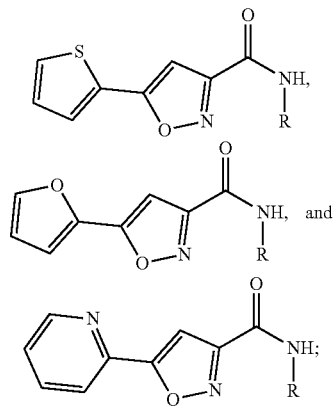

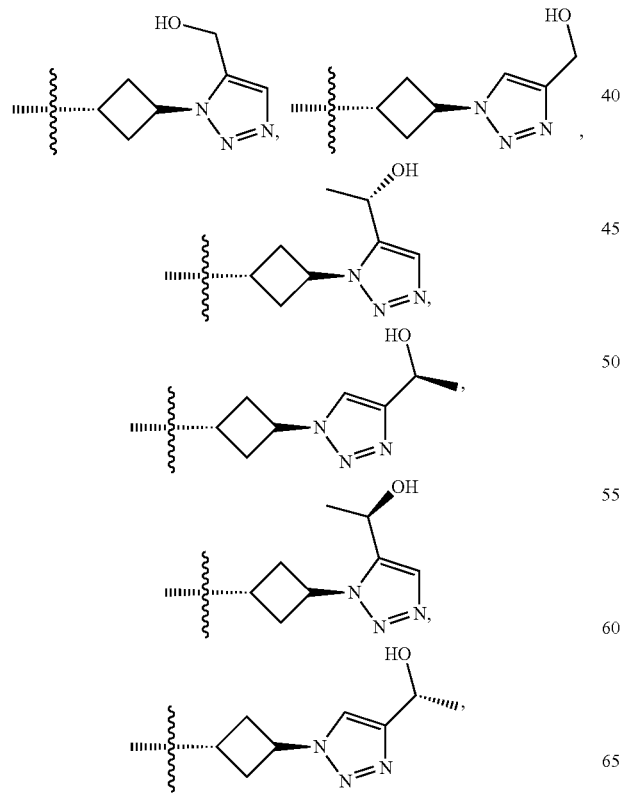

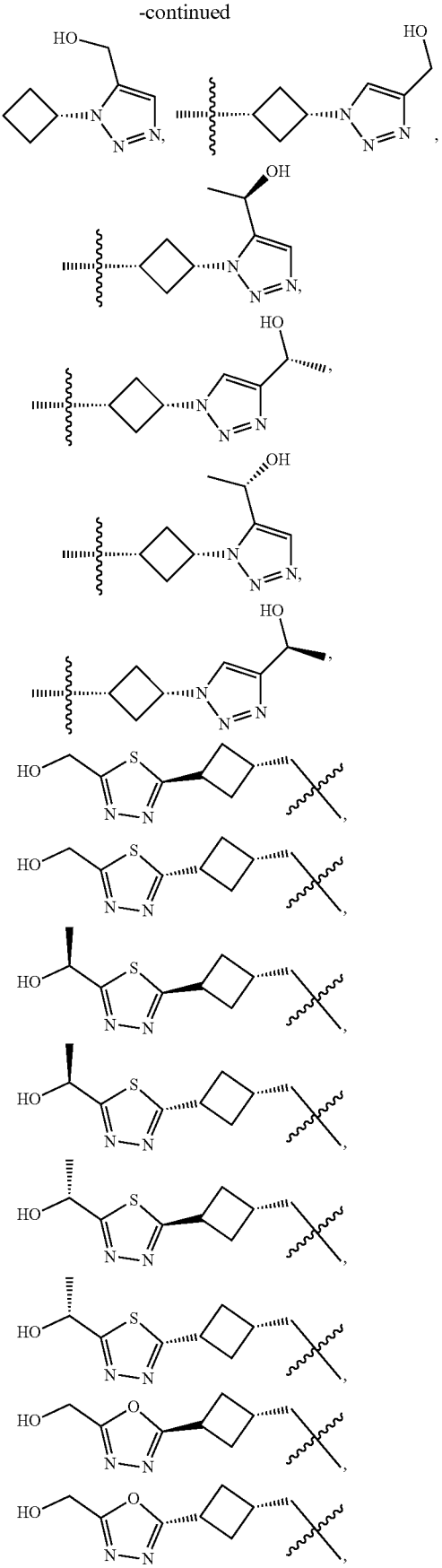

where R is selected from the group consisting of:

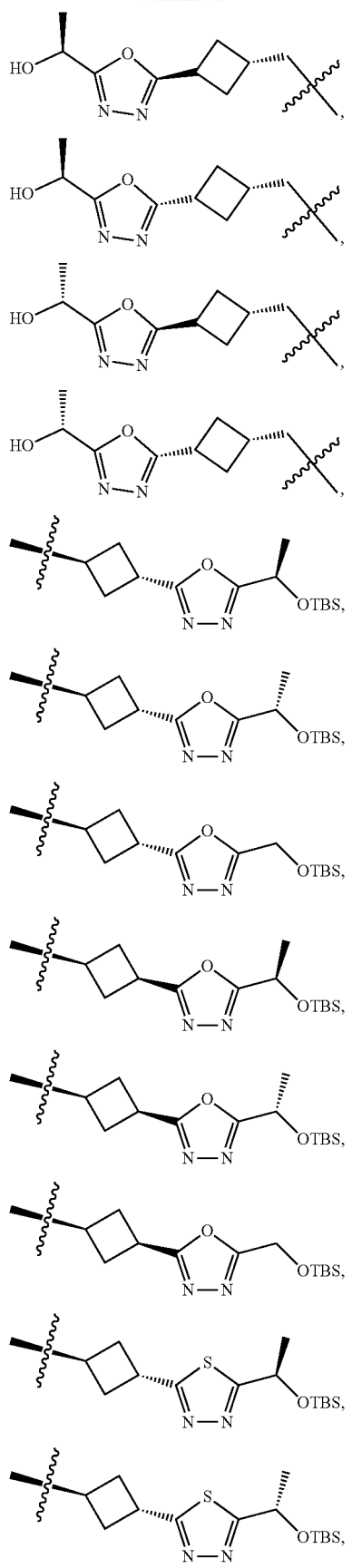
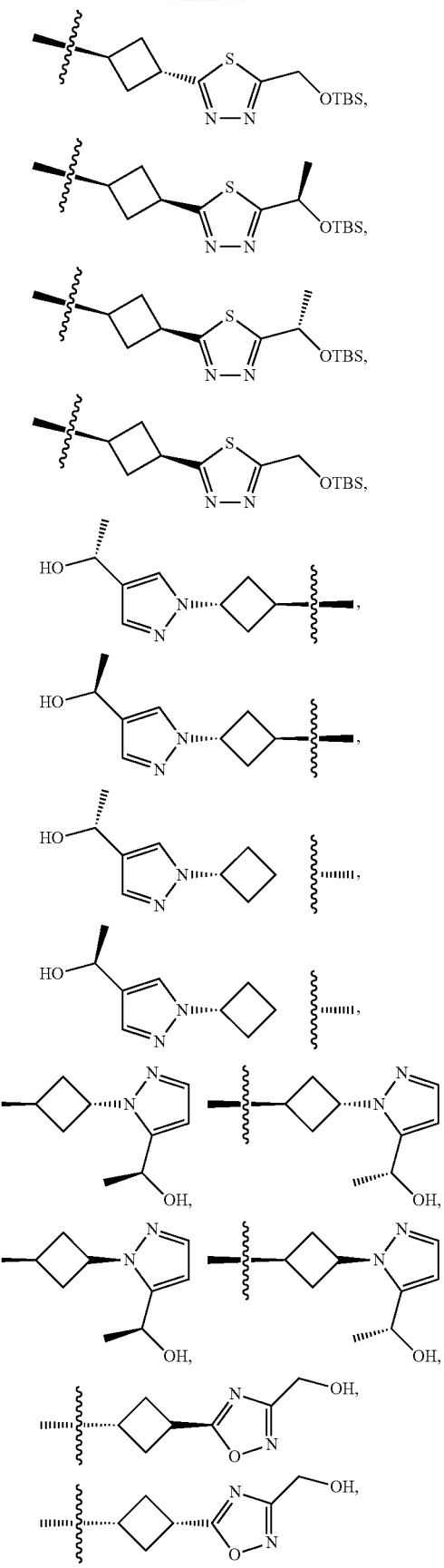

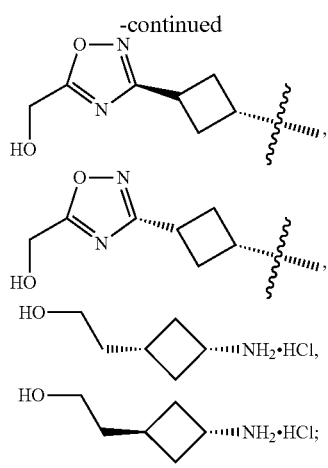

and a pharmaceutically acceptable salt thereof.

19. A pharmaceutical composition comprising a compound of any one of claims 1 and a pharmaceutically acceptable carrier or excipient.

20. A method of treating a patient suffering from cystic fibrosis comprising administering to said patient an effective amount of a compound represented by:

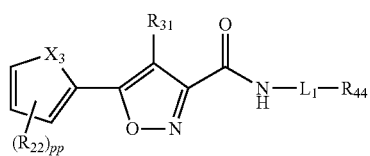

IV or a pharmaceutically acceptable salt or stereoisomer thereof, wherein;

$X_3$ is selected from the group consisting of O,S, And $NR_{hh}$;

pp is 1, 2, or 3;

$R_{22}$ is independently selected for each occurrence from the group consisting of hyfrogen and halogen;

$R_{31}$ is selected from the group consisting of hydrogen and halogen;

$L_1$ is selected from the consisting of $C_{3-5}$cycloalkylene, $C_{3-6}$cycloalkylene-$C_{1-4}$alkylene, $C_{1-3}$alkylene-$NR_{hh}$—$S(O)_w$—$NR_{hh}$—, $C_{3-6}$cycloalkylene-$C_{0-2}$alkylene-$S(O)_w$—$NR_{hh}$, and $C_{3-6}$cycloalkylene- $C_{0-2}$alkylene-$NR_{hh}$—$S(O)_w$—, wherein $L_1$ may be optionally substituted by one, two or three substituents each independently selected from the group consisiting of halogen, hydroxyl, and $C_{1-3}$alkyl (optionally substituted by one, two or three substituents each selected independently from $R_{ff}$);

$R_{44}$ is selected from the group consisting of heterocycle and 5-6 membered monocyclic heteroaryl or 8-10 membered bicyclic heteroaryl having one, two or three heteroatoms each independently selected from the group consisting of O, N, and S; wherein the heterocycle and the heteroaryl may be optionally substituted by one or two substituents each selected independently from $R_{gg}$;

$R_{ff}$ is independently selected for each occurrence from the group consisting of halogen, hydroxyl, $C_{1-4}$alkyl, $C_{1-4}$alkoxy, $C_{2-4}$alkenyl, $C_{3-6}$cycloalkyl, —NR'R", —NR'—$S(O)_w$—$C_{1-3}$alkyl, $S(O)_w$—NR'R", and —$S(O)_w$—$C_{1-3}$alkyl, where w is 0, 1, or 2, wherein $C_{1-4}$alkyl, $C_{1-4}$alkoxy, $C_{2-4}$alkenyl and $C_{3-6}$cycloalkyl may be optionally substituted by one, two or three substituents each independently selected from the group consisting of halogen, hydroxyl, —NR'R", —NR'—$S(O)_w$—$C_{1-3}$alkyl, $S(O)_w$—NR'R", and —$S(O)_w$—$C_{1-3}$alkyl;

$R_{gg}$ is independently selected for each occurrence from the group consisting of halogen,hydroxyl, $C_{1-6}$alkyl, $C_{1-6}$alkoxy, $C_{2-6}$alkenyl, $C_{3-6}$cycloalkyl, —NR'R", —NR'—$S(O)_w$—$C_{1-3}$alkyl, $S(O)_w$—NR'R", —O—Si(R''')$_3$, and —$S(O)_w$—$C_{1-3}$alkyl, where w is 0, 1, or 2, wherein $C_{1-6}$alkyl, $C_{1-6}$alkoxy, $C_{2-6}$alkenyl and $C_{3-6}$cycloalkyl may each be optionally substituted by one, two or three substituents each independently selected from the group consisting of halogen, $C_{1-6}$alkyl, $C_{1-6}$alkoxy, hydroxyl, C(O)OH, —C(O)O$C_{1-6}$alkyl, —O—$C_{3-6}$cycloalkyl, —O-heterocycle, —O-heteroaryl, —O -phenyl, —NR'R", —NR'—$S(O)_w$—$C_{1-3}$alkyl, —O—Si(R''')$_3$, $S(O)_w$—NR'R", and —$S(O)w$—$C_{1-3}$alkyl;

w is 0, 1 or 2;

$R_{hh}$ is independently selected for each occurrence from the group consisting of H, $C_{1-6}$alkyl, and $C_{3-6}$Cycloalkyl;

R' and R" are independently selected for each occurrence from the group consisting of H, $C_{1-6}$alkyl and $C_{3-6}$cycloalkyl; and R''' is independently selected for each occurrence from $C_{1-6}$alkyl.

* * * * *